(12) United States Patent
Mata Lopez et al.

(10) Patent No.: US 8,669,049 B1
(45) Date of Patent: Mar. 11, 2014

(54) METHOD AND DEVICE FOR THE DETECTION OF MUTATIONS IN ISOLATED GENE SEQUENCES OF THE LOW-DENSITY LIPOPROTEIN RECEPTOR (LDL-R) WHICH IS ASSOCIATED WITH FAMILIAL HYPERCHOLESTEROLEMIA

(75) Inventors: Pedro Mata Lopez, Barcelona (ES); Rodrigo Alberto Alonso Karlezi, Barcelona (ES); Pilar Mozas Alonso, Barcelona (ES); Gilberto Reyes Leal, Barcelona (ES); Miguel Pocovi Mieras, Barcelona (ES); Sergio Castillo Fernandez, Barcelona (ES); Diego Tejedor Hernandez, Barcelona (ES); Antonio Martinez Martinez, Barcelona (ES); Miguel Mallen Perez, Barcelona (ES)

(73) Assignee: Progenika Biopharma, S.A., Vizcaya (ES)

( * ) Notice: Subject to any disclaimer, the term of this patent is extended or adjusted under 35 U.S.C. 154(b) by 1244 days.

(21) Appl. No.: 10/542,937

(22) PCT Filed: Jan. 21, 2004

(86) PCT No.: PCT/ES2004/070001
§ 371 (c)(1),
(2), (4) Date: Sep. 8, 2006

(87) PCT Pub. No.: WO2004/067740
PCT Pub. Date: Aug. 12, 2004

(30) Foreign Application Priority Data

Jan. 28, 2003 (ES) .................................. 200300206
Nov. 17, 2003 (ES) .................................. 200302671

(51) Int. Cl.
*C12Q 1/68* (2006.01)
*C12P 19/34* (2006.01)
*C07H 21/02* (2006.01)

(52) U.S. Cl.
USPC .......................... 435/6.1; 435/91.2; 536/23.1

(58) Field of Classification Search
None
See application file for complete search history.

(56) References Cited

U.S. PATENT DOCUMENTS 4,966,837 A    10/1990   Brown et al.
2001/0053519 A1 *  12/2001   Fodor et al. .................. 435/6

FOREIGN PATENT DOCUMENTS

WO    WO 02/06467 A1    1/2002

OTHER PUBLICATIONS

Lucentini J 'Gene Association Studies Typically Wrong' The Scientist (Dec. 20, 2004) p. 20.*

Hegele, R.A. Arterioscler Thromb Vasc Biol. (2002) vol. 22, pp. 1058-1061.*
Juppner H. Bone (Aug. 1995) vol. 17, No. 2 Supplement, pp. 39S-42S.*
Hacker U.T. et al. Gut (May 1997) vol. 40, No. 5, pp. 623-627.*
Thisted R.A. 'What is a P-value?' (May 25, 1998) from www.stat.uchicago.edu/~thisted, pp. 1-6.*
Lombardi P. et al. Human Genetics (1997) vol. 99, pp. 106-107.*
Fouchier, S.W., et al. "The molecular basis of familial hypercholesterolemia in the Netherlands" Human Genetics (2001) vol. 109 pp. 602-615.
Pisciotta, L., et al. "A "de novo" mutations of the LDL-receptor gene as the cause of familial hypercholesterolemia" Biochimica of Biophysics Acta vol. 1587 2002 pp. 7-11.
Lind, S. et al "Genetic characterization of Swedish patients with familial hypercholesterolemia: a heterogeneous pattern of mutations in the LDL receptor gene" Atherosclerosis vol. 163 (2002) pp. 399-407.
Varret M. et al. "Results of the molecular analysis of the 220 point mutations in the human LDL receptor gene database" Atherosclerosis (1997) vol. 134 p. 74 (Abstract).
Tejedor, Diego, et al. "Reliable Low-Denisity DNA Array Basd on Allele-Specific Probes for Detection of 118 Mutations Causing Familial Hperchlosterolemia", Clinical Chemistry Vo. 51:7 pp. 1137-1144 (2005).
Alonso, R. "Cardiovascular disease in familial hypercholesterolaemia: Influence of low-density lipoprotein receptor mutation type and classic risk factors" , Atherosclerosis, pp. 1-7 (2008).
Civerira, Fernando, et al. "Comparison of Genetic Versus Clinical Diagnosis in Familial Hperchloestcrolemia" The American Journal of Cardiology(www.AJConline.org) , pp. 1-7 (2008).
Junyent, Mireia, et al. "Femoral Atherosclerosis in Heterozygous Familial Hypercholesterolemia: Influence of the Genetic Defect", Arterioscler Thromb Vasc Biol vol. 28, pp. 580-586 (2008).
Mozas Pilar, et al. "Molecular Characterization of Familial Hypercholsesterolemia in Spain: Identification of 39 Novel and 77 Recurrent Mutations in LDLR", Human Mutation Mutation in Brief vol. 735 pp. 1-13 (2004).

* cited by examiner

*Primary Examiner* — Stephen Kapushoc
(74) *Attorney, Agent, or Firm* — Ladas & Parry LLP

(57) ABSTRACT

The invention relates to extracorporeal methods of analyzing the presence or absence of mutations which cause familial hypercholesterolemia. The inventive methods describe the way in which said mutations can be detected using a DNA sample from an individual and comprising the following: chain reaction of the polymerase with primers which are complementary to the low-density lipoprotein receptor gene; analysis of the amplified product by sequencing; restriction analysis; single strand conformation polymorphism techniques; heteroduplex analysis and analysis of a device on top of a biochip glass support on which oligonucleotide probes are disposed, which can be used to detect the aforementioned mutations in the DNA.

7 Claims, 3 Drawing Sheets

METHOD AND DEVICE FOR THE DETECTION OF MUTATIONS IN ISOLATED GENE SEQUENCES OF THE LOW-DENSITY LIPOPROTEIN RECEPTOR (LDL-R) WHICH IS ASSOCIATED WITH FAMILIAL HYPERCHOLESTEROLEMIA

REFERENCE TO A SEQUENCE LISTING SUBMITTED ON COMPACT DISK

The official copy of the sequence listing is submitted on compact disk (CD). Two CDs, labeled Copy 1 and Copy 2, containing an ASCII formatted sequence listing with a file name of 015859-4SQ.TXT, created on Sep. 23, 2008, and having a size of 123 KB, have been filed. The sequence listing contained on these compact disks is part of the specification and is herein incorporated by reference in its entirety.

FIELD OF THE INVENTION

The present invention falls within the technical-diagnostic extra-corporeal "in vitro" biological samples sector, for determining an individual's predisposition to the disease named Familial Hypercholesterolemia.

BACKGROUND OF THE INVENTION

According to the WHO definition, atherosclerosis is a combination of changes in the intimae of the arteries resulting from focal accumulation of lipids and complex compounds, accompanied by fibrous tissue formation, calcification and in turn associated with changes in the media.

Atherosclerosis may be considered as a special form of arteriosclerosis with pathogenic significant deposition of lipids in the arterial wall. Most forms of arteriosclerosis involve fatty degeneration of vascular wall, the terms "arteriosclerosis" and "atherosclerosis" may be used synonymously (Assmann G. in "Lipid Metabolism and Atherosclerosis" Schattauer Verlag GMbH, Stuttgart 1982: 1).

Lipids are insoluble in aqueous solutions. Lipoproteins are the particles enabling transport of the lipids in the blood. Lipoproteins are divided into various categories according to their density, depending on how they can be separated by ultracentrifugation (Havel R J et al. J Clin Invest 1955, 34:1345). Low density-lipoproteins (LDL) (d=1.019-1.063 g/mL) transport the bulk of the cholesterol in the blood. They are composed of about 75% lipid (primarily cholesterol, cholesteryl esters and phospholipids), approximately 70% of the total cholesterol in the blood is transported by LDL particles.

Hypercholesterolemia is used to reflect a rise in plasma cholesterol higher than level considered normal for a particular population and is one of the critical factors in the onset and the progress of atherosclerosis. More than half of all deaths in Western society are related to atherosclerosis cardiovascular diseases (Murray C J L and Lopez A D. Lancet 1997; 349: 1269-1276).

Familial hypercholesterolemia (FH) is an autosomal dominant inherited disease produced in the receptor gene of the LDL (LDL-r) this gene codifies a protein that allows the intracellular uptake and degradation of the LDL (Goldstein J L, Brown M S Ann Rev Cell Biol 1985; 1:1-39).

The penetrance of FH is almost 100% meaning that half of the offspring of an affected parent has a severely elevated plasma cholesterol level from birth onwards, with males and females equally affected (Goldstein J L, Brown M S. The metabolic basis of inherited disease. Scriver C R, Beaudet A L, Sly W S, Valle D, eds. McGraw Hill New York 6$^{th}$ edition, 1989; 1215-1250).

FH affected individuals display arcus lipoides corneae, tendon xanthomas and premature symptomatic coronary heart disease (Scientific Steering Committee on behalf of the Simon Broome register Group. Atherosclerosis 1999; 142: 105-115). FH is one of the most common inherited disorders with frequencies of heterozygote patients of and homozygote estimated to be 1/500 and 1/1,000,000, respectively.

Certain populations, such as a small number of mutations predominate due to founder effects and therefore, the frequency of heterozygous FH is higher, these populations include French Canadians (Leitersdorf E et al. J Clin Invest 1990; 85:1014-1023), Christian Lebanese (Lehrman M A et al. J Biol Chem 1987; 262:401-410) Druze (Landsberger D et al. Am J Hum Genet 1992; 50: 427-433) Finns (Koivisto U M et al. J Clin Invest 1992; 90:219-228) South African Afrikaner (Kotze M J et al. Ann Hum Genet 1991; 55:115-121), and Ashkenazi Jews of Lithuanian descent (Meiner V et al. Am J Hum Genet 1991; 49:443-449) have the peculiarity that they have only a few mutations responsible for the FH, result of founder effects and therefore the frequency of heterozygous FH in those populations is higher than the estimate for other populations.

FH heterozygous patients display a very high plasma cholesterol concentration, generally above the 95$^{th}$ percentile value. In patients with FH the age-standardised and sex-standardised mortality ratios are four to five times higher than in the general population (Scientific Steering Committee on behalf of the Simon Broome Register Group. Atherosclerosis 1999; 142: 105-115). Patients who have inherited two mutant at the LDL-r locus are termed "FH homozygotes" or "FH compound heterozygotes", in which case those are practically no functional receptors which lead to a six-fold to eight-fold elevation in plasma LDL-c levels above normal. In the majority of these patients, a coronary heart disease typically occurs before the age of 20 years (Goldstein J L et al. N Engl J Med 1983; 309:288-296). If individuals with heterozygous or homozygous FH could be diagnosed before they develop symptomatic disease, they could be treated preventively to substantially reduce their risk of myocardial infarction.

The LDL-r is an ubiquitous trans-membrane glycoprotein of 839 amino acids that mediates the transport of LDL into cells via endocytosis (Goldstein J and Brown M J Biol Chem 1974; 249:5153-5162) (FIG. 1).

The LDL-r gene lies on the short arm of chromosome 19p13.1-13.3 (Yamamoto T et al. Cell 1984; 39: 27-38), spans 45,000 base pairs (bp). It comprises 18 exons and 17 introns encoding the six functional domains of the mature protein: Signal peptide, ligand-binding domain, epidermal growth factor (EGF) precursor like, O-linked sugar, trans-membrane and cytoplasmic domain (Sundhof T et al. Science 1985; 228:893-895) (FIG. 2).

The LDL-r synthesis is regulated by a sophisticated feedback mechanism that controls the transcription of the LDL-r gene in response to variations in the intracellular sterol concentration and the cellular demand for cholesterol (Sudhof T C et al J Biol Chem 1987; 262:10773-10779). DNA motifs necessary for transcriptional regulation of the LDL-r gene are located within 177 bp of the proximal promoter (Sudhof T C et al. J Biol Chem 1987; 262: 10773-10779). This region contains all the cis-acting elements for basal expression and sterol regulation and includes three imperfect direct repeats of 16 bp each. Repeat 1 and 3 containing binding sites for the transcriptional factor Sp1 and are essential for producing the basal expression of the gene but require the contribution of the repeat 2 for full expression (Dawson P A et al. J Biol Chem 1988; 263; 3372-3379). Repeat 2 contains a 10 bp regulatory element, SRE-1, (Smith J R et al. J Biol Chem 1990; 265: 2306-2310) that allows binding of the transcriptional factor designated as SREBP-1, when the intra-cellular sterol concentration diminishes. To date, several naturally-occurring mutations have been mapped to the transcriptional regulatory elements of the LDL gene receptor (Hobbs H H, et al. Hum Mutat 1992; 1:445-466; Koivisto U M, et al ProcNatl Acad Sci USA, 1994; 91:10526-10530), Mozas P, et al J Lipid Res 2002; 43:13-18, (worldwideweb: ucl.ac.uk/fh; worldwideweb:umd.necker.fr.)

Exon 1 encodes the signal peptide, a sequence of 21 amino acids, which is cleaved from the protein during the translocation into the endoplasmic reticulum. Several frameshift, missense and nonsense mutation has been described in this exon (worldwideweb: ucl.ac.uk/fh; worldwideweb: umd.necker.fr.)

Exons 2 to 6 encode the ligand binding domain, which consists of seven tandem repeats of 40 amino acids each. The structure of the ligand binding domain has been partially elucidated (Jeon H et al. Nature Struc Biol 2001; 8:499-5049). There are a cluster of negatively charged amino acids, Asp-X-Ser-Asp-Glu in each repeat and six cysteine residues that form three disulfide bonds.

The second domain of the human LDL-r consists of 400 amino acid sequence, encoded by exons 7 to 14. This sequence shows a 33% of homology of the epidermal growth factor precursor (EGFP). Like the ligand binding domain, this region also contains three repeats of 40 amino acids with cysteine-rich sequences. The first two repeats, designated A and B, are contiguous and separated from the third repeat, by a 280 amino acid region that contains five copies of the YWTD (Tyr-Trp-Thr-Asp) sequence. The EGFP like domain is fundamental for the acid-dependent dissociation of the LDL particles from the LDL-r and clathrin coat pits that takes place in the endosome during receptor recycling. Of the all mutations described to date, approximately 55% are located in the EGFP-homology region and 35% among the YWTD repeats worldwideweb: ucl.ac.uk/fk worldwideweb:umd.necker.fr.)

The third domain of the LDL-r that is encoded by exon 15, is a region rich in threonine and serine residues. The function of this domain is unknown, but it is known that in this region the carbohydrate chains are anchored. This region show minimal sequence conservation among six species analysed and it is thought that this domain play a role in the stabilization of the receptor (Goldstein et al. In The Metabolic and Molecular Basis of Inherited Disease. Sciver C R, Beaudet A L, Sly W S, Valle D. 7$^{th}$ Edition. McGraw Hill, 1995: 1981-2030).

The trans-membrane domain comprises 22 hydrophobic amino acids coded by exon 16 and the 5' end of exon 17. This domain is essential for anchoring the LDL-r to the cell membrane.

The cytoplasmic domain of the LDL-r, is formed by a sequence of 50 amino acids residues, is encoded by the 3' region of the exon 17 and the 5' end of the exon 18. This domain contains two sequence signals for targeting the protein to the cell surface and for localizing the receptor in coated pits (Yokode M, et al. J Cell Biol 1992; 117: 39-46). This domain is one of the most conservedm with a percentage of amino acids converved of 86% among six species analysed.

LDL-r mutations found in FH patients, have been classified into 5 classes: null alleles, transport defective alleles, binding defective alleles, internalization-defective alleles and recycling-defective alleles. As a general rule, each category is associated with mutations localised in a region of the gene that codes for one particular domain of the protein (Hobbs, H H, et al. Hum Mutat 1992; 1:445-466).

The heterogeneity in FH patients in relation to plasma LDL-c levels and coronary heart disease is due in part to differences in the nature of the mutation (Sun X M et al. Arterioscler Thromb Vas Biol 1993; 13:1680-1688, Kotze M J et al. Arterioscler Thromb Vas Biol 1993; 13:1460-1468; Gudnason V et al. Arterioscler Thromb Vas Biol 1997; 17:3092-3101). On the other hand, in FH heterozygote patients, the LDL-c lowering response after treatment with hydroxy-methylglutaryl coenzyme A (HMGCoA) reductase inhibitors depends in part on the nature of the mutation in the LDL-r gene (Leisterdorf E et al. Circulation 1993; 87:35-44; Jeenah M et al. Atherosclerosis 1993; 98:51-58, Sijbrands E J G et al. Atherosclerosis 1998; 136: 247-254).

The primary ligand for the receptor is LDL, which contains a single copy of a protein called apolipoprotein B-100 (ApoB-100) (Goldstein J and Brown M J Biol Chem 1974; 249:5153-5162). This apolipoprotein has a zone rich in basic amino acids and being the site where binding to the receptor (Borén J et al. J Clin Inves 1998; 101: 1084-1093). Several mutations located in the apolipoprotein B gene have been found altering the functional activity of the protein and decreasing its capacity for withdrawal LDL particles, and leading to accumulation of LDL cholesterol in plasma. To date, four mutations have been identified in the apo B-100 gene which cause a hypercholesterolemia named Familial Defective (BDF) apolipoprotein, all of them located in the LDL-r binding domain of the apo B-100 protein (residues 3130-3630): R3480W, R3500Q, R3500W and R3531C (Soria L et al. Proc Natl Acad Sci USA 1989; 86: 587-591; Pullinger C R, et al. J Clin Invest 1995; 95:1225-1234; Gaffney D, et al. Arterioscler Thromb Vasc Biol 1995; 15:1025-1029; Boren J, et al. J Biol Chem 2001; 276; 9214-9218). The CGG-to-CAG mutation at codon for amino acid 3500, resulting in a glutamine substitution for arginine (R3500Q), is the most frequent alteration causing Familial Defective apolipoprotein B-100 (FDB). Patients heterozygous for the apoB-3500 mutation are usually hypercholesterolemic, although serum cholesterol concentrations can vary from those found in FH to only modest elevations (Tybjaerg-Hansen A, et al. Atherosclerosis 1990; 80:235-242; Hansen P S, et al. Arterioscl Throm Vasc Biol 1997; 17:741-747). Since clinical and biochemical characteristics in those patients are very similar, the differential diagnostic between patients with FDB or FH is only possible by genetic molecular diagnosis.

The clinical diagnosis of FH is based on the analytical data of lipids and lipoproteins in the plasma, clinical symtomatology (xanthomas) and family and personal coronary disease history. The WHO, through its MedPed program recommends a series of criteria be followed to perform the clinical diagnosis of FH. These criteria are based on a scoring system relying on the personal and family history of hypercholesterolemia, of the patient's clinical and analytic characteristics. When the punctuation reached by the patient is equal to or higher than 8 points the clinical criterion of FH diagnosis is classed as "certain", between 5 and 8 points as "likely and between 3 and 5 points as "possible" (Familial Hypercholesterolemia. Report of a second WHO consultation. The International MedPed FH Organization, Geneva 1998). However, some patients do not fulfil the FH criteria, because the family history is incomplete or unknown, or because at the time of the analysis they presented only moderate concentrations of plasmatic cholesterol and lacked signs of tissue cholesterol deposition, as tendinosous xanthomas, arcus corneae or xanthelasmas.

In families whose mutation of the r-LDL gene is known, it has been demonstrated that the best "cut-off" point for the diagnosis is use of the 90th percentile for the c-LDL concentration (Umans-Eckenhausen MAW et al. Lancet 2001; 357: 165-168. However, 18% of FH patients carriers of the mutation have a total cholesterol concentration below this percentile and moreover the proportion of false positives was 18%. Therefore, there will be a high percentage of wrong diagnoses if only the plasmatic cholesterol figure is utilized. It has been published that more than 50% of patients do not receive lipid lowering therapy and dietary counseling as a result of not having been diagnosed correctly as patients with FH (Williams R R et al., Am J Cardiol. 1993; 72:18 D-24D).

The elucidation of the molecular basis of FH has made diagnosis at the DNA level feasible in the vast majority of cases. Demonstration of an underlying defect in the LDL-r gene, constitutes in fact the definite confirmation of the diagnosis (Familial hypercholesterolemia. Report of a second WHO consultation. The International MedPed FH Organization, Geneva 1998). Although accurate diagnosis of FH is possible by means of molecular methods, their use in heterogeneous populations is limited at present owing to mutational heterogeneity of the LDL-r gene.

In application PCT WO-88/03175 (Biotechnology Research Partners, Ltd.) a method is claimed for the diagnosis of atherosclerosis, based on detection of the presence or absence of various polymorphisms in the gene region of the apolipoprotein AO-CIII-AIV, or in the genes apoB, apoCI, apoAII, as well as in the LDL receptor gene. Specifically for this gene, utilization of the polymorphisms Cfr131 and BstEII is presented.

Another document of interest is Japanese patent JP-10099099 which refers to the use of a mutation in the codifier triplet of the amino acid 109, specifically the insertion of a C, for the diagnosis of abnormalities in the LDL receptor gene, although familial hypercholesterolemia is not specifically mentioned.

Finally, U.S. Pat. No. 4,745,060 and U.S. Pat. No. 4,966,837, both of the University of Texas, present methods for the diagnosis of familial hypercolesterolemia on the basis of mutations in the LDL receptor gene. However, what is claimed in the first of them are sequences corresponding to the "normal" gene, presenting a particular example of a mutation that is defined by the restriction map change with Xba I. In the second patent, on its part, the use of various restriction enzymes is claimed (Eco RI, Asp 718, Taq I, Bam HI, Xba I, Inf. I, Bgl II, Cla I, Eco RV, Kpn I, Pvu II, Sph I, Sst I, Sst II, Stu I, Xho I, Nde I and Nsi I) in a method for determining mutations in the LDL-r gene, based on observing the alteration of the restriction model with these enzymes compared to the model corresponding to the normal gene.

The closest patent document to the invention is WO02/06467, in which a method is described, for the detection of errors in the lipidic metabolism based on a series of mutations and polymorphisms of the LDL-r gene. However, none of the mutations or polymorphisms described in said patent coincides with those claimed in the present application.

DETAILED DESCRIPTION OF THE INVENTION

The nomenclature of the mutations and polymorphisms is defined in
Antoranakis S. E. and the Nomenclature Working Group, Recommendations for Nomenclature Systems for Human Gene Mutations. Human Mutation 11:1-3; 1998

Dunnen J T, Antoranakis S. E. Mutation Nomenclature Extensions and Suggestions to describe Complex Mutations: A Discussion. Human Mutation 15: 7-12, 2000.
Similarly the concept of the polymorphisms is defined in
Harris H. The Principles of Human Biochemical Genetics $3^{rd}$ Edition. Amsterdam. North-Holland 1980.
Beauder A L, Scriver C L, Sly W S, Valle D. Genetics, Biochemistry and Molecular Basis of Variant Human Phenotypes, in The Metabolic and Molecular Bases of Inherited Disease. Editores Beaudet A L, Scriver C R, Sly W S, Valle D $7^{th}$ Edition. Page 53, MacGraw Hill. New York 1995.

There has been detected, isolated and characterized a whole series of new mutations which are detailed below. Similarly, a whole series of mutations and polymorphisms already described, have combined with them to analyze the likelihood of an individual developing familial hypercholesterolemia. All of the mutations and polymorphisms which in this invention relate to development of familial hypercholesterolemia are produced in the gene sequence SEQ ID NO:1 corresponding to the low density lipoproteins receptor gene (LDL-r). That is to say, all of the mutations are produced in the same gene, are used in the same testing device, using the same technology to determine, using the same method, extracorporeally and in vitro, the likelihood of developing the same disease, which supports the unitary nature of the invention.

In Table I all of the new mutations detected are detailed, according to the nomenclature scientifically approved and detailed in the publications mentioned above. Likewise, they are provided with an alpha-numerical code.

In Table II mutations are detailed, already described and known, whose use in combination with the mutations of Table I, in testing devices in vitro for diagnosis of the familial hypercholesterolemia is one of the preferred forms, new and inventive, of embodiment of the invention. Similarly, in analogous manner to that mentioned for the known mutations, in Table DI polymorphisms are detailed.

The amino acid mutations are represented in one-letter codes which have their equivalence according to Table IV.

TABLE I

| MUTATION | ID |
|---|---|
| (−23)A > C | M002 |
| 1054 del11 | M006 |
| 108delC | M008 |
| 1197del9 | M009 |
| 1207delT | M010 |
| 1432delG | M012 |
| 191 − 2delAinsCT | M016 |
| 2184delG | M020 |
| 231delC | M022 |
| 2399del5/ins4 | M024 |
| 313 + 1insT | M027 |
| 338del16 | M029 |
| 509insC | M030 |
| 675del15 | M032 |
| 684dup12 | M034 |
| 941 − 39C > T | M041 |
| C195R | M046 |
| C255G | M0100 |
| C319Y | M050 |
| D157G | M059 |
| D630N | M063 |
| E291X | M068 |
| H635N | M096 |
| N59K | M074 |
| T41M | M097 |
| W515X | M098 |
| Y379X | M092 |
| Y421X | M093 |

TABLE I-continued

| MUTATION | ID |
|---|---|
| T433N | M105 |
| 818del8 | M110 |
| 1423delGC/insA | M111 |
| 1204insT | M112 |
| 451del3 | M115 |
| G516X | M117 |
| 2389 + 4A > G | M120 |
| 1815del11 | M121 |
| 1186 + 5G > A | M129 |
| T740M | M131 |
| I771T | M135 |
| R279G | M138 |
| T446I | M141 |
| H562Q | M142 |
| C74Y | M145 |
| D686Y | M147 |
| G(−2)R | M149 |
| E579D | M150 |
| S205C | M151 |
| D200V | M153 |
| V766E | M154 |
| L(−6)P | M155 |
| 2544insC | M156 |
| C42Y | M157 |
| 2389 + 3A > C | M160 |
| [1587 − 5del5; 1587del31] | M161 |

TABLE II

| MUTATION | ID | MUTATION | ID |
|---|---|---|---|
| 2393del 9 | M001 | C646Y | M053 |
| (−42)C > G | M003 | C677Y | M054 |
| (−49)C > T | M004 | C68W | M055 |
| 1045delC | M005 | C74G | M056 |
| 1061 − 8T > C | M007 | C95R | M057 |
| A378T | M0102 | D151N | M058 |
| C358R | M0104 | D200G | M060 |
| 1358 + 1G > A | M011 | D200Y | M061 |
| 1706 − 10G > A | M014 | D280G | M062 |
| 1845 + 1G > C | M015 | E10X | M064 |
| 2085del19 | M017 | E246A | M066 |
| 211del G | M018 | E256K | M067 |
| 2140 + 5G > A | M019 | F634L | M069 |
| 2207insT | M021 | G322S | M070 |
| 2390 − 1G > C | M023 | G352D | M071 |
| 313 + 1G > C | M025 | G571E | M072 |
| 313 + 1G > A | M026 | N543H | M073 |
| 313 + 2insT | M028 | N804K | M075 |
| 518 del G | M031 | Q12X | M076 |
| 7delC | M035 | Q133X | M077 |
| 872delC | M036 | Q357P | M078 |
| 884delT | M038 | Q427X | M079 |
| 920ins4 | M039 | Q71E | M080 |
| A519T | M042 | R395Q | M081 |
| C113W | M043 | R574W | M082 |
| C127R | M045 | R612C | M083 |
| C255X | M047 | S156L | M084 |
| C281Y | M048 | S205P | M085 |
| C297F | M049 | T413K | M086 |
| C347Y | M051 | T7051 | M087 |
| C371X | M052 | V502M | M089 |
| W(−18)X | M090 | | |
| W541X | M091 | | |
| D679E | M094 | | |
| 1359 − 1G > A | M099 | | |
| 681ins21 | M033 | | |
| C122X | M044 | | |
| V408M | M088 | | |
| G528D | M106 | | |
| D412H | M107 | | |
| N619N | M108 | | |
| E80K | M109 | | |
| L534P | M113 | | |
| L621S | M114 | | |

TABLE II-continued

| MUTATION | ID | MUTATION | ID |
|---|---|---|---|
| C356Y | M116 | | |
| R329X | M119 | | |
| G248D | M122 | | |
| C201Y | M125 | | |
| 313 + 5G > A | M126 | | |
| C358Y | M127 | | |
| C331R | M128 | | |
| D157N | M130 | | |
| V776M | M134 | | |
| P664L | M136 | | |
| W462X | M137 | | |
| Q328X | M139 | | |
| L584P | M140 | | |
| R395W | M143 | | |
| G314V | M144 | | |
| W469X | M146 | | |
| P678L | M148 | | |
| R612H | M152 | | |
| R236W | M159 | | |

TABLE III

| POLYMORPHISMS | ID |
|---|---|
| 81T > C BstUI Exón 2 | P1 |
| 1060 + 10G>C SmaI Exón 7 | P2 |
| 1171G > A StuI Exón 8 | P3 |
| 1413G > A DdeI Exón 10 | P4 |
| 1617C > T BstNI Exón 11 | P5 |
| 1725C > T SSCP Exón 12 | P6 |
| 1771C > T HincII Exón 12 | P7 |
| 1959 T > C AvaII Exón 13 | P8 |
| 2232G > A MspI Exón 15 | P9 |

TABLE IV

| AMINOACID NOMENCLATURE | | |
|---|---|---|
| Alanine | Ala | A |
| Aspartic acid | Asp | D |
| Glutamic acid | Glu | E |
| Glycine | Gly | G |
| Phenylalanine | Phe | F |
| Leucine | Leu | L |
| Serine | Ser | S |
| Tyrosine | Tyr | Y |
| Cysteine | Cys | C |
| Tryptophan | Trp | W |
| Leucine | Leu | L |
| Proline | Pro | P |
| Histidine | His | H |
| Glutamine | Gln | Q |
| Arginine | Arg | R |
| Isoleucine | Ile | I |
| Methionine | Met | M |
| Threonine | Thr | T |
| Asparagine | Asn | N |
| Lysine | Lys | K |
| Serine | Ser | S |
| Arginine | Arg | R |
| Valine | Val | V |
| Stop codon | Ter | X |

The diagnosis assay "biochip" developed in the invention is a slide with a large amount of probes onto its surface shown in the sequences list. These oligonucleotide probes are able to hybridize with the mutant sequences included in Tables I to III. The methodology involved for each mutation is:

Printing of Glass Slides

The oligonucleotides capable of detecting the mutation are printed onto an aminosilanized glass slide using DMSO as printing buffer.

Printing is carried out with a "spotter" or oligonucleotides printer wherein temperature and humidity are controlled.

Processing of the Glass Slides

After printing the slides undergo treatment with UV radiation.

Target-DNA Preparation

Genomic DNA of the patient is extracted from a blood sample of approximately 300 μl by using a filtration method.

A multiplex-PCR reaction is performed allowing amplification for each patient of the promoter and all 18 exons of the LDL receptor gene A biotinylated nucleotide is incorporated during the PCR process. As an indirect labeling method, a final step of staining with a fluorophore-streptavidin coupler is required after hybridization.

PCR products are electrophoresed and visualized in agarose gel.

Target-DNA is fragmented.

Hybridization buffer is added to the fragmented PCR products.

Denaturation step takes place at 95° C. 15 min.

Hybridization

Hybridization is carried out automatically in the station designed by Amersham Biosciences for this purpose.

The glass slide is prehybridized.

The hybridization solution is injected with a Hamilton pipelet.

One hour is the hybridization time.

The glass slide is washed three times and dried.

The station dres the glass slide

Scanning of Glass Slide

The glass slide in inserted in the scanner.

The signal is scanned emitted by the standard marker on being stimulated by the laser.

Quantification of Image

The scanner software allows us to quantify in the image obtained the signal of the points where hybridisation has occurred.

From the signal obtained in the oligonucleotides which detect the normal allele and the mutated one we establish the presence or absence of the mutation in the patient.

Each mutation has in the glass slide four oligonucleotides repeated 10 times for their detection. Two of them detect the normal allele and another two the mutated. The interrogated base is to be found in central position throughout.

In the case of a normal patient (FIG. 3A), he does not present mutated allele. Therefore, in the image obtained from the glass slide the oligonucleotides that detect said allele do not show hybridisation signal or a lesser signal than the oligonucleotides that detect the normal allele.

On the contrary, a heterozygous individual (FIG. 3B) for the mutation has the normal allele and the mutated one. Hence, the oligonucleotides which detect the normal allele and the mutated one have an equivalent hybridisation signal.

The results of the hybridisation of the DNA-chip with marked PCRs, produced from the DNA of the individuals to be analysed, demonstrate that the individual represented in FIG. 3A does not have a particular mutation in the LDL-r gene which occasions a change of E256K amino acid, and that the individual of FIG. 3B is heterozygous for this mutation.

In this way the heterozygous individual would be diagnosed genetically as Familial Hypercholesterolemic.

By means of analysis examples some of the mutations are next detailed, detected with the assay device of the invention.

Example 1

Identification of Mutations Located in Exon 1 of the LDLr Gene

A 215 bp fragment of exon 1 of the LDLr gene was amplified by polymerase chain reaction (PCR) using the primers Ex1F (SEQ ID NO: 2) y Ex1R (SEQ ID NO: 3).

DNA (500 ng) was amplified in a 50 μL reaction mixture containing 20 mM Tris-HCl, pH 8.4, 50 mM KCl, 1.5 mM $MgCL_2$, 200 μM each dNTP, 0.2 μM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 59° C. for 1 min, and elongation at 74° C. for 2 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by using the device described "biochip".

(−23)A>C Mutation Analysis

This mutation creates a new Ava H recognition site. Five microliters of the exon 1 amplied material were hydrolized with 15 units of Ava II in a total volume of 30 μL according to the protocol described by the manufacturer (NEB, Beverly, Mass., USA). The fragments obtained had a length of 148 and 67 bp for normal alleles and 93, 67 and 55 bp for mutant alleles. These fragments were separated by electrophoresis in 8% polyacrilamide gel and were visualised by staining with ethidium bromide. Alternatively, this mutation could be analyzed with the device described ("biochip") using in the slide the oligonucleotides: SEQ ID NO: 36, SEQ ID NO: 37, SEQ ID NO: 38 and SEQ ID NO: 39.

(−23)A>C mutation was detected in a 60 years old woman with arcus corneae and xanthelasmas having been diagnosed as having familial hypercholesterolemia with a diagnostic score of 8 points in line with the MedPed (Familial Hypercholesterolemia. Report of a second WHO consultation. The International MedPed FH Organization, Geneva 1998). No evidence of premature cardiovascular event was detected in near relation with her family. The plasmatic concentration of lipids before the pharmacological treatment were: Total cholesterol (TC) 352 mg/dL, LDL-c 271 mg/dL, and the triglycerides (TG) and cholesterol of the high density lipoproteins (HDL-c) were within the normal range. Hypolypemiant treatment with simvastatin (20 mg/da) lowered her TC and LDL-c levels to 251 and 171 mg/dL respectively.

L(−6)P Mutation Analysis

This mutation (47T>C, CTC>CCC, Leu(−6)Pro) was characterized by automatic sequencing of the 215 bp fragment corresponding to exon 1 of the LDL-r gene on analysing this fragment clinically diagnosed as FH. The sequencing reaction was carried out in a PE Gene Amp System 9700 thermocyclator using the reagents of the CET 2000 Dye Terminator Cycle Sequencing kit with Beckman's Quick Start (Beckman Coulter, Palo Alto, Calif., USA) and the primers Ex1F (SEQ ID NO:2) and Ex1R (SEQ ID NO:3). The fragments generated by the sequencing reaction were analysed in an automatic sequencer CEQ 2000XL NDA Beckman Analysis System. The change T>C observed was confirmed by automatic sequencing of a second PCR product of the same sample. Alternatively, this mutation can be analysed with the device described ("biochip") using in the slide the oligonucleotides SEQ ID NO:240, SEQ ID NO:241, SEQ ID NO:242 and SEQ ID NO: 243.

The L(−6)P mutation was detected in a 47 years old woman with arcurs corneae whose father had hypercholesterolemia with a TC of 350 mg/dL and two paternal uncles with hypercholesterolemia had died of myocardium attack at the age of 24 and 33 respectively. The clinical diagnosis of hypercholesterolemia familiar reached a score of 9 points according to MedPed criteria. The plasmatic concentrations of lipids prior to pharmacological treatment were: TC 420 mg/dl, LDL-c 320 mg/dL, TG 155 mg/dL and HDL-c 49 mg/dL. Treatment with atorvastatin (15 mg/day) lowered her TC and LDL-c levels to 289 and 233 mg/dL respectively.

G(−2)R Mutation Analysis

This mutation ((58G>A, GGG>AGG, Gly(−2)Arg) was characterized by automatic sequencing of the 215 bp fragment from exon 1 of the LDL-r gene on analysing this fragment in patients clinically diagnosed as FH. Purified PCR product from DNA sample were directly sequenced in both directions using the amplification primers Ex1F (SEQ ID NO:2) and Ex1R (SEQ ID NO:3) and the kit CEQ 2000 Dye Terminator Cycle Sequencing with Quick Start (Beckman Coulter, Palo Alto, Calif., USA) according to the protocol described by the manufacturer. Sequences were detected using the CEQ 8000 Genetic Analysis System (Beckman Coulter, Inc. Fullerton), and analyzed with CEQ 8000 software. The 58G>A change was confirmed by sequencing a second PCR product. Alternatively, this mutation could be analyzed with the microarray ("biochip") using in the slide the oligonucleotides: SEQ ID NO: 220, SEQ ID NO: 221, SEQ ID NO: 222 and SEQ ID NO: 223.

G(−2)R mutation was identified in a 34 years old woman with arcurs corneae whose mother had hypercholesterolemia with a TC of 400 mg/dL. Her score for FH clinical diagnostic was 10 points following MedPed criteria. Her plasma lipid levels before treatment were: TC 354 mg/dL, LDL-c 264 mg/dL, normal TG and HDL-c of 64 mg/dL.

Example 2

Identification of Mutations Located in Exon 2 of the LDLr Gene

A 183 bp fragment of exon 2 was amplified by polymerase chain reaction (PCR) using the following desoxynucleotides: Ex2F (SEQ ID NO: 4) and Ex2R (SEQ ID NO: 5).

The amplification reaction was performed in a 50 µL final volume with 500 mg DNA in a mixture of 20 mM Tris-HCl, pH 8.4, 50 mM KCl, 1.5 mM $MgCL_2$, 200 µM each dNTP, 0.2 µM each desoxyoligonucleotide and 1.5 units of Taq DNA polymerase (Gibco BRL, Carlsbad, Calif., USA). The amplification cycles were: 10 min of denaturation at 96° C., followed by 35 cycles: denaturation at 94° C. for 1 min, hybridization at 59° C. for 1 min, and elongation at 72° C. for 2 min, and a final extension of 72° C. for 10 min.

PCR products were analyzed by Single Strand Conformation Polymorphisms (SSCP) and those fragments that showed an abnormal SSCP pattern were sequenced using an automated CEQ 2000XL DNA Analysis System (Beckman Coulter, Palo Alto, Calif., USA). The presence of a mutation identified by sequencing was subsequently analyzed by restriction analysis and with the device described "biochip".

108delC Mutation Analysis

This mutation creates a new MnlI digestion site. Fifteen microliters of the exon 1 amplified material were hidrolized with 15 units of MnlI in a total volume of 30 µL according to the protocol described by the manufacturer (Fermentas Inc., Hanover, Md., USA). The fragments obtained had a length of 150 and 33 bp in normal alleles and 118, 33 and 32 bp in mutant alleles. These fragments were separated by electrophoresis in 8% polyacrilamide gel and were visualised by staining with ethidium bromide. Alternatively, this mutation could be analyzed with the device described ("biochip") using in the slide the oligonucleotides: SEQ ID NO: 40, SEQ ID NO: 41, SEQ ID NO: 42 and SEQ ID NO: 43

108delC mutation was detected in a 50 years old woman, without any clinical skin manifestation of her hypercholesterolemia. She was diagnosed clinically as having FH MedPed score of 9 points. Premature cardiovascular disease was detected in one first degree familial. Fasting plasma lipid levels while off hypolipidemic drug therapy were: TC (381 mg/dL), TG (142 mg/dL), LDLc (321) mg/dL) and HDLc (32 mg/dL).

T41M Mutation Analysis

This mutation (185C>T, ACG>ATG, Thr41Met) destroys a cleavage restriction site for the enzyme Tail. Fifteen microliters of the exon 1 amplified material were hydrolized with 15 units of Tail in a total volume of 30 µL according to the protocol described by the manufacturer (NEB, Beverly, Mass., USA). The fragments obtained had a length of 154 and 29 bp for normal alleles and 183 bp for mutant alleles. These fragments were separated by electrophoresis in 8% polyacrilamide gel and were visualised by staining with ethidium bromide. Alternatively, this mutation could be analyzed with the device described ("biochip") using in the slide the oligonucleotides: SEQ ID NO: 140, SEQ ID NO: 141, SEQ ID NO: 142 and SEQ ID NO: 143.

T41M mutation was detected in a 69 years old man who suffered a myocardial infarction at the age of 55 years and that has been diagnosed as having familial hypercholesterolemia with a diagnostic score of 6 points according to MedPed criteria. Evidence of premature cardiovascular event was detected in relatives. Analysis of his fasting serum without the use of lipid lowering drugs were: TC (274 mg/dL) and LDL-c (217 mg/dL) with normal TG and HDLc levels.

C42Y Mutation Analysis

This mutation (C42Y (188G>A, TGC>TAG, Cys42Tyr) was characterized by sequencing of the 183 bp fragment corresponding to exon 2 during screening for mutations in the LDL-r gene in subjects clinically diagnosed as FH. Purified PCR product from DNA sample were directly sequenced in both directions using the amplification primers Ex2F (SEQ ID NO:4) and Ex2R (SEQ ID NO:5) and the kit CEQ 2000 Dye Terminator Cycle Sequencing with Quick Start (Beckman Coulter, Palo Alto, Calif., USA) according to the protocol described by the manufacturer. Sequences were detected using the CEQ 8000 Genetic Analysis System (Beckman Coulter, Inc. Fullerton), and analyzed with CEQ 8000 software. The G>A change was confirmed by sequencing a second independent PCR product. Alternatively, this mutation could be analyzed with the microarray ("biochip") using in the slide the oligonucleotides: SEQ ID NO: 248, SEQ ID NO: 249, SEQ ID NO: 250 and SEQ ID NO: 251

C42Y mutation was detected in a 17 years old man with arcus lipoides corneae that has been diagnosed as having familial hypercholesterolemia with a diagnostic score of 10 points, according to MedPed. His mother had severe hypercholesterolemia. Analysis of his fasting serum without the use of lipid lowering drugs were: TC (350 mg/dL) with normal TG and HDLc levels. Hypolypemiant treatment with simvastatin (20 mg/day) lowered his TC and LDL-c levels to 274 and 214 mg/dL respectively.

C74Y Mutation Analysis

This mutation C74Y (284 G>A, TGC>TAC, Cys74Tyr) was identified by DNA sequencing of the 196 bp fragment from exon 3 during screening for mutations in the LDL-r gene in subjects clinically diagnosed as FH. Purified PCR product from DNA sample were directly sequenced in both directions using the amplification primers Ex3F (SEQ ID NO:6) y Ex3R (SEQ ID NO:7) and the kit CEQ 2000 Dye Terminator Cycle Sequencing with Quick Start (Beckman Coulter, Palo Alto, Calif., USA) according to the protocol described by the manufacturer. Sequences were detected using the CEQ 8000 Genetic Analysis System (Beckman Coulter, Inc. Fullerton), and analyzed with CEQ 8000 software. The G>A change was confirmed by sequencing a second independent PCR product. Alternatively, this mutation could be analyzed with the microarray ("biochip") by spotting onto the slide the oligonucleotides: SEQ ID NO: 212, SEQ ID NO: 213, SEQ ID NO: 214 y SEQ ID NO: 215.

C74Y mutation was detected in a 52 years old man with arcus cornealis, tendon xanthomas and family history of hypercholesterolemia. He has been diagnosed as having familial hypercholesterolemia with a diagnostic score of 17 points according to the MedPed criteria. Analysis of her fasting serum before the use of lipid lowering drugs were: TC (420 mg/dL) TG (96 mg/dL) and HDLc (69 mg/dL). Treatment with an HMGCoA reductase inhibitor (10 mg/day) lowered his LDL-c levels by 22%.

Example 3

Identification of Mutations Located in Exon 3 of the LDLr Gene

A 196 bp fragment of exon 3 of the LDLr gene was amplified by polymerase chain reaction (PCR) using the following primers: Ex3F (SEQ ID NO: 6) y Ex3R (SEQ ID NO: 7).

DNA (500 ng) was amplified in a 50 μL reaction mixture containing 20 mM Tris-HCl, pH 8.4, 50 mM KCl, 1.5 mM $MgCL_2$, 200 μM each dNTP, 0.2 μM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 59° C. for 1 min, and elongation at 72° C. for 1 min, and a final extension of 72° C. for 10 min.

PCR products were analyzed by Single Strand Conformation Polymorphisms (SSCP) and those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

191-2delAinsCT Mutation Analysis

As this mutation does not change the restriction map, we designed a pair of mutagenic primers to introduce the recognition site of BfaI in presence of the normal allele but not in presence of mutant allele.

A 184 bp fragment of exon 3 of the LDLr gene was amplified by polymerase chain reaction (PCR) using the following primers: Ex3R (SEQ ID NO: 7) y Mut191-2F (SEQ ID NO: 8).

DNA (500 ng) was amplified in a 50 μL reaction mixture containing 20 mM Tris-HCl, pH 8.4, 50 mM KCl, 1.5 mM $MgCL_2$, 200 μM each dNTP, 0.2 μM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 59° C. for 1 min, and elongation at 72° C. for 2 min, and a final extension of 72° C. for 10 min.

Fifteen microliters of PCR sample were hydrolized with 15 units of BfaI in a total volume of 30 μL according to the protocol described by the manufacturer (NEB, Beverly, Mass., USA). The fragments obtained had a length of 23 and 161 bp for normal alleles and 185 bp for mutant alleles. These fragments were separated by electrophoresis in 8% polyacrilamide gel and were visualized by staining with ethidium bromide.

Alternatively, this mutation could be analyzed with the microarray ("biochip") using in the slide the oligonucleotides: SEQ ID NO: 44, SEQ ID NO: 45, SEQ ID NO: 46 and SEQ ID NO: 47.

191-2delAinsCT mutation was detected in two unrelated families with autosomal dominant hypercholesterolemia. The index case of one of these families, was a 58 years old woman, with tendon xanthomas, xanthelasmas, angina pectoris, family history of coronary heart disease and hypercholesterolemia. She has been diagnosed as having familial hypercholesterolemia with a MedPed diagnostic score of 15 points. Her plasma lipid levels were: TC (559 mg/dL) and LDLc (467 mg/dL), TG (175 mg/dL) and HDLc (57 mg/dL). Treatment with simvastatin (40 mg/day) lowered her TC and LDL-c levels to 302 and 228 mg/dL respectively.

N59K Mutation Analysis

This mutation (240C>A, AAC>AAA, Asn59Lys) destroys a cleavage endonuclease site for the enzyme Hindi. Fifteen μL of PCR sample were digested with 15 units of Hindi in a total volume of 30 μL according to the protocol described by the manufacturer (Amersham Pharmacia Biotech Inc., Piscataway, N.J., USA). The fragments obtained had a length of 111 and 85 bp (normal alleles) or 196 bp (mutant alleles). These fragments were separated by electrophoresis in 8% polyacrilamide (PAA) gel and were visualized by staining with ethidium bromide.

Alternatively, this mutation could be analyzed with the microarray ("biochip") using in the slide the oligonucleotides: SEQ ID NO: 48, SEQ ID NO: 49, SEQ ID NO: 50 y SEQ ID NO: 51.

N59K mutation was detected in a 43 years old man diagnosed clinically as having FH with a MedPed diagnostic score of 12 points. His plasma lipid levels without lipid lowering therapy were TC (465 mg/dL), LDLc (397 mg/dL), TG (100 mg/dL) and HDLc (48 mg/dL). The hypolypemiant treatment with simvastatin (40 mg/dy) lowered his TC and LDL-c levels to 350 and 282 mg/dL respectively. On the other hand, his mother had suffered an angine pectoris at the age of 58 and he has a son of 8 years old with hypercholesterolemia TC (325 mg/dL) and LDLc (241 mg/dL).

231delC Mutation Analysis

This mutation destroys a endonuclease HaeIII digestion site. Fifteen microliters of PCR sample were digested with 15 units of HaeIII in a total volume of 30 μL according to the protocol described by the manufacturer (Gibco BRL, Carlsbad, Calif., USA). The fragments obtained had a length of 76, 51, 42 and 25 bp for normal alleles and 117, 51, and 27 bp for mutant alleles. These fragments were separated by electrophoresis in 8% polyacrilamide (PAA) gel and were visualized by staining with ethidium bromide.

Alternatively, this mutation could be analyzed with the device described ("biochip") using in the slide the oligonucleotides: SEQ ID NO: 52, SEQ ID NO: 53, SEQ ID NO: 54y SEQ ID NO: 55

The mutation was detected in a 37 years old woman, with arcus corneae. She was diagnosed clinically as having FH with a score of 16 points following the WHO MedPed criteria.

Plasma lipid levels without lipid lowering therapy were: TC (543 mg/dL), LDLc (456 mg/dL), TG (178 mg/dL) and HDL-c (51 mg/dL). The hypolypemiant treatment with atorvastatin (40 mg/day) and colestipol (20 g/day) lowered her TC and LDL-c levels to 260 and 190 mg/dL respectively. Her brother suffered a myocardial infarction at the age of 38 and her son of 12 years old have hypercholesterolemia with TC concentration of 305 mg/dL.

313+1insT Mutation Analysis

This mutation creates a new cleavage site for the restriction endonuclease TruII. Fifteen microliters of the exon 3 amplified material were hydrolized with 15 units of TruII in a total volume of 30 µL according to the protocol described by the manufacturer (Fermentas Inc., Hanover, Md., USA). The fragments obtained had a length of 196 bp for normal alleles and 162 and 34 bp for mutant alleles. These fragments were separated by electrophoresis in 3% NuSieve agarose gel and were visualized by staining with ethidium bromide.

Alternatively, this mutation could be analyzed with the device described ("biochip") using in the slide the oligonucleotides: SEQ ID NO: 56, SEQ ID NO: 57, SEQ ID NO: 58 y SEQ ID NO: 59.

313+1insT mutation was detected in a 53 years old woman, with xanthomas and arcus corneae. No premature cardiovascular events was detected in her available family members. She was diagnosed clinically as having FH with a MedPed score of 19 points. Analysis of her fasting serum lipid levels without the use of lipid lowering drugs were: TC (574 mg/dL) and LDLc (505 mg/dL) with normal TG and HDLc levels. After lipid lowering hypolypemiant treatment with simvastatin (80 mg/day) and colestipol (20 g/day) their TC and LDL-c levels decreased at 282 mg/dL and 225 mg/dL respectively.

Example 4

Identification of Mutations Located in Exon 4 of the LDLr Gene

A 242 bp fragment of LDL-r gene from the 5' region of exon 4 (exon 4A) was amplified by polymerase chain reaction (PCR) using the following primers: Ex 4AF (SEQ ID NO: 9) y Ex 4AR (SEQ ID NO: 10)

DNA (500 ng) was amplified in a 50 µL reaction mixture containing 20 mM Tris-HCl, pH 8.4, 50 mM KCl, 1.5 mM $MgCL_2$, 200 µM each dNTP, 0.2 µM each primer and 1.5 units of Taq DNA polymerase (Gibco BRL, Carlsbad, Calif., USA). The amplification cycles were: 10 min of denaturation at 96° C., followed by 35 cycles of denaturation at 94° C. for 1 min, annealing at 63° C. for 1 min, and elongation at 72° C. for 2 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

338del16 Mutation Analysis

This mutation creates a new cleavage site for the restriction endonuclease Van91I. Fifteen microliters of the exon 4 amplified material were hydrolized with 15 units of Van91I in a total volume of 30 µL according to the protocol described by the manufacturer (Amersham Pharmacia Biotech Inc., Piscataway, N.J., USA). The fragments obtained had a length of 242 bp for normal alleles and 174 and 52 bp for mutant alleles. These fragments were separated by electrophoresis in 2% agarose gel and were visualized by staining with ethidium bromide.

Alternatively, this mutation could be analyzed with the device described ("biochip") using in the slide the oligonucleotides SEQ ID NO: 144, SEQ ID NO: 145, SEQ ID NO: 146 y SEQ ID NO: 147.

338del16 mutation was detected in three unrelated families with autosomal dominant hypercholesterolemia. One index case of these families, was a 40 years old man with xanthomas and arcus corneae, TC 542 mg/dL and LDLc 441 mg/dL and normal TG and HDLc levels. He was diagnosed as having FH with a MedPed score of 19 points. No cardiovascular event was detected in his available family members. The hypolypemiant treatment with atorvastatin (10 mg/day) lowered his plasma TC and LDL-c levels to 293 and 218 mg/dL respectively.

5090insC Mutation Analysis

As this mutation does not change the restriction map, we designed a pair of mutagenic primers to introduce one recognition site for the restriction enzyme MnlI in presence of the mutant allele but not in presence of normal allele.

A 244 bp fragment of exon 4A was amplified by polymerase chain reaction (PCR) using the following primers: Ex4AF (SEQ ID NO: 9 and Mut509insCR (SEQ ID NO: 11).

DNA (500 ng) was amplified in a 50 µL reaction mixture containing 20 mM Tris-HCl, pH 8.4, 50 mM KCl, 1.5 mM $MgCL_2$, 200 µM each dNTP, 0.2 µM each primer and 1.5 units of Taq DNA polymerase (Gibco BRL, Carlsbad, Calif., USA). The amplification cycles were: 10 min of denaturation at 96° C., followed by 35 cycles of denaturation at 94° C. for 1 min, annealing at 65° C. for 1 min, and elongation at 72° C. for 1 min, and a final extension of 72° C. for 10 min.

Fifteen microliters of PCR sample were digested with 15 units of MnlI in a total volume of 30 µL according to the protocol described by the manufacturer (Fermentas Inc., Hanover, Md., USA). The fragments obtained had a length of 141, 99 and 4 bp for normal alleles for 141, 88, 12 and 4 bp in mutant alleles. These fragments were separated by electrophoresis in 8% polyacrilamide gel and were visualized by staining with ethidium bromide.

Alternatively, this mutation could be analyzed by the device described ("biochip") using in the slide the oligonucleotides SEQ ID NO: 60, SEQ ID NO: 61, SEQ ID NO: 62 and SEQ ID NO: 63.

509insC mutation was detected in a 44 years old woman with hypercholesterolomia TC (477 mg/dL) and LDLc (394 mg/dL) with normal without personal and familial history of premature coronary heart disease. Their diagnostic score was 9, following the MedPed criteria. She has two brothers with hypercholesterolemia at a c-LDL concentration beyond 95.

451del3 mutation analysis

This mutation (451del3) was characterized by DNA sequencing of the 242 bp fragment from exon 4 (4A) during screening for mutations in the LDL-r gene in subjects clinically diagnosed as having FH. Purified PCR product from DNA sample were directly sequenced in both directions using the amplification primers Ex4AF (SEQ ID NO:9) and Ex 4AR (SEQ ID NO:10) and the kit CEQ 2000 Dye Terminator Cycle Sequencing with Quick Start (Beckman Coulter, Palo Alto, Calif., USA) according to the protocol described by the manufacturer. Sequences were detected using the CEQ 8000 Genetic Analysis System (Beckman Coulter, Inc. Fullerton), and analyzed with CEQ 8000 software. The three base pair deletion was confirmed by sequencing a second PCR products. Alternatively, this mutation could be analyzed with the microarray ("biochip") by using in the slide the oligonucleotides: ID NO: 172, SEQ ID NO: 173, SEQ ID NO: 174 and SEQ ID NO: 175.

451del3 mutation was detected in a 36 years old man with arcus lipoides corneae that has been previously suffered a myocardial infarction at age of 34. He has two children 2 and 8 years olds with TC of 320 and 275 mg/dl respectively. He was diagnosed clinically as having FH with a score of 17 points. Analysis of his fasting serum lipids without the use of lipid lowering drugs were TC 449 mg/dl, LDL-c 367 mg/dL, TG 218 mg/dL and c-HDL-c 38 mg/dL. Treatment with simvastatin (40 mg/day) lowered his LDL-c level to 270 mg/dL.

Example 5

Identification of Mutations Located in Exon 4B of the LDLr Gene

A 237 bp fragment of 3' exon 4 (exon 4B) of the LDLr gene was amplified by polymerase chain reaction (PCR) using the following primers: Ex4BF (SEQ ID NO: 12) and Ex4BR (SEQ ID NO: 13).

DNA (500 ng) was amplified in a 50 µL reaction mixture containing 20 mM Tris-HCl, pH 8.4, 50 mM KCl, 1.5 mM MgCL$_2$, 200 µM each dNTP, 0.2 µM each primer and 1.5 units of Taq DNA polymerase (Gibco BRL, Carlsbad, Calif., USA). The amplification cycles were: 10 min of denaturation at 96° C., followed by 35 cycles of denaturation at 94° C. for 1 min, annealing and elongation at 72° C. for 2 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the microarray ("biochip").

D157G Mutation Analysis

This mutation (533A>G, GAT>GGT, Asp195Gly) creates a new digestion site for the endonuclease HphI. Fifteen microliters of the exon 4B amplified material were hydrolized with 15 units of HphI in a total volume of 30 µL according to the protocol described by the manufacturer (NEB, Beverly, Mass., USA). The fragments obtained had a length of 237 bp for normal alleles and 175 and 62 bp for mutant alleles. These fragments were separated by electrophoresis in 3% NuSieve agarose gel and were visualized by staining with ethidium bromide. Alternatively, this mutation could be analyzed with the device described ("biochip") using in the slide the oligonucleotides SEQ ID NO: 64, SEQ ID NO: 65, SEQ ID NO: 66 and SEQ ID NO: 67.

D157G mutation was detected in a 32 years old woman with hypercholesterolemia. No cardiovascular event was detected in her family. She was diagnosed clinically as having possible FH with a MedPed score of 6 points. Analysis of her fasting serum lipids before the use of lipid lowering therapy were: TC (358 mg/dL) and LDLc (296 mg/dL) with normal TG and HDLc levels. Treatment with atorvastatin (10 mg/day) lowered her plasma TC and LDL-c levels to 212 and 140 mg/dL respectively. Her father also had elevated levels of plasma cholesterol TC 364 mg/dL, as well as her grandmother 341 mg/dL.

C195R Mutation Analysis

This mutation (646T>C, TGT>CGT, Cys195Arg) creates a BshNI digestion site. Fifteen microliters of the exon 4B amplified material were hydrolized with 15 units of BshNI in a total volume of 30 µL according to the protocol described by the manufacturer (Fermentas Inc., Hanover, Md., USA). The fragments obtained had a length of 237 bp, corresponding to the amplified material without hydrolizing, for normal alleles and 159 and 78 bp for mutant alleles. These fragments were separated by electrophoresis in 8% polyacrilamide (PAA) gel and were visualized by staining with ethidium bromide. Alternatively, this mutation could be analyzed by the device described ("biochip") using in the slide the oligonucleotides SEQ ID NO: 68, SEQ ID NO: 69, SEQ ID NO: 70 and SEQ ID NO: 71.

C195R mutation was detected in a 64 years old woman who have hypercholesterolemia and arcus corneae. Premature cardiovascular disease was detected in her mother. She was diagnosed clinically as having FH with a MedPed score of 11 points Plasma lipid levels without lipid lowering therapy were: TC (560 mg/dL) and LDLc (468 mg/dL) with normal TG and HDLc levels.

675del15 Mutation Analysis

This mutation was identified by heteroduplexes analysis; the electrophoresis in 8% polyacrilamide gel of the exon 4B amplified material PCR visualized by staining with ethidium bromide, showed the presence of heteroduplexes bands instead of the corresponding normal and mutated homoduplexes. The fragments obtained had a length of 237 bp in normal alleles and 222 bp in mutant alleles. The heteroduplex band migrated more slowly because of the formation of the bubble between the michtmached sequences. Alternatively, this mutation could be analyzed with the microarray ("biochip") by spotting onto the slide the oligonucleotides SEQ ID NO: 72, SEQ ID NO: 73, SEQ ID NO: 74 y SEQ ID NO: 75.

675del15 mutation was detected in a 63 years old woman, clinically diagnosed as having FH with a MedPed score of 8 points. No cardiovascular event was detected in her family. An untreatment lipid determination gave us the following results: TC (450 mg/dL) and LDLc (379 mg/dL) with normal TG and HDLc levels. No family members were available to complete the genetic study.

684dup12 Mutation Analysis

This mutation was analysed by digestion of the exon 4B amplified fragment with MnII enclonuclease restriction site. The addition of 12 bp produced by the mutation, allows detecting the presence of the mutation in the exon 4B amplified material by electrophoresis in 8% polyacrilamide gel and tinction of the gel with ethidium bromide. Additionally, fifteen microliters of the exon 4B amplified material were hydrolized with 15 units of MnII in a total volume of 30 µL according to the protocol described by the manufacturer (Fermentas, Inc., Hanover, Md., USA). The fragments obtained had a length of 192 and 45 bp for normal alleles and 204 and 45 bp for mutant alleles. These fragments were separated by electrophoresis in 8% polyacrilamide gel and were visualized by staining with ethidium bromide. Alternatively, this mutation could be analyzed with the device described ("biochip") by spotting onto the slide the oligonucleotides SEQ ID NO: 76, SEQ ID NO: 77, SEQ ID NO: 78 and SEQ ID NO: 79

684dup12 mutation was detected in two unrelated families having autosomal dominant hypercholesterolemia. The index case of one of these families, was a 63 years old man, with xanthomas and arcus corneae He has been suffered a myocardial infarction at the age of 55 and was diagnosed clinically as having FH with a MedPed score of 17 points. No cardiovascular event was detected in his family. Plasma lipid levels without lipid lowering therapy were: TC (469 mg/dL), LDLc (408 mg/dL), TG (100 mg/dL) and HDLc 41 mg/dL.

D200V Mutation Analysis

This mutation (D200V (662A>T, GAC>GTC, Asp200Val)) was identified by DNA sequencing of the 237 bp fragment from exon 4 (4B) during screening for mutations in the LDL-r gene in subjects clinically diagnosed as having FH. Purified PCR product from DNA sample were directly sequenced in both directions using the amplification primers Ex4BF (SEQ ID NO:12) and Ex 4BR (SEQ ID NO:13) and the kit CEQ 2000 Dye Terminator Cycle Sequencing with Quick Start (Beckman Coulter, Palo Alto, Calif., USA) according to the protocol described by the manufacturer. Sequences were detected using the CEQ 8000 Genetic Analysis System (Beckman Coulter, Inc. Fullerton), and analyzed with CEQ 8000 software. The 662A>T change was confirmed by sequencing a second PCR product. Alternatively, this mutation could be analyzed with the device described ("biochip") using in the slide the oligonucleotides: SEQ ID NO: 232, SEQ ID NO: 233, SEQ ID NO: 234 and SEQ ID NO: 235.

D200V mutation was detected in a family with autosomal dominant hypercolesterolemia. The subject was a 43 years old woman with family history of hypercholesterolemia in infancy and whose mother and brother presented LDL-c levels above the 95 percentile. She was diagnosed clinically as having familial hypercholesterolemia with a score of 8 points, following the MedPed criteria. Analysis of her fasting serum lipids using lipid lowering drug pravastatin (40 mg/day) were TC 329 mg/dl, LDL-c 273 mg/dL, TG 73 mg/dL and HDL-c 41 mg/dL.

S205C Mutation Analysis

This mutation S205C (677C>G, TCT>TGT, Ser205Cys) was identified by DNA sequencing of the 237 bp fragment from exon 4 (4B) during screening for mutations in the LDL-r gene in subjects clinically diagnosed as having FH. Purified PCR product from DNA sample were directly sequenced in both directions using the amplification primers Ex4BF (SEQ ID NO:12) and Ex 4BR (SEQ ID NO:13) and the kit CEQ 2000 Dye Terminator Cycle Sequencing with Quick Start (Beckman Coulter, Palo Alto, Calif., USA). The fragments generated by the sequencing reaction were analysed in an automatic sequencer CEQ 2000XL DNA Beckman Analysis System. The C>G change observed was confirmed by automatically sequencing a second PCR product of the same ample. Alternatively, this mutation could be analyzed with the device described ("biochip") by spotting onto the slide the oligonucleotides: SEQ ID NO: 228, SEQ ID NO: 229, SEQ ID NO: 230 and SEQ ID NO: 231.

S205C mutation was detected in a 39 years old woman with family history of hypercholesterolemia (mother and brother TC 450 mg/dL and 500 mg/dL respectively) with two children with TC above the 95 percentile. She was diagnosed clinically at 20 years old as having familial hypercholesterolemia with a MedPed score of 8 points The plasmatic lipid concentrations prior to pharmalogical treatment were: TC 390 mg/dl, LDL-c 325 mg/dL and HDL-c 35 mg/dL. Treatment with simvastatin (10 mg/day) lowered her plasma LDL-c level to 270 mg/dL.

Example 6

Identification of Mutations Located in Exon 6 of the LDLr Gene

A 179 bp fragment of exon 6 of the LDLr gene was amplified by polymerase chain reaction (PCR) using the following primers: Ex6F (SEQ ID NO: 14) y Ex6R (SEQ ID NO: 15).

DNA (500 ng) was amplified in a 50 □L reaction mixture containing 20 mM Tris-HCl, pH 8.4, 50 mM KCl, 1.5 mM MgCL$_2$, 200 □M each dNTP, 0.2 □M each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 56° C. for 1 min, and elongation at 72° C. for 1 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

C255G Mutation Analysis

As this mutation C255G (826T>G, TGC>GGC, Cys255Gly) does not change the restriction map, a desoxyoligonucleotide was designed and synthetized with nonadjoining base to introduce the recognition site of BstUI restriction enzyme in presence of the mutant allele, which disappears in the presence of normal allele.

A 163 bp fragment of exon 6 of the LDLr gene was amplified by polymerase chain reaction (PCR) using the following primers: Ex6R (SEQ ID NO: 15) and MutC255GF (SEQ ID NO: 16).

DNA (500 ng) was amplified in a 50 □L reaction mixture containing 20 mM Tris-HCl, pH 8.4, 50 mM KCl, 1.5 mM MgCL$_2$, 2000M each dNTP, 0.2 □M each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 63° C. for 1 min, and elongation at 72° C. for 2 min, and a final extension of 72° C. for 10 min.

Fifteen µL of PCR sample were digested with 15 units of BstUI in a total volume of 30 µL according to the protocol described by the manufacturer (NEB, Beverly, Mass., USA). The fragments obtained had a length of 163 bp for normal alleles and 141 and 22 bp for mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides SEQ ID NO: 80, SEQ ID NO: 81, SEQ ID NO: 82 and SEQ ID NO: 83.

C255G mutation was detected in a 63 years old woman, with family history of hypercholesterolemia. A lipid determination with treatment were: TC (439 mg/dL) and LDLc (355 mg/dL) with normal TG and HDLc levels. She was diagnosed clinically as having familial hypercholesterolemia with a MedPed score of 8 points E291X Mutation Analysis As this mutation E291X (934G>T, GAG>TAG, Asp291Stop) does not change the restriction map, a desoxyoligonucleotide was designed and synthesized with a nonadjoining base to create a recognition site fro the restriction enzyme SspI in presence of the mutated allele which disappears in the presence of the normal allele.

A 164 bp fragment of exon 6 of the LDLr gene was amplified by polymerase chain reaction (PCR) using the following primers: Ex6F (SEQ ID NO: 13) and Mut E291XR (SEQ ID NO: 17).

DNA (500 ng) was amplified in a 50 □L reaction mixture containing 20 mM Tris-HCl, pH 8.4, 50 mM KCl, 1.5 mM MgCL$_2$, 200 □M each dNTP, 0.2 □M each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 59° C. for 1 min, and elongation at 72° C. for 1 min, and a final extension of 72° C. for 10 min.

Fifteen μL of PCR sample were digested with 15 units of SspI in a total volume of 30 μL according to the protocol described by the manufacturer (Amersham Pharmacia Biotech Inc., Piscataway, N.J., USA). The fragments obtained had a length of 164 bp (non-digested fragment) for normal alleles and 144 and 20 bp for mutant alleles. These fragments were electrophoresed in 3% NuSieve agarose gel and were visualized by staining with ethidium bromide.

Alternatively, this mutation could be analyzed with the device described ("biochip") by spotting onto the slide the oligonucleotides SEQ ID NO: 84, SEQ ID NO: 85, SEQ ID NO: 86 y SEQ ID NO: 87.

E291X mutation was detected in a family with autosomal dominant hypercholesterolemia family. The subject was a 44 years old man with arcus corneae and concentrations: TC (381 mg/dL), HDLc (45 mg/dL), TG (111 mg/dL) and LDLc (314 mg/dL). His clinical diagnosis of hypercholesterolemia familiar reached a score of 12 points, according to the MedPed criteria. Combined lipid lowering treatment with simvastatin (40 mg/day) and colestiramin (12 g/day) lowered his plasma TC and LDL-c levels to 253 mg/dL and 188 mg/dL.

818del8 Mutation Analysis

This mutation was identified by heteroduplexe analysis; the electrophoresis in 8% polyacrilamide (PAA) gel of amplified product of exon 6 visualized by staining with ethidium bromide, showed the presence of heteroduplexes bands instead of the corresponding normal and mutated homoduplexes of 179 and 171 bp, readily distinguishable in the gel after staining with ethidium bromide. The two heteroduplex bands migrated more slowly because of the formation of the bubbles between the mismatched sequences.

In addition the mutation could be confirmed by PCR amplification of exon 6 and restriction analysis, the 818del8 mutation creates a new MaeIII endonuclease restriction site. Fifteen μL of PCR sample were digested with 15 units of MaeIII in a total volume of 30 μL according to the protocol described by the manufacturer (Roche Diagnostics, Manheim, Germany). The fragments obtained had a length of 118, 34 and 27 bp for normal alleles and 118 and 53 bp for mutant alleles. These fragments were electrophoresed in 8% of polyacrilamide and were visualized by staining with ethidium bromide. Alternatively, this mutation could be analyzed with the device described ("biochip") by spotting onto the slide the oligonucleotides SEQ ID NO: 160, SEQ ID NO: 161, SEQ ID NO:162 and SEQ ID NO: 163.

818del8 mutation was detected in a 69 years old woman, clinically diagnosed as having FH with a MedPed score of 10 points. Her two sons have hipercholesterolemia with plasma TC levels of 382 and 304 mg/dL respectively. The clinical diagnosis of family hypercholesterolemia reached a score of 10 points on MedPed criteria. The plasmatic lipid concentrations prior to pharmacological treatment were: TC (530 mg/dL) and LDLc (439 mg/dL) TG(170 mg/dL and HDLc 57 mg/dL Lipid lowering treatment with cerivastatin (0.4 mg/day) reduced her LDL-c to 363 mg/dL.

R279G Mutation Analysis

This mutation R279G (898A>G, AGA>GGA, Arg279Gly) was identified by automatic sequencing of the 179 bp fragment from exon 6 during screening for mutations in the LDL-r gene in subjects clinically diagnosed as FH. Purified PCR product from DNA sample were directly sequenced in both directions using the amplification primers Ex6F (SEQ ID NO:14) and Ex6R (SEQ ID NO:15) and the kit CEQ 2000 Dye Terminator Cycle Sequencing with Quick Start (Beckman Coulter, Palo Alto, Calif., USA) The fragments generated by the sequence reaction were analysed in an automatic sequencer CEQ 2000XL DNA Beckman Analysis System. The A>G change observed was confirmed by sequencing a second PCR product of the same sample.

Alternatively, this mutation could be analyzed with the device described ("biochip") by spotting onto the slide the oligonucleotides: SEQ ID NO: 200, SEQ ID NO: 201, SEQ ID NO: 202 and SEQ ID NO: 203.

R279G mutation was identified in a 59 years old woman with xantelasmas and family history of hypercholesterolemia in the father and two brothers. The score for FH clinical diagnostic was 10 points Plasma lipid levels before treatment were: TC 384 mg/dL, LDL-c 314 mg/dL and normal TG and HDL-c levels. Lipid lowering treatment with simvastatin (80 mg/day) lowered her LDL-c to 167 mg/dL.

Example 7

Identification of Mutations Located in Exon 7 of the LDLr Gene

A 234 bp fragment of exon 7 of the LDLr gene was amplified by polymerase chain reaction (PCR) using the following primers Ex7F (SEQ ED NO: 18) y Ex7R (SEQ ID NO: 19.

DNA (500 ng) was amplified in a 50 □L reaction mixture containing 20 mM Tris-HCl, pH 8.4, 50 mM KCl, 1.5 mM $MgCL_2$, 200 □M each dNTP, 0.2 □M each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 57° C. for 1 min, and elongation at 72° C. for 1 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of a mutation identified by sequencing was subsequently analysed by restriction analysis and with the device described previously ("biochip").

941-39C>T Mutation Analysis

This mutation destroys an ApaI digestion site. Fifteen μL of exon 7 PCR sample were digested with 15 units of ApaI in a total volume of 30 μL according to the protocol described by the manufacturer (Fermentas Inc., Hanover, Md., USA). The fragments obtained had a length of 186, 26 and 22 bp for normal alleles and 208 and 26 bp for mutant alleles. These fragments were electrophoresed in 8% polyacrilamide (PAA) gel and were visualised by staining with ethidium bromide. Alternatively, this mutation could be analyzed with the device described ("biochip") by spotting onto the slide the oligonucleotides SEQ ID NO: 88, SEQ ID NO: 89, SEQ ID NO: 90 y SEQ ID NO: 91.

941-39C>T mutation was detected in four unrelated families who had the characteristic in common of having an autosomal dominant familiar hypercholesterolemia. The index case of one of these families was a 61 years old woman who had suffered a myocardium attack and with a family history of premature cardiovascular disease. She was clinically diagnosed as having FH with a MedPed score of 7 points. Plasma lipid levels before treatment were: TC (340 mg/dL) and LDLc (248 mg/dL) with TG 136 mg/dL and HDL-c 65 mg/dL. After lipid lowering treatment with atorvastatin (20 mg/day) TC and LDL-c levels decreased at 233 mg/dL and 144 mg/dL respectively with no significant changes in TG and HDL-c levels.

C319Y Mutation Analysis

This mutation C319Y (1019G>A, TGC>TAC, Cys319Tyr) creates a new RsaI endonuclease digestion site. Fifteen μL of PCR sample were digested with 15 units of RsaI in a total volume of 30 µL according to the protocol described by the manufacturer (Gibco BRL, Carlsbad, Calif., USA). The fragments obtained had a length of 234 bp (fragment without digestion) in normal alleles and 136 and 98 bp in mutant alleles. These fragments were electrophoresed in 8% polyacrilamide (PAA) gel and were visualized by staining with ethidium bromide. Alternatively, this mutation could be analyzed with the device described ("biochip") by spotting onto the slide the oligonucleotides SEQ ID NO: 92, SEQ ID NO: 93, SEQ ID NO: 94 y SEQ ID NO: 95

C319Y mutation was detected in a family with autosomal dominant familial hypocholesterolemia. The subject was a 43 years old man, with arcus corneae and xanthomas at Achilles tendon and dorsum of the hands and corneal arc and with a 17 years old son with total plasmatic cholesterol of 384 mg/dL. His father had suffered sudden death at 45 years of age. He was clinically diagnosed as having FH with a MedPed score of 22 points. Plasma lipid levels before treatment were: TC (428 mg/dL) and LDLc (372 mg/dL) with normal TG level.

1054del11 Mutation Analysis

This mutation destroys an endonuclease restriction site for the HphI enzyme. Fifteen µL of the amplified material of exon 7 were digested with 15 units of HphI in a total volume of 30 µL according to the protocol described by the manufacturer (Gibco BRRL, Carlsbad, Calif., USA). The fragments obtained had a length of 189 and 45 bp in normal alleles and 223 bp in mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides SEQ ID NO: 96, SEQ ID NO: 97, SEQ ID NO: 98 y SEQ ID NO: 99

1054del11 mutation was detected in a family with autosomal dominant familial hypercholesterolemia. The subject was a 43 years old man with xanthomas at Achilles tendon and premature cardiovascular disease, with a first degree relative who suffered a premature myocardial infartion. He was clinically diagnosed as having FH with a MedPed score of 16 points. Plasma lipid levels before treatment were: TC (480 mg/dL), LDLc (416 mg/dL), TG (95 mg/dL and HDLc 36 mg/dL.

Example 8

Identification of Mutations Located in Exon 8 of the LDLr Gene

A 220 bp fragment of exon 8 of the LDLr gene was amplified by polymerase chain reaction (PCR) using the following primers: Ex8F (SEQ ID NO:148) and Ex8R (SEQ ID NO: 149).

DNA (500 ng) was amplified in a 50 µL reaction mixture containing 20 mM Tris-HCl, pH 8.4, 50 mM KCl, 1.5 mM $MgCL_2$, 200 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 64° C. for 1 min, and elongation at 72° C. for 2 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

1186+5 G>A Mutation Analysis

This mutation (1186+5 G>A) was characterized by automatic sequencing of the 220 bp fragment from exon 8 during screening for mutations in the LDL-r gene in subjects clinically diagnosed as FH. The sequencing reaction was performed in a PE Gene Amp System 9700 thermocyclator using the reagents of the kit CEQ 2000 Dye Terminator Cycle Sequencing with Beckman Quick Start (Beckman Coulter, Palo Alto, Calif., USA) and the primers Ex8BF (SEQ ID NO:148) and Ex8BR (SEQ ID NO:149).

The fragments generated by the sequencing reaction were analysed in a automatic sequencer CEQ 2000XL DNA Beckman Analysis System. The G>A change was confirmed by sequencing a second PCR product of the same sample. Alternatively, this mutation could be analyzed with the device described ("biochip") by spotting onto the slide the oligonucleotides: SEQ ID NO: 188, SEQ ID NO: 189, SEQ ID NO: 190 y SEQ ID NO: 191.

This mutation was identified in two unrelated families with autosomal dominant hipecholesterolemia. The index case of one of these families was a 34 years old woman with xantelasmas, arcus corneae, tendon xanthomata and family history of hypercholesterolemia. She was clinically diagnosed as having FH with a MedPed score of 21 points. Plasma lipid levels before treatment were: TC 411 mg/dL, LDL-c 346 mg/dL and normal TG and HDL-c levels. Lipid lowering treatment with cerivastatin (0.2 mg/day) reduced her LDL-c to 222 mg/dL.

Example 9

Identification of Mutations Located in Exon 9 of the LDLr Gene

A 224 bp fragment of exon 9 of the LDLr gene was amplified by polymerase chain reaction (PCR) using the following primers: Ex9F (SEQ ID NO: 20) and Ex9R (SEQ ID NO: 21).

DNA (500 ng) was amplified in a 50 µL reaction mixture containing 20 mM Tris-HCl, pH 8.4, 50 mM KCl, 1.5 mM $MgCL_2$, 200 µM each dNTP, 0.2 µM of each primer and 1.5 units of Taq DNA polymerase (Gibco BRL, Carlsbad, Calif., USA). The amplification cycles were: 10 min of denaturation at 96° C., followed by 35 cycles of denaturation at 94° C. for 1 min, annealing at 63° C. for 1 min, and elongation at 72° C. for 2 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

1197del9 Mutation Analysis

This mutation was analyzed by heteroduplex analysis; the electrophoresis in 8% polyacrilamide gel of PCR products visualized by staining with ethidium bromide, showed the presence of heteroduplexes bands instead of the corresponding normal and mutated homoduplexes. The fragments obtained had a length of 224 bp for normal alleles and 215 bp for mutant alleles. The heteroduplex band migrated more slowly because of the formation of the bubble between the michtmached sequences. Alternatively, this mutation could be analyzed with the device described ("biochip") by spotting onto the slide the oligonucleotides SEQ ID NO: 100, SEQ ID NO: 101, SEQ ID NO: 102 y SEQ ID NO: 103.

1197del9 mutation was detected in eight unrelated families having the characteristic in common of having an autosomal dominant familial hypercholesterolemia. Index case of one of these families was a 45 years old woman, with xanthomata who suffered an angine pectoris at the age of 41. Her father suffered a myocardial infarction at the age of 36. She was clinically diagnosed as having FH with a MedPed score of 18 points. Plasma lipid levels before treatment were: TC (525 mg/dL), LDLc (443 mg/dL), TG (163 mg/dL) and HDLc (49 mg/dL). Lipid lowering treatment with atorvastatin (20 mg/day) reduced her LDL-c to 323 mg/dL.

Y379X Mutation Analysis

This mutation Y379X (1200C>A, TAC>TAA, Tyr379Stop) destroy a cleavage site for the restriction endonuclease MnlI. Fifteen µL of PCR sample were digested with 15 units of MnlI in a total volume of 30 µL according to the protocol described by the manufacturer (Gibco BRL, Carlbad, Calif. USA). The fragments obtained had a length of 87, 56, 34, 22, 18, 4, and 3 bp for normal alleles and 87, 56, 38, 22, 18, and 3 bp for mutant alleles. These fragments were electrophoresed in 16% polyacrilamide (PAA) gel and in this way it was possible to distinguish the 34 and 38 bp bands which differentiate both alleles by staining with ethidium bromide. Alternatively, this mutation could be analyzed with the device described ("biochip") by spotting onto the slide the oligonucleotides SEQ ID NO: 104, SEQ ID NO: 105, SEQ ID NO: 106 y SEQ ID NO: 107.

Y379X mutation was detected in a family with autosomal dominant hypercholesterolemia. The subject from such family was a 69 years old man. His father had died of a myocardial infartion at age 50 and had two children with total plasmatic cholesterol above the 95 percentile. He was clinically diagnosed as having FH with a MedPed score of 7 points. A lipid determination without treatment gave us the following results: TC (381 mg/dL) and LDLc (306 mg/dL) with normal TG and HDLc levels. Lipid lowering treatment with atorvastatin (20 mg/day) reduced his LDL-c to 259 mg/dL 1207delT Mutation Analysis This mutation destroys a cleavage site for the restriction enzyme MboII. Fifteen µL of amplified material of exon 9 were digested with 15 units of MboII in a total volume of 30 µL according to the protocol described by the manufacturer (Amersham Pharmacia Biotech Inc., Piscataway, N.J., USA). The fragments obtained had a length of 140, 46, 35, and 3 bp for normal alleles and 140, 48, and 35 bp for mutant alleles. These fragments were electrophoresed in 16% polyacrilamide gel and by staining with ethidium bromide the 46 and 48 bp bands could be distinguished, which differentiate both alleles. Alternatively, this mutation could be analyzed with the device described ("biochip") by spotting onto the slide the oligonucleotides SEQ ID NO: 108, SEQ ID NO: 109, SEQ ID NO: 110 y SEQ ID NO: 111.

1207delT mutation was detected in a member of family with autosomal dominant hypercholesterolemia. The subject was a 35 years old woman. The MedPed score for FH clinical diagnostic was 9 points. The Plasma lipid levels without lipid lowering treatment were: TC (429 mg/dL), LDLc (345 mg/dL), TG (188 mg/dL) and HDLc (46 mg/dL). Combined lipid lowering treatment with simvastatin (40 mg/day) and colestipol (5 g/day) reduced her TC and LDL-c to 220 mg/dL and 137 mg/dL without significant changes in her TG and HDL-c levels.

Y421X Mutation Analysis

This mutation Y421X (1326C>G, TAC>TAG, Tyr421Stop) creates a new cleavage site for the endonuclease BfaI. Fifteen µL of PCR sample were digested with 15 units of BfaI in a total volume of 30 µL according to the protocol described by the manufacturer (NEB, Beverly, Mass., USA). The fragments obtained had a length of 224 bp (fragment without digestion) for normal alleles and 164 and 60 bp for mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides SEQ ID NO: 112, SEQ ID NO: 113, SEQ ID NO: 114 y SEQ ID NO: 115.

Y421X mutation was detected in three unrelated families having in common autosomal deominant familial hipercholesterolemia. The index case of one of these families was a 71 years old woman, with arcus corneae, tendon xanthomas and xantelasmas. Her father had suffered a myocardial infarction at the age of 51 and had a son with marked hypercholesterolemia (TC 367 mg/dL). She was clinically diagnosed as having FH with a MedPed score of 16 points. The plasmatic concentrations of lipids without the use of lipid lowering drugs were: TC (615 mg/dL) and LDLc (550 mg/dL) with normal TG and HDLc levels.

1204insT Mutation Analysis

This mutation destroys a cleavage site for the endonuclease MboII. Fifteen µL of exon 9 PCR sample were digested with 15 units of MboII in a total volume of 30 µL according to the protocol described by the manufacturer (Amersham Pharmacia, NJ, USA). The fragments obtained had a length of 141, 45, 35 and 3 bp in normal alleles and 141, 45 and 39 pb in mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides SEQ ID NO: 168, SEQ ID NO: 169, SEQ ID NO: 170 y SEQ ID NO: 171

This mutation was detected in a girl 12 years old. Her father and 7 years old brother had hypercholesterolemia with TC levels of 412 and 321 mg/dL respectively. The MedPed score for FH clinical diagnostic was 9 points. Analysis of her fasting serum lipid levels without the use of lipid lowering drugs were TC 332 mg/dL, LDL-c 267 mg/dL with normal TG and HDL-c levels. Lipid lowering treatment with resins (15 g/day) reduced the LDL-c levels to 248 mg/dL.

Example 10

Identification of Mutations Located in Exon 10 of the LDLr Gene

A 278 bp fragment of exon 10 of the LDLr gene was amplified by polymerase chain reaction (PCR) using the following primers: Ex10F (SEQ ID NO: 22) and Ex10R (SEQ ID NO: 23

DNA (500 ng) was amplified in a 50 µL reaction mixture containing 20 mM Tris-HCl, pH 8.4, 50 mM KCl, 1.5 mM $MgCL_2$, 200 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 58° C. for 1 min, and elongation at 74° C. for 2 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

1432delG Mutation Analysis

As this mutation does not change the restriction map, a mismatched desoxyoligonucleotide was designed and synthetized to introduce the recognition site for the NaeI restriction enzyme in presence of the mutant allele that disappears in the presence of normal allele.

A 200 bp fragment of exon 10 of the LDLr gene was amplified by polymerase chain reaction (PCR) using the following primers: Ex10R (SEQ ID NO: 23) and Mut1432delGF (SEQ ID NO: 24).

DNA (500 ng) was amplified in a 50 µL reaction mixture containing 20 mM Tris-HCl, pH 8.4, 50 mM KCl, 1.5 mM $MgCL_2$, 200 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 58° C. for 1 min, and elongation at 72° C. for 2 min, and a final extension of 72° C. for 10 min.

Fifteen µL of PCR sample were digested with 15 units of NaeI in a total volume of 30 µL according to the protocol described by the manufacturer (Amersham Pharmacia Biotech Inc., Piscataway, N.J., USA). The fragments obtained had a length of 200 bp (undigested fragment) for normal alleles and 179 and 20 bp in mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides SEQ ID NO: 116, SEQ ID NO: 117, SEQ ID NO: 118 and SEQ ID NO: 119.

1432delG mutation was detected in a family with autosomal dominant hypercholesterolemia. The subject was a 53 years old woman with tendon xanthomas who had suffered a myocardial infartion, moreover with a family history of premature cardiovascular disease. She was clinically diagnosed as having FH with a MedPed score of 15 points. An lipid analysis without use lipid lowering therapy gave us the following results: TC (548 mg/dL) and LDLc (470 mg/dL) with normal TG and HDLc levels.

T433N Mutation Analysis

This mutation T433N (1361C>A, ACC>AAC, Tyr433Asn) was characterized by automatic sequencing of the 278 bp fragment from exon 10 of the LDL-r gene on analysing this fragment in subjects clinically diagnosed as having FH. The sequencing reaction was developed in the thermocycler PE Gene Amp System 9700 using the reagents of the kit CEQ 2000 Dye Terminator Cycle Sequencing with Beckman Quick Start (Beckman Coulter, Palo Alto, Calif., USA) and the primers Ex10F (SEQ ID NO: 22) and Ex10R (SEQ ID NO: 23). The fragments generated by the sequencing reaction were analysed in an automatic sequencer CEQ 2000XL DNA Beckman Analysis System. The C>A change was confirmed by sequencing a second PCR product from the same sample. Alternatively, this mutation could be analyzed with the device described ("biochip") by spotting onto the slide the oligonucleotides: SEQ ID NO: 156, SEQ ID NO: 157, SEQ ID NO: 158 and SEQ ID NO: 159.

T433N mutation was detected in a 50 years old man with arcus corneae and family history of autosomal dominant hypercholesterolemia and daughter 21 years old with TC levels of 310 mg/dL. The MedPed score for FH clinical diagnostic was 6 points. Analysis of his plasmatic lipip concentrations before beginning pharmalogical treatment were TC 318 mg/dl, LDL-c 249 mg/dL with normal TG and HDL-c. Lipid lowering therapy with lovastatin (20 mg/day) reduced his LDL-c to 199 mg/dL Analysis of the Mutation T446I This mutation T446I (1400C>T, ACC>ATC, Tyr446Ile) was characterized by automatic sequencing of the 278 bp fragment from exon 10 of the LDL-r gene in subjects clinically diagnosed as having FH. The sequencing reaction was performed in a thermocycler PE Gene Amp System 9700 using the reagents of the kit CEQ 2000 Dye Terminator Cycle Sequencing with Quick Start (Beckman Coulter, Palo Alto, Calif., USA) and the primers Ex10F (SEQ ID NO: 22) and Ex (SEQ ID NO: 23). The fragments generated by the sequencing reaction were analysed in an automatic sequencer CEQ 2000XL DNA Beckman Analysis System. The C>T change was confirmed by sequencing a second PCR product from the same sample. Alternatively, this mutation could be analyzed with the device described ("biochip") by spotting onto the slide the oligonucleotides: SEQ ID NO: 204, SEQ ID NO: 205, SEQ ID NO: 206 and SEQ ID NO: 207.

T446I mutation was detected in a 64 years old woman with a background of premature cardiovascular disease (an angor at 62 years of age) and with two brothers with hypercholesterolemia who been suffered a myocardial infarction at 40 and 46 years of age respectively. She was diagnosed clinically as having FH with a MedPed score of 9 points. The plasmatic concentrations of lipids under pharmalogical treatment with pravastatin were: TC (352 mg/dL) and LDLc (281 mg/dL) with normal TG and HDLc levels. After lipid lowering treatment with simvastatin 20 mg/day the LDL-c levels decreased to 150 mg/dL.

insA Analysis Mutant 1423delGC/insA

This mutation 1423delGC/insA destroys a cleavage site for the endonuclease MvaI. Fifteen µL of exon 10 PCR product were digested with 15 units of MvaI in a total volume of 30 µL according to the protocol described by the manufacturer (Fermentas Inc., Henover, Md., USA). The fragments obtained had a length of 150 and 128 bp for normal alleles and 128, 87 and 63 bp for mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides SEQ ID NO: 164, SEQ ID NO: 165, SEQ ID NO: 166 y SEQ ID NO: 167.

This mutation was detected in a 34 years old man with parental history of hypercholesterolemia. The MedPed score for FH clinical diagnosis was 9 points. The plasmatic lipid concentrations prior to pharmalogical treatment were: Analysis of her fasting serum lipid levels without the use of lipid lowering drugs were: Total TC 554 mg/dL, LDL-c 422 mg/dL with normal TG and HDL-c levels. Lipid lowering treatment with atorvastatin (10 g/day) lowered his LDL-c levels to 406 mg/dL.

Example 11

Identification of Mutations Located in Exon 11 of the LDLr Gene

A 194 bp fragment of exon 11 of the LDLr gene was amplified by polymerase chain reaction (PCR) using the following primers: Ex11F (SEQ ID NO: 25) y Ex11R (SEQ ID NO: 26).

DNA (500 ng) was amplified in a 50 µL reaction mixture containing 20 mM Tris-HCl, pH 8.4, 50 mM KCl, 1.5 mM $MgCL_2$, 200 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 65° C. for 1 min, and elongation at 72° C. for 2 mM, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of a mutation identified by sequencing was then analysed by restriction analysis and by the device described previously "biochip".

W515X Mutation Analysis

This mutation W515X (1607G>A, TGG>TAG, Trp515Stop) creates a new BfaI digestion site. Fifteen μL of PCR sample were digested with 15 units of BfaI in a total volume of 30 μL according to the protocol described by the manufacturer (NEB, Beverly, Mass., USA). The fragments obtained had a length of 164 and 30 bp for normal alleles and 97, 67 and 30 bp for mutant alleles. These fragments were electrophoresed in 3% NuSieve agarose gel and were visualized by staining with ethidium bromide. Alternatively, this mutation could be analyzed with the device described ("biochip") by spotting onto the slide the oligonucleotides: SEQ ID NO: 120, SEQ ID NO: 121, SEQ ID NO: 122 and SEQ ID NO: 123.

W515X mutation was detected in a 39 years old man, with arcus corneae whose father had suffered a myocardial infarction at age 50. He has been diagnosed as having familial hypercholesterolemia with a MedPed diagnostic score of 13 points. The plasmatic lipid concentrations without pharmacological treatment were: TC (364 mg/dL) and LDLc (308 mg/dL) with normal TG and HDLc levels. The subject's father, two brothers and a son had cholesterol levels above the 95 percentile.

Analysis of the Mutation [1587-5del5; 1587del31]

This mutation [1587-5del5; 1587del31] was identified by automatic sequencing of the 194 pb fragment from exon 11 of the LDL-r gene on analysing this fragment in subjects clinically diagnosed as having FH. The sequencing reaction was performed in a thermocycler PE Gene Amp System 9700 using the kit CEQ 2000 Dye Terminator Cycle Sequencing with Quick Start (Beckman Coulter, Palo Alto, Calif., USA) and the primers (SEQ ID NO: 25) y Ex11R (SEQ ID NO: 26).

The fragments generated by the sequencing reaction were analysed in an automatic sequencer CEQ 2000XL DNA Beckman Analysis System. This deletion was confirmed by electrophoresis in 2% agarose gel after which bands of 194 and 258 bp could be observed corresponding to the normal allele and mutated allele respectively. Alternatively, this mutation could be analyzed with the device described ("biochip") by spotting onto the slide the oligonucleotides: SEQ ID NO: 256, SEQ ID NO: 257, SEQ ID NO: 258 and SEQ ID NO: 259.

[1587-5del5; 1587del31] mutation was detected in a 43 years man with arcus corneae and family history of autosomal dominant hypercholesterolemia (father and son with hypercholesterolemia) and evidence of cardiovascular disease in the family (his father suffered a myocardial infartion at age 50). He was diagnosed clinically as having FH with a MedPed score of 9 points. The plasmatic lipid concentrations before pharmacology treatment were: TC (345 mg/dL) and TG (160 mg/dL) and HDLc (34 mg/dL). After combined lipid lowering treatment with simvastatin 40 mg/day and colestipol 10 g/day the LDL-c levels decreased to 208 mg/dL.

Analysis of the g516x Mutation
G516X Mutation Analysis

This mutation (1609G>T, GGA>TGA, Gly516Stop) creates a new HphI digestion site. Fifteen L of amplified material of exon 11 were digested with 15 units of HphI in a total volume of 30 μL according to the protocol described by the manufacturer (NEB, Beverly, Mass., USA). The fragments obtained had a length 139, 43 and 12 bp for normal alleles and 81, 58, 43 y 12 p,bp for mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides: SEQ ID NO: 176, SEQ ID NO: 177, SEQ ID NO: 178 and SEQ ID NO: 179

G516X mutation was detected in a 20 years old woman, with tendon xanthomas and family history of hipercholesterolemia (mother and two adolescent brothers with LDL-c levels above the 95 percentile). She has been diagnosed as having familial hypercholesterolemia with a MedPed diagnostic score of 17 points. The plasmatic lipid concentrations prior to pharmacological treatment were: TC 476 mg/dL, LDL-c 403 mg/dl and normal TG and HDL-c levels. After lipid lowering treatment with an HMGCoA reductase inhibitor the LDL-c levels decreased to 202 mg/dL H562Q Mutation Analysis This mutation (1749C>A, CAC>CAA, His562Gln) was identified by automatic sequencing of the 194 pb fragment from exon 11 of the LDL-r gene on analysing this fragment in patients clinically diagnosed as having FH. The sequencing reaction was performed in a thermocycler PE Gene Amp System 9700 using the kit CEQ 2000 Dye Terminator Cycle Sequencing with Quick Start (Beckman Coulter, Palo Alto, Calif., USA) and the primers (SEQ ID NO: 25) y Ex11R (SEQ ID NO: 26). The fragments generated by the sequencing reaction were analysed in an automatic sequencer CEQ 2000XL DNA Beckman Analysis System. The change observed C>A was confirmed by automatic sequencing of a second PCR product of the same sample. Alternatively, this mutation can be analysed with the device described ("biochip") by spotting onto the slide the oligonucleotides: SEQ ID NO: 208, SEQ ID NO: 209, SEQ ID NO: 210 and SEQ ID NO: 211.

H562Q mutation was detected in a 37 years woman with family history of autosomal dominant hypercholesterolemia, (father with hypercholesterolemia and suffered a myocardial infartion at age of 48 and her son at age 13 with TC level of 500 mg/dL). She was diagnosed clinically as having FH with a MedPed score of 9 points. The plasmatic lipid concentrations before pharmacological treatment were: TC (350 mg/dL) with normal TG and HDLc levels. After lipid lowering treatment with atorvastatin 20 mg/day the TC level lowered to 333 mg/dL.

Example 12

Identification of Mutations Located in Exon 12 of the LDLr Gene

A 236 bp fragment of exon 12 was amplified by polymerase chain reaction (PCR) using the following primers: Ex12F (SEQ ID NO: 150) and Ex12R (SEQ ID NO: 151).

DNA (500 ng) was amplified in a 50 μL reaction mixture containing 20 mM Tris-HCl, pH 8.4, 50 mM KCl, 1.5 mM $MgCL_2$, 200 μM each dNTP, 0.2 μM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 58° C. for 1 min, and elongation at 72° C. for 2 min, and a final extension of 72° C. for 10 min.

The PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously ("biochip").

E579D Mutation Analysis

This mutation E579D (1800G>C, GAG>GAC, Glu579Asp)) was identified by automatic sequencing of 236 bp fragment from exon 12 of the LDL-r gene on analyzing this fragment in patients clinically diagnosed as having FH. The sequencing reaction was performed in a thermocycler PE Gene Amp System 9700 using the kit CEQ 2000 Dye Terminator Cycle Sequencing with Quick Start (Beckman Coulter, Palo Alto, Calif., USA) and the primers Ex12F (SEQ ID NO: 150) and Ex12R (SEQ ID NO:151). The fragments generated by the sequencing reaction were analysed in an automatic sequencer CEQ 2000XL DNA Beckman Analysis System. The change observed G>C was confirmed by automatic sequencing of a second PCR product of the same sample. Alternatively, this mutation can be analysed with the device described ("biochip") by spotting onto the slide the oligonucleotides: SEQ ID NO: 224, SEQ ID NO: 225, SEQ ID NO: 226 and SEQ ID NO: 227.

E579D mutation was detected in a 49 years old man with family history of autosomal dominant hypercholesterolemia (ather with TC 450 mg/dL and his brother and two adolescent children with LDL-c levels 95 percentile). He was diagnosed clinically as having FH with a MedPed score of 8 points. Analysis of his plasmatic lipid concentrations prior to pharmacological treatment were: TC (320 mg/dL), LDL-c (250 mg/dL) with normal TG and HDL-c levels. After lipid lowering treatment with atorvastatin (10 mg/day) the LDL-c level lowered to 187 mg/dL.

1815del11 Mutation Analysis

This mutation was able to be identified by heteroduplexes analysis. The electrophoresis in 8% polyacrilamide (PAA) gel of exon 12 PCR amplified material when mutation exists showing the presence of heteroduplex bands of an apparent greater molecular size than the two homoduplex bands of 236 and 225 bp, readily distinguished in the gel following staining with ethidium bromide. The two bands of the heteroduplexes that form migrate at a slower speed as a result of the formation of bubbles between the mismatched sequences. Alternatively, this mutation could be analyzed with the device described ("biochip") by spotting onto the slide the oligonucleotides SEQ ID NO: 184, SEQ ID NO: 185, SEQ ID NO: 186 y SEQ ID NO: 187.

1815del11 mutation was identified in four unrelated families with autosomal dominant familial hypercholesterolemia. The index case of one of these families was a 69 years old woman with arcus cornealis, evidence of premature coronary artery disease (angor at 56 years) and history of hypercholesterolemia in several family embers (two brothers with TC 700 and 435 mg/dL respectively). She was clinically diagnosed as having FH with a MedPed score of 13 points. Plasma lipid levels with lipid lowering treatment with simvastatin (40 mg/dL) were: TC 444 mg/dL, LDL-c 368 mg/dL and normal TG and HDL-c levels. After lipid lowering treatment with atorvastatin (30 mg/day) reduced her LDL-c to 225 mg/dL.

Example 13

Identification of Mutations Located in Exon 13 of the LDLr Gene

A 215 bp fragment of exon 13 of the LDLr gene was amplified by polymerase chain reaction (PCR) using the following primers: Ex13F (SEQ ID NO: 27) y Ex13R (SEQ ID NO: 28

DNA (500 ng) was amplified in a 50 µL reaction mixture containing 20 mM Tris-HCl, pH 8.4, 50 mM KCl, 1 mM MgCL$_2$, 200 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 59° C. for 1 min, and elongation at 74° C. for 3 min, and a final extension of 72° C. for 10 min PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

D630N Mutation Analysis

This mutation D630N (1951G>A, GAT>AAT, Asp630Asn) destroy a MnlI digestion site. Fifteen µL of PCR sample were digested with 15 units of MnlI in a total volume of 30 µL according to the protocol described by the manufacturer (Fermentas Inc., Hanover, Md., USA). The fragments obtained had a length of 89, 48, 39, 14+14, 12 and 11 bp in normal alleles and 89, 59, 39, 14+14 and 12 bp in mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides: SEQ ID NO: 124, SEQ ID NO: 125, SEQ ID NO: 126 y SEQ ID NO: 127

D630N mutation was detected in two unrelated families with autosomal dominant heredity. Index case of one of this family was a 36 years old woman whose parents died of myocardial infartion at 62 and 64 years of age. The MedPed score for FH clinical diagnostic was 7 points. The plasmatic lipid concentrations without pharmalogical treatment were: TC (332 mg/dL) and LDLc (268 mg/dL), TG (81 mg/dL) and HDLc (48 mg/dL).

H635N Mutation Analysis

As this mutation H635N (1966C>A, CAC>AAC, His635Asn) does not change the restriction map, a desoxyoligonucleotide with two mismatches was designed and synthetized to introduce the recognition site of CaiI in presence of the normal allele and disappearing in the presence of the mutant allele.

A 169 bp fragment of exon 13 was amplified the PCR technique using the desoxyoligonucleotide Ex13F (SEQ ID NO: 27) and the desoxyoligonucleotide with two mismatches MutH635NR (SEQ ID NO: 26).

DNA (500 ng) was amplified in a 50 µL reaction mixture containing 20 mM Tris-HCl, pH 8.4, 50 mM KCl, 1.5 mM MgCL$_2$, 200 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 56° C. for 1 min, and elongation at 72° C. for 1 min, and a final extension of 72° C. for 10 min.

Fifteen µL of PCR sample were digested with 15 units of CaiI in a total volume of 30 µL according to the protocol described by the manufacturer (Fermentas Inc., Hanover, Md., USA). The fragments obtained had a length of 151 and 18 bp in normal alleles and 169 bp in mutant alleles. These fragments were electrophoresed in 8% PAA gel and were visualized by staining with ethidium bromide. Alternatively, this mutation could be analyzed with the device described ("biochip") by spotting onto the slide the oligonucleotides: SEQ ID NO: 128, SEQ ID NO: 129, SEQ ID NO: 130 y SEQ ID NO: 131

H635N mutation was detected in a member of autosomal dominant hypercholesterolemia family. The subject was a 43 years old man with arcus corneae and without a premature cardiovascular disease family history. His mother and three siblings had cholesterol concentrations above the 95 percentile. He was clinically diagnosed as having FH with a MedPed score of 13 points. His plasmatic lipid concentrations without pharmacological treatment were: TC (448 mg/dL) and LDLc (384 mg/dL) with normal TG and HDLc levels.

Example 14

Identification of Mutations Located in Exon 14 of the LDLr Gene

A 288 bp fragment of exon 14 of the LDLr gene was amplified by polymerase chain reaction (PCR) using the desoxyoligonucleotides Ex14F (SEQ ID NO: 30) and Ex14R (SEQ ID NO: 31).

DNA (250 ng) was amplified in a 50 µL reaction mixture containing 20 mM Tris-HCl, pH 8.4, 50 mM KCl, 1.5 mM MgCL$_2$, 20 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 59° C. for 1 min, and elongation at 72° C. for 2 min, and a final extension of 72° C. for 10 min PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

D686Y Mutation Analysis

This mutation D686Y (2119G>T, GAC>TAC, Asp686Tyr) was identified by automatic of 288 bp fragment from exon 14 of the LDL-r gene on analyzing this fragment in subjects clinically diagnosed as having FH. The sequencing reaction was performed in a thermocycler PE Gene Amp System 9700 using the kit CEQ 2000 Dye Terminator Cycle Sequencing with Quick Start (Beckman Coulter, Palo Alto, Calif., USA) and the primers Ex14F (SEQ ID NO: 30) and Ex14R (SEQ ID NO: 31).

The fragments generated by the sequencing reaction were analysed in an automatic sequencer CEQ 2000XL DNA Beckman Analysis System. The change observed G>T was confirmed by automatic sequencing of a second PCR product of the same sample. Alternatively, this mutation can be analysed with the device described ("biochip") by spotting onto the slide the oligonucleotides: SEQ ID NO: 216, SEQ ID NO: 217, SEQ ID NO: 218 and SEQ ID NO: 219. 30) y Ex 14R (SEQ ID NO:

D686Y mutation was detected in a 31 years old man with xantomas, arcus corneae, evidence of premature coronary artery disease (angor) and family history of hypercholesterolemia. He was diagnosed clinically as having FH with a MedPed score of 21 points. His plasmatic lipid concentrations prior to pharmacology treatment were: TC (430 mg/dL) with normal TG and HDLc levels. After combined lipid lowering treatment with atorvastatin 40 mg/day and colestipol 5 (g/day) the TC level decreased to 205 mg/dL.

Example 15

Identification of Mutations Located in Exon 15 of the LDLr Gene

A 243 bp fragment of exon 15 of the LDLr gene was amplified by polymerase chain reaction (PCR) using the desoxyolygonucleotides Ex 15F (SEQ ID NO: 32) and Ex15R (SEQ ID NO: 33).

DNA (500 ng) was amplified in a 50 µL reaction mixture containing 20 mM Tris-HCl, pH 8.4, 50 mM KCl, 1.5 mM MgCL$_2$, 20 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 55° C. for 30 seconds, and elongation at 72° C. for 1.5 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip".

2184delG Mutation Analysis

This mutation creates a new cleavage for the restriction enzyme for AluI. Fifteen µL of PCR sample were digested with 15 units of AluI in a total volume of 30 µL according to the protocol described by the manufacturer (Gibco BRL, Carlsbad, Calif., USA). The fragments obtained had a length of 166 and 78 bp for normal alleles and 166, 67 and 11 bp for mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides: SEQ ID NO: 132, SEQ ID NO: 133, SEQ ID NO: 134 y SEQ ID NO: 135

2184delC mutation was detected in an autosomal dominant hypercholesterolemia family. The subject was a 32 years old woman, with family history of premature cardiovascular disease. The MedPed score for FH clinical diagnostic was 6 points. The plasmatic lipid concentrations without pharmacological treatment were: TC (330 mg/dL) and LDLc (270 mg/dL) with normal TG and HDLc levels.

Analysis of the T740M Mutation

This mutation T740M (2282C>T, ACG>ATG, Tyr740Met) creates a new NlaIII digestion site. Fifteen µL of PCR sample were digested with 15 units of NlaIII in a total volume of 30 µL according to the protocol described by the manufacturer (NEB, Beverly, Mass., USA). The fragments obtained had a length 247 pb for normal alleles and 274, 194 y 53 bp for mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides: SEQ ID NO: 192, SEQ ID NO: 193, SEQ ID NO: 194 and SEQ ID NO: 195.

T740M mutation was detected in a 60 years old woman, with arcus corneae, family history of hypercholesterolemia and family history of premature cardiovascular disease. Father died at 34 years with cerebrovascular incident. She has been diagnosed as having familial hypercholesterolemia with a MedPed diagnostic score of 10 points. The plasmatic lipid concentrations prior to pharmacology treatment were: TC 492 mg/dL and normal TG and HDL-c levels. After lipid lowering treatment with atorvastatin the TC level lowered to 251 mg/dL Example 16

Identification of Mutations Located in Exon 16 of the LDLr Gene

A 273 bp fragment of exon 16 was amplified by polymerase chain reaction (PCR) using the following primers: Ex 16F (SEQ ID NO: 152) and Ex 16R (SEQ ID NO: 153).

DNA (500 ng) was amplified in a 50 µL reaction mixture containing 20 mM Tris-HCl, pH 8.4, 50 mM KCl, 1.5 mM MgCL$_2$, 20 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 63° C. for 1 min, and elongation at 72° C. for 2 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip V766E Mutation Analysis This mutation V766E (2360T>A, GTG>GAG, Val766Glu) was identified by automatic sequencing of the 273 pb fragment from exon 16 of the LDL-r gene on analyzing this fragment in patients clinically diagnosed as having FH. The sequencing reaction was performed in a thermocycler PE Gene Amp System 9700 using the kit CEQ 2000 Dye Terminator Cycle Sequencing with Beckman Quick Start (Beckman Coulter, Palo Alto, Calif., USA) and the primers Ex 16F (SEQ ID NO: 152) y EX16R (SEQ ID NO: 153). The fragments generated by the sequencing reaction were analyzed in an automatic sequencer CEQ 2000XL DNA Beckman Analysis System. The change T>A change observed was confirmed by sequencing a second PCR product. Alternatively, this mutation could be analyzed with the device described ("biochip") by spotting onto the slide the oligonucleotides: SEQ ID NO: 236, SEQ ID NO: 237, SEQ ID NO: 238 y SEQ ID NO: 239.

D686Y mutation was detected in a 58 years old woman with tendon xantomas in elbows, arcus corneae, xantelasmas and family history of hypercholesterolemia. She was diagnosed clinically as having FH with a MedPed score of 12 points. The plasmatic lipid concentration prior to pharmacological treatment were: TC (420 mg/dL), LDL-c (324 mg/dL) with normal TG and HDLc levels.

I771T Mutation Analysis

As this mutation I771T (2375T>C, ATT>CACT, Ile771Thr), does not change the restriction map, a mismatched desoxyoligonucleotide was designed and synthetized to introduce the recognition site of HincII in presence of the mutant allele and disappearing in the presence of normal allele.

A 142 bp fragment of exon 16 of the LDLr gene was amplified by the PCR technique using desoxyoligonucleotide Ex16R (SEQ ID NO: 153) and the mismatched desoxyoligonucleotide MutI771TF (SEQ ID NO: 154).

DNA (500 ng) was amplified in a 50 µL reaction mixture containing 20 mM Tris-HCl, pH 8.4, 50 mM KCl, 1.5 mM MgCL$_2$, 200 µM each dNTP, 0.2 µM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 61° C. for 1 min, and elongation at 72° C. for 2 min, and a final extension of 72° C. for 10 min.

Fifteen µL of PCR sample were digested with 15 units of HincII in a total volume of 30 µL according to the protocol described by the manufacturer (Amersham Pharmacia Biotech Inc., Piscataway, N.J., USA). The fragments obtained had a length of 142 bp in normal alleles and 121 and 21 bp in mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides SEQ ID NO: 196, SEQ ID NO: 197, SEQ ID NO: 198 y SEQ ID NO: 199.

I771T mutation was detected in a 60 years old woman with evidence of premature coronary disease in the family and hypercholesterolemia family history. She has been diagnosed as having familial hypercholesterolemia with a MedPed diagnostic score of 21 points. Her plasma lipid levels were: TC (422 mg/dL) and LDLc (368 mg/dL), and normal TG and HDLc levels 2389+3 A>C Mutation Analysis This mutation 2389+3 C>T was identified by DNA sequencing of the 273 pb fragment from exon 16 of the LDL-r gene in subjects clinically diagnosed as having FH. The sequencing reaction was performed in a thermocycler PE Gene Amp System 9700 using the kit CEQ 2000 Dye Terminator Cycle Sequencing with Quick Start (Beckman Coulter, Palo Alto, Calif., USA) and the primers Ex16F (SEQ ID NO: 152) and Ex16R (SEQ ID NO:153). The fragments generated by the sequencing reaction were analysed in an automatic sequencer CEQ 2000XL DNA Beckman Analysis System. The change observed C>T was confirmed by automatic sequencing of a second PCR product of the same sample.

Alternatively, this mutation can be analysed with the device described ("biochip") by spotting onto the slide the oligonucleotides: SEQ ID NO: 252, SEQ ID NO: 253, SEQ ID NO: 254 and SEQ ID NO: 255.

2389+3 C>T mutation was detected in a 36 years old man with aquiles heel tendon xantomas and hand extenders and history of hypercholesterolemia in the family (mother, brother and one son with LDL-c levels above the 95 percentile). He was diagnosed clinically as having FH with a MedPed score of 18 points. The plasmatic lipid concentrations before pharmacological treatment were: TC (450 mg/dL) with normal TG and HDLc levels. Lipid lowering treatment with atorvastatin (20 mg/dL) reduced his LDL-c to 259 mg/dL 2389+4 A>G Mutation Analysis As this mutation (2389+4 A>G) does not change the restriction map, a mismatched desoxyinucleotide was designed and synthetized to introduce the recognition site of BshNI in presence of the mutant allele but not in presence of normal allele.

A 194 bp fragment of exon 16 gene was amplified by polymerase chain reaction (PCR) using the following primers: Ex 16F (SEQ ID NO: 152) and the mismatched desoxyioligonucleotide Mut2389+4 A>GR (SEQ ID NO: 155).

DNA (500 ng) was amplified in a 50 µL reaction mixture containing 20 mM Tris-HCl, pH 8.4, 50 mM KCl, 1.5 mM MgCL$_2$, 200 µM each dNTP, 0.2 µM each primer and 1.5 units of Tag DNA polymerase (Gibco BRL, Carlsbad, Calif., USA). The amplification cycle was: 10 min of denaturation at 96° C., followed by 35 cycles of denaturation at 94° C. for 1 min, annealing at 61° C. for 1 min, and elongation at 72° C. for 2 min, and a final extension of 72° C. for 10 min.

Fifteen µL of PCR sample were digested with 15 units of BshNI in a total volume of 30 µL according to the protocol described by the manufacturer (Fermentas Inc., Hanover, Md., USA). The fragments obtained had a length of 194 by for normal alleles and 175 and 19 bp for mutant alleles. These fragments were electrophoresed in 8% polyacrilamide gel and were visualized by staining with ethidium bromide. Alternatively, this mutation could be analyzed with the device described ("biochip") by spotting onto the slide the oligonucleotides SEQ ID NO: 180, SEQ ID NO: 181, SEQ ID NO: 182 y SEQ ID NO: 183.

2389+4 A>G mutation was detected in 11 unrelated hypercholesterolemic families. Index case of one of this families was a 22 years old woman with tendon xanthomas and family history of premature cardiovascular disease (father with hypercholesterolemia and myocardial infartion at age 29). She has been diagnosed as having familial hypercholesterolemia with a MedPed diagnostic score of 17 points. Her plasma lipid levels without lipid lowering treatment were: TC (356 mg/dL) and LDLc (293 mg/dL), and normal TG and HDLc levels. Combined lipid lowering treatment with atorvastatin (40 mg/day) and colestipol (5 g/day) lowered her HLD-c level to 227 mg/dL Example 17

Identification of Mutations Located in Exon 17 of the LDLr Gene

A 242 bp fragment of exon 17 was amplified by polymerase chain reaction (PCR) using the following primers: Ex17F (SEQ ID NO: 34) and Ex17R (SEQ ID NO: 35).

DNA (300 ng) was amplified in a 50 μL reaction mixture containing 20 mM Tris-HCl, pH 8.4, 50 mM KCl, 1.5 mM $MgCL_2$, 200 μM each dNTP, 0.2 μM each primer and 1.5 units of Taq DNA polymerase (Gibco BRL, Carlsbad, Calif., USA). The amplification cycle was: 10 min of denaturation at 96° C., followed by 35 cycles of denaturation at 94° C. for 1 min, annealing at 58° C. for 1 min, and elongation at 72° C. for 1 min, and a final extension of 72° C. for 10 min.

PCR products were analyzed by Single Strand Conformation Polymorphisms (SSCP). Those fragments that showed abnormal SSCP patterns were sequenced using an automated CEQ 2000XL DNA Analysis System (Beckman Coulter, Palo Alto, Calif., USA). The presence of the identified mutations was subsequently determined by restriction analysis and by the device described previously "biochip
2399del5ins4 Mutation Analysis This mutation eliminate the sequence TCTTC and introduces the sequence GGGT at the 2399 position, and creates a new AvaI digestion site. Fifteen μL of PCR sample were digested with 15 units of AvaI in a total volume of 30 μL according to the protocol described by the manufacturer (Amersham Pharmacia Biotech Inc., Piscataway, N.J., USA). The fragments obtained had a length of 230 and 12 bp in normal alleles and 183, 46 and 12 bp in mutant alleles. These fragments were electrophoresed in 8% polyacrilamide gel and were visualized by staining with ethidium bromide. Alternatively, this mutation could be analyzed by the device described ("biochip") using into the slide the oligonucleotides SEQ ID NO: 136, SEQ ID NO: 137, SEQ ID NO: 138 and SEQ ID NO: 139.

2399del5ins4 mutation was detected in three unrelated hypercholesterolemic families with autosomal dominant inheritance. The index case of one of these families was a 49 years old woman, with tendon xanthomas whose father had died at 51 with myocardial infartion. The MedPed score for FH clinical diagnostic was 16 points. Her plasma lipid levels before lipid lowering treatment were: TC (510 mg/dL, LDLc (424 mg/dL).), HDLc (58 mg/dL) and TG(140 mg/dL). Combined treatment with simvastatin 20 mg/day and colestipol 20 g/day lowered her TC to 280 mg/dL. Furthermore, two children of hers, aged 22 and 20 years, had cholesterol levels of 330 and 386 mg/dL respectively.
2544insC Mutation Analysis This mutation was identified by automatic sequencing of the 242 pb fragment from exon 17 of the LDL-r gene on analyzing this fragment in subjects clinically diagnosed as having FH. The sequencing reaction was performed in a thermocycler PE Gene Amp System 9700 using the kit CEQ 2000 Dye Terminator Cycle Sequencing with Quick Start (Beckman Coulter, Palo Alto, Calif., USA) and the primers Ex 17F (SEQ ID NO: 34) and Ex 17R (SEQ ID NO: 35), the subsequent electrophoresis in automatic sequencer CEQ 2000 DNA Beckman Analysis System. This deletion was confirmed by automatic sequencing of a second PCR product from the same sample.

Alternatively, this mutation can be analysed with the device described ("biochip") by spotting onto the slide the oligonucleotides: SEQ ID NO: 244, SEQ ID NO: 245, SEQ ID NO: 246 and SEQ ID NO 247.

2544insC mutation was detected in a 37 years old man who had suffered a myocardial infartion and with tendon xanthomas, arcus corneae, family history of hypercholesterolemia (his father died prematurely of myocardial infartion). He was diagnosed clinically as having FH with a MedPed score of 21 points. The plasmatic lipid concentrations prior to pharmacology treatment were: TC (444 mg/dL), LDL-c (379 mg/dL) with normal TG and HDLc levels. Lipid lowering treatment with atorvastatin (40 mg/dL) lowered his LDL-c to 282 mg/dL

SEQUENCE LISTING

<160> NUMBER OF SEQ ID NOS: 260

Figure 1:
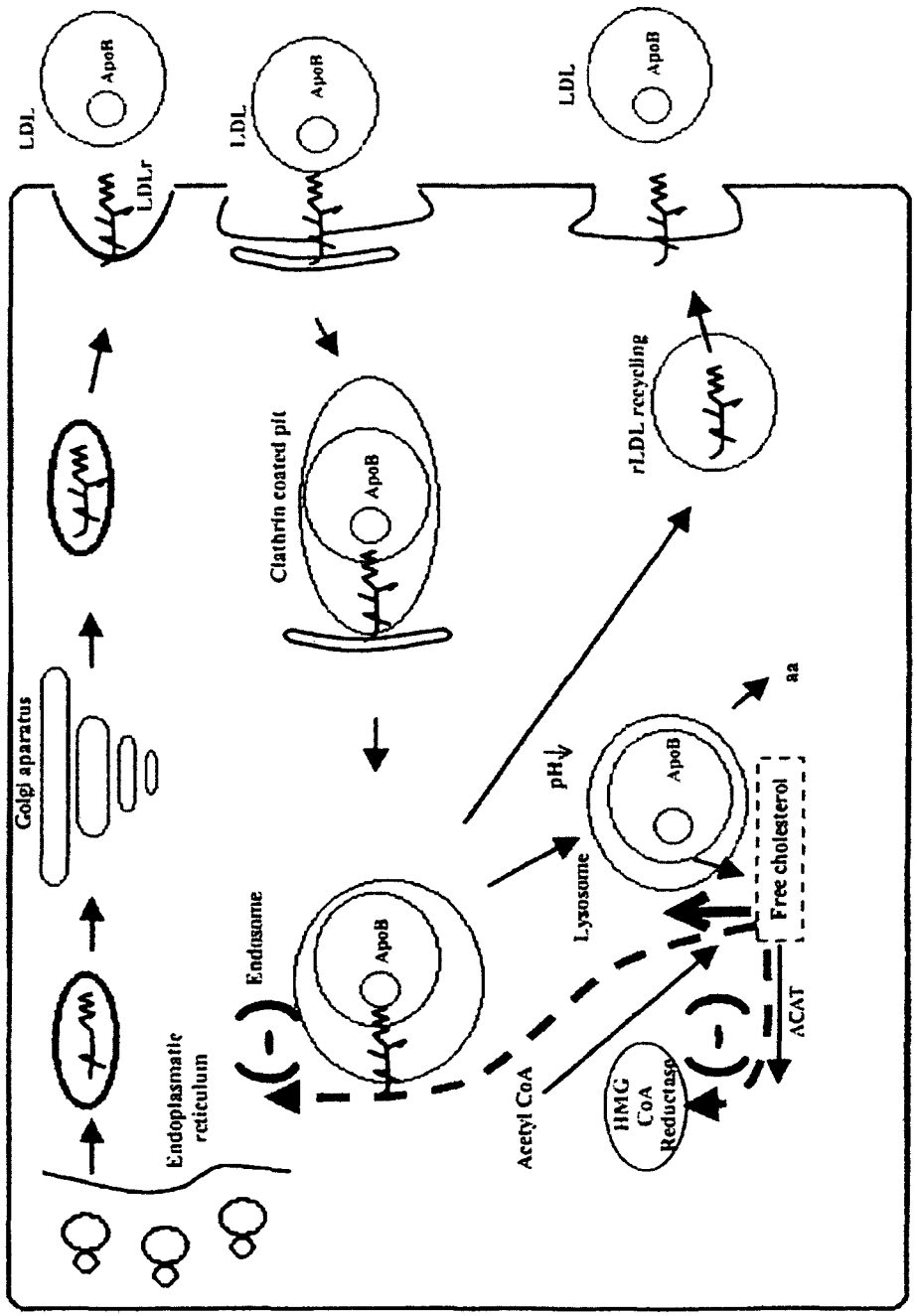
FIG. 1 is a schematic representation of the itinerary of the LDL-r in human cells. The LDL-r is synthesized in the endoplasmic reticulum as a precursor of apparent molecular weight of 120 Kd and transported to the Golgi apparatus. Once transferred to the surface of the cell the receptor recognizes the apolipoprotein B-100 component of the LDL. Binding leads to cellular uptake and lysosomal degradation of the LDL by receptor-mediated endocytosis. This uptake process satisfies the cholesterol needs of the cells, and hence keeps endogenous cholesterol synthesis suppressed.
Figure 2:
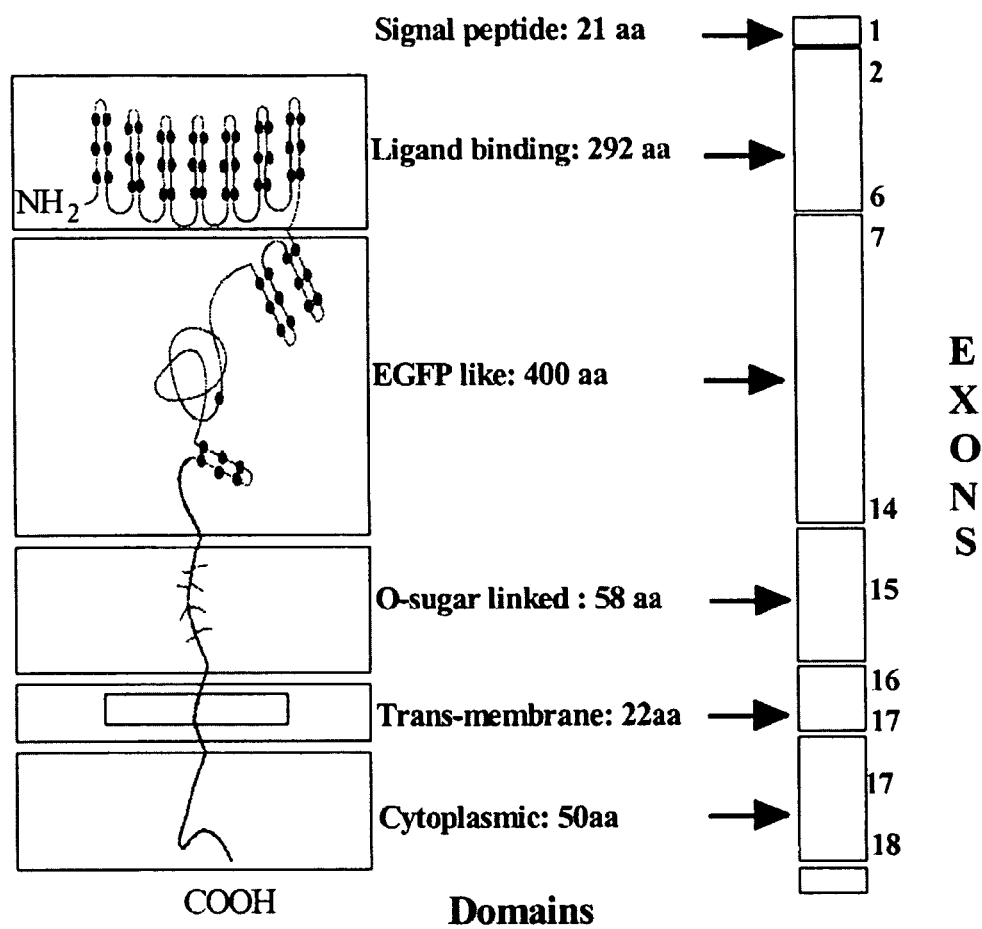
FIG. 2 is a schematic representation of the five domains in the structure of the human LDL receptor protein and their correspondence with the gene exons.
Figure 3:
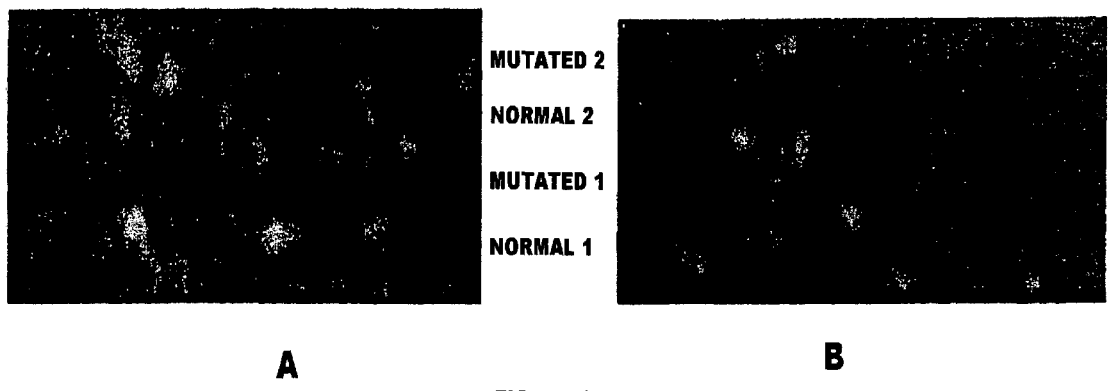
FIG. 3 Glass slide for quantification of image with 4 primers (2 normal and 2 mutated) repeated in 10 cups for the mutation E256K. (A) normal individual (B) individual with familial hypercholesterolemia. Two pairs of oligonucleotides were spotted for each mutation. Each probe pair consists of one probe specific for the wild-type allele and a second probe specific for the mutant allele.

<210> SEQ ID NO 1
<211> LENGTH: 60000
<212> TYPE: DNA
<213> ORGANISM: Homo sapiens

```
<220> FEATURE:
<221> NAME/KEY: CDS
<222> LOCATION: (15324)..(15390)
<220> FEATURE:
<221> NAME/KEY: mat_peptide
<222> LOCATION: (15387)..(15389)
<220> FEATURE:
<221> NAME/KEY: CDS
<222> LOCATION: (25998)..(26120)
<220> FEATURE:
<221> NAME/KEY: CDS
<222> LOCATION: (28439)..(28561)
<220> FEATURE:
<221> NAME/KEY: CDS
<222> LOCATION: (30995)..(31375)
<220> FEATURE:
<221> NAME/KEY: CDS
<222> LOCATION: (32340)..(32462)
<220> FEATURE:
<221> NAME/KEY: CDS
<222> LOCATION: (33167)..(33289)
<220> FEATURE:
<221> NAME/KEY: misc_feature
<222> LOCATION: (35360)..(35361)
<223> OTHER INFORMATION: n is a, c, g, or t
<220> FEATURE:
<221> NAME/KEY: CDS
<222> LOCATION: (35757)..(35875)
<220> FEATURE:
<221> NAME/KEY: CDS
<222> LOCATION: (36618)..(36744)
<220> FEATURE:
<221> NAME/KEY: CDS
<222> LOCATION: (38383)..(38554)
<220> FEATURE:
<221> NAME/KEY: CDS
<222> LOCATION: (38640)..(38868)
<220> FEATURE:
<221> NAME/KEY: CDS
<222> LOCATION: (41200)..(41317)
<220> FEATURE:
<221> NAME/KEY: CDS
<222> LOCATION: (41964)..(42103)
<220> FEATURE:
<221> NAME/KEY: CDS
<222> LOCATION: (45197)..(45338)
<220> FEATURE:
<221> NAME/KEY: CDS
<222> LOCATION: (45475)..(45626)
<220> FEATURE:
<221> NAME/KEY: CDS
<222> LOCATION: (48278)..(48449)
<220> FEATURE:
<221> NAME/KEY: CDS
<222> LOCATION: (53113)..(53190)
<220> FEATURE:
<221> NAME/KEY: CDS
<222> LOCATION: (54617)..(54774)
<220> FEATURE:
<221> NAME/KEY: CDS
<222> LOCATION: (56385)..(56417)

<400> SEQUENCE: 1
aaaagatggt gtatccattc aatggaacat tatttggcct ttaaaaggaa ggaaattctc      60
actgagcata gtggtttatg cctgtaatcc cagcactttg ggaggctgag cagggggga     120 gggggcggtt cacctgaggt caggagttca agaccagcct ggccaacatg gtgaaatccc    180
gtctctacta aaaatacaaa aaattagcc gagtgtggtg gcacacacct gtaagccagg    240
ctacacggga gactgaggca ggagaatcgc tggaacccgg gaggcagagg ctgcagagag    300
ccgagattgc gtcactgcac tccagcctgg gtgacagagc gagactcttg tcttaaaaaa    360
aaaaagaagg aaggaaggaa ggaaggaagg aagttctgac acaggctcca acacagatgt    420
tatgctcagt gaaataagcc agacatgaaa ggacaaatac tgcctgatct cattcataag    480
```

```
aggtccctag aattgtagaa tggtgtgtgc cacgggctgg gaggggtgt ggccagagtt   540
tcagtttggg aagttgagaa tgttctggag atggatggcg gtagtggtgg ttgcacaact   600
gtgtgaatgc gcttaatgcc tctgaattgt gcagttacaa gtggttcgga tgggccgggc   660
gcggtggctc atgcctgtaa tcccagcact ttgggaggcc gaggcaggtg gatcatgaga   720
tcaggagatc gagaccatcc tggctaacac ggtgaaaccc catctctact aaaaaataca   780
aaaaattagc caggcatggt ggtgggcacc tgtagtccca gctacttggg aggcggaggc   840
aggagaatgg cgtgaacacg ggaggcagaa cttgcagtga gccgagatca cgccactgca   900
ctccagcctg ggcgacagag tgagactccg tctaaaaaaa aaaagtggt taagatgggc   960
cgggcatggg ggatcacgct tgcaatccca acactttggg aggctgaggt gggtgattac  1020
gaggtcagga gttcgagacc agcctgacca ccatggtgaa accccgtctc tactaaaagt  1080
acaaaattag ccgggtgtcg tggcacacgt ctgtaatccc agctactggg gaggctgagt  1140
tgggaggatc acctgagccc agggaggtcc aggctgcagc aagccatgat tgcaccactg  1200
cactccagcc tgggtgagag agtgagaccc tgtctccaaa caaacacaca tgaaaaacag  1260
atttttttg ccaggtgcag tggctcacac ctgtaatccc agcactttgg gaggccaagg  1320
cgggtggatc acgaggtcag gtgactgaga gcatcctggc taacacggtg aaaccctggc  1380
tctactaaaa atacaaaaat ttagccgagc atggtggtgg gcacctgtag tcccagctac  1440
tcgggaggct gaggcaggag aatggcatga acctgggagg cggagcttgc agtgagctga  1500
gatcacgcca ctgcactcta gcctggggga cacagcaaaa ctgtctcaaa aaaaaaaaa  1560
aaggtttttt taatttaaaa aggaaagaaa aggagagtgc tcgtgtggca ggcacctagc  1620
cctgtccagc gcaccctgag acagggatga tgtctcctcc ttgacctaag accacaagtt  1680
ctaaccaatt caaccgagga cagagcccca attccaggca gggcaatggg gtcgccttgt  1740
gaactaagat gcagatggag aagagcagac acagacacag gtcttgggc ccctgcaggg  1800
gtttctcact ggcttttcc ccctggattc ctatgggttc tggggaacag agttaggtcg  1860
gctggcaaga cagatgcatg aggctgtggc gcccttgaca ttgagccgga gggccagagt  1920
tcgtcattgc tgacgcagag aagctgggag ccaaggttag ccagatggtt tggaggagtt  1980
ttaaacaatc tttttctttc tttctctttc catctgtctg tccttctttc ctcccttcct  2040
gccccttc ttttctcctt tctttccttc ctctctcctt cctccctttt tttcttttt  2100
tttggttttc ttttgtatt agtattatta tttttagac agggtcttgc tctgttgccc  2160
aggctggagg gcagtggcac gatcacagct cagtacaccc tcaaccttct gggttcaagc  2220
aatcctcctg ccttggcctc ccaggtagct gggactacag gcgtgtgcca ccacacctgg  2280
ttaatttttt tttttttga cggagtct tgctctgtca cccaggctgc agtgcagtgg  2340
cgtgatctcg gctcactgca acctccacct cccgggttca gcgatcctc ctgcctcagc  2400
ctcccgagta gctgggatta cacgcgcccg ccaccaagcc cggctaattt ttttattttt  2460
agtagagaca gagtttcacc acgttggcca ggctcgtctc aaactcctga cttagtgatc  2520
tacccacctt ggcctctcaa agtgctggga ttagaggcgt gagccaccat gcgcagccaa  2580
tttttgtatt tttagtagag atggggtttc accatgttgg tcagtctggt ctcgaactcc  2640
tgacctcaag tgatccacct gcctcagcct cccaaagtgc tggaattaca ggcatgagcc  2700
accgcgccca gccctcttaa ccatttttaa gtgcacagtt cagcagcatt aagcacattc  2760
acattgttgt gcaaccatca gccccgtcc atctccagct ttctctttt ttttgtttgt  2820
tttgagacag ggtcttactc tctcgcccag tatagagtgc agtggtgcgg tcttggctcg  2880
```

```
ctgcaacctc tgccttccag gttcaagcta ttctcctgcc tcagtctccc cagtagctgg    2940
gattacagac acacatcacc acgccctgct aattattttg catttttagt agagatggtg    3000
tttcaccata ttggccaggc tgatcttgaa ctcctggcct caagtggtct gctccaaact    3060
gctgagatta cagccgtgag ccactgctcc cagccatctg cacctttctc atcttcccaa    3120
atgtaactat gtccccgtga aacactcact ccccattcca cctccccagc ccctggcacc    3180
ccccatttta ttctggtgct aggggaattt caaaccaggc aagtctcaac acatgctcga    3240
gtgtaagaac cagcccacag cctcgttccc taatcacggt caaaccagaa ttctactcca    3300
ggttctactc tgtgaatctg ctttctgtga atctgttact ctggggaccg cctataagtt    3360
gaatcctaca gtgtctccac ttcagtgact ggcttatttc acttttctcc tctttattta    3420
tgagacaaaa tttcgctctt gttgctcagg ctggaatgca atggcgtgat ctcggctaat    3480 tttttgtat ttttagtaga ggcggggttt caccatgttg gccaggctgg tctcgaactc    3540
ctgacctcag acgatccact ttggccttcc aaagtgctgg gattacaggc gcggcccacc    3600
tttctcctct taatcacaca ggtaatccat acatacgaca ttcttttttt ttttgacac    3660 ggagtcttac tctgtcacct aggctggagt gcagtggcgc aatctggct cactgcaacc    3720 tctgcctccc aggatcaagc aattctcctg cctcagcctc ctgagtagct gggattacag    3780
gtaaccatca ccacacctgg ctaaattttg tattttagt agagacgggg tttcaccacg    3840
ttggccacgc tggtattgaa ctcctggctt caagtgatct tcctgtctcg gtctcccgaa    3900
gtgctgggat tacaggaatg agccactgtg cccggccaat acgacatctg tgcaatgaag    3960
tgcaacatat aagcacccct tcccccaccc actgccccca ccaccgcccc cacgccccca    4020 ccccatctc cagatcagaa cctggggctg tgcaattta aacgttgtag ccacttgcta    4080
cttgggtagt tgaagttcag tctcagccag gttggagtcc tggactctgg ccctctttt    4140 attttattt tttattttt tttgagacag agtctcgctc tgtcgcccag actggagcgc    4200
agtggtgcga tctcggctca ctgcaagctc tgcctcctga gttcacgcca ttcccccgcc    4260
tcagcctccc gagcagctgg gactacaggc gcccgccacc acaccgcct aatttcttgt    4320 attttttagt agagatgggg tttcaccctg ttagccagga tggtctagat ttcctgacct    4380
tatgatccgc ctgcctcggg cctcccaaag tgctgggatg acaggagtga gccaccgcgc    4440
ccggcctctt ttttttttt tagacagtct ctgtcaccca ggctagagtg cgatggtgcg    4500
atctcggctc actgcaacct ccaccttccg ggttcaagcg attctcctgc ctcagcctcc    4560
tgagtatctg ggattacagg tgcctgtgac cacgcccggc tgattttgt attttagta    4620 gagacggggt ttcaccacat tggtcaggct agcctcaaac tcctgacccc gtgatccttc    4680
cgcctcagcc tcccaaagtg ctgggattac aggactctgg cccatcttgg ctgctgccaa    4740
tgtccttcct tctatcttgg ttttttccaca gttacgcaca tgccagataa cggcgagtct    4800
gttccccagc aactgcaacg gatctgccca ccactgggaa atggaagacc ttgcagccca    4860
ggtctttgta gaccaagatt agattgtggt caacaaacac ctgaccttgg cctttggaac    4920
catcagccat gtcagctaaa ataaaagcag aatctggctg ggcgcagtgg ctcacgcctg    4980
taatcccagc actttgggg gctgaggtgg gcagaccacc tgaggtccgg cgttctagac    5040
cagcctgacc aatatgatga aaccccgtct ctactaaaca tacaaaaatt agctgggcat    5100
ggtggcgggc acctgtaatc ccagctactc gggaggctga ggaaggagaa ttgcttgaac    5160
cctggaggca gaggttgcag tgagccgaga ttgcgccact gcactccaac ctggactgca    5220
gaacaagact ctgtcccaaa agcagataaa taaaaataaa taaaaataaa aatatggccg    5280
```

| | |
|---|---|
| ggcatggtgg ctcacacctg taatcccaac actgggaaga tgaggcgggc agatcacgag | 5340 |
| gtcaggatt cgagaccagc ctggccaaca tggtgaaacc ccgtctctac taaaaataca | 5400 |
| aaaattagcc gggcatgatg ctgcatgcct gtaatcccag ctactctgga ggctgaggca | 5460 |
| ggagaatcgc ttcatcccgg gaggtggagc ttgcagtgag ctgagatcgc gccactgcac | 5520 |
| tctagcctgg gcaaaagagt gagactccat cgcaagaaaa aaaaaaaaaa aagctgcaag | 5580 |
| ctctgtctcc cgggttcaag tgattctcct gcctcagcct tccaagtagc taggattata | 5640 |
| cgcgcccgcc accatgcctg gctaatttttt gtattttag tagagatgcg gtttcaccat | 5700 |
| gttggccagg ctggtctcaa actcctgacc tcacgtgatc cacctgcctc ggcctcccag | 5760 |
| agtgctggga ttacaggtgt gaaccctgc gcctggccaa gaaaagttgc ttgaatgaag | 5820 |
| agtaaataga agacccagaa agaaatgatt cgtccgagga aggtcacaga agcaacgtaa | 5880 |
| tcaagatgga aatctgactc ttcctaattt tggccagact tcccatccct ccaaagcttt | 5940 |
| ccagactctt ccagatcatt ctagatattt ccagaaatca ttcgtgaaat ctaactagga | 6000 |
| gtagtctgta aacaatgtgt ttcacacaga tacaattcat aaacgatgag aagacaagga | 6060 |
| cacttcatga atgaaatttt tacggccggg tatgttggct cacgcctata atcccaggac | 6120 |
| tttggaagac ccaggcagga ggattgcttg agtccaggag ttcaagacca gtctgggcca | 6180 |
| catagtgaga ccctgtcgct acaaaaaatt taaaaattag gtagatatgg tggtgtatgc | 6240 |
| ctctagtttt agctttttttg gaggctgaag caggaggatc tcttgagccc aggaggttga | 6300 |
| gctgcaatga gctacgattg aactactaca ctccagtctg ggtgacagag aaagaggctg | 6360 |
| cctcaaaaaa ataaaaataa aaaataagg ccggacgcgg tggctcacgc ctgtaatccc | 6420 |
| agcactttgg gaggctgggg tgggcagacc acgaggtcag gagatcgagg ccatcctggc | 6480 |
| caacatgatg aaaccctgtc tctactgaaa acacaaaaat tagctgggcg tggtggcgta | 6540 |
| tacctgtaat cccagctact cgggaggctg aggcaggaga atcacttgaa ccagggagtc | 6600 |
| agaggttgca gcgagaggag attgtgccac tgcattccag cctggcaaca gagcaagact | 6660 |
| ccgtctcaaa aaagaaacaa caacagcaac aacaacaaaa aaaacataaa aaagttcggg | 6720 |
| cacggtggct cacacctgta atcccagcac tttgggaggc caaggtgggt agatctcttg | 6780 |
| aggtcaggag ttcaagacca gcctggccaa caaacatggt gaaaccccgt ctctactaaa | 6840 |
| aatacaaaaa gtagccgggt gtagtcccag ctactcggaa ggctgaggca ggagaatcgc | 6900 |
| ttcaacctgg gagatggaag ttgcagtgaa ctgagattgc gccactgggt gacagagtaa | 6960 |
| gactcttgtc tcaaaaaaaa aaaaagaaag aaagtttaat ttaatgattc aaataatgac | 7020 |
| ctgctcgaga gataaatata aagtctaacg taagaggtgt atacttttc ctctgtcctg | 7080 |
| ctgtcctcgc cccacctcac cccaagtccc aacctgattg atcagtctcc tttccctctg | 7140 |
| gtagccccac tcccatgacc gaaccgagaa gtcatgcacc cgcataagaa ctctaatttt | 7200 |
| ttttttcaaa gtcttctcac tgccccaaaa atagtttctt tcattcccag gggatgtgaa | 7260 |
| agtgtctctc ccaattttat ttcaacctcc cagcgttcca cacatatgcc ttgcctcagc | 7320 |
| cagcttttcac tgatctgcca tttccactc ggcgctgctc ctacctgcgg aaatcctgtc | 7380 |
| catccatagt ctgatttctg ttgttccaga acattctttt ttttttcccc tggaacattc | 7440 |
| tttaagatac ctcaataaat gaaaccagag ggtatagagc agtatgaatg ggtactacaa | 7500 |
| tgtacagggg gaaatggagg ggaatatgat atactctcct ccttgtatat gcttagaatg | 7560 |
| ttctagaagg atatgcttaa aaggttagca gtcctggcca ggcgtggtgg ctcacgcctg | 7620 |
| taatctcagc actttgggat gccaacgcgg acggatcaca aggtcaggag ttctagatca | 7680 |

```
gcctgaccaa tatagtgaaa cctcatcttt actaaaaata caaaaattag ccgggtacgg    7740
tggcatgtgc ctgtagtccc agctactttg gaacctgagg caggagaatc gcttgaactc    7800
gggaggcaga ggttgcagtg agccgagact gtgccattgc actgcagcct gggtgacaga    7860
acaggactcc gtctcaaaaa aaacaaaaa aggtcagcag tcttaattgt cagagggcag    7920
gggacctgca tgggatggag gttttccat gtgtccacct tttgagccct tttgcttttt    7980
ttttttaaat cttttattg tagcaaaata gatataaaat ttacccttt tttttttgag    8040 acagggtctc actctgttgc ccaggttgga gtgcagtggc atgatcttgg ctcactgcag    8100
cctctgcctc ctgggttcaa gcgattttcc tgcctcagcc tcccgagtag ctgggattac    8160
aggtgcttgc caccataccc ggctaatttt gtattttag tagagacggg gttacgccaa    8220
gttggccaag ctggtcgcaa actcctgacc tcaagtgatc cgccccctc ggcctcccaa    8280 agtgctggga ttacaggcag gagccaccac gctcagccct aaaatttacc atattaacca    8340
ttttcaagtt cagaggcatt aaagtatact cacattgttg ttcaactgtc accactactc    8400
acctgcagaa gttttcatc ttgcaaagtg aaaacccat acccaatttc ccgttcttcc    8460
tctcagcccc tggtaatcac tattctactt tttgtctact ttttgtatga atttgcctat    8520
tctaggacct aatagaagtg gagtcaaacc tgtttgtcct tttgtggctg gcttatttca    8580
cccggcctta tatcctcaag gtttatccat gttggaggat gcctgaattt ccttgttttt    8640
aaggctaaat tttattctat tatattaata tgtcatattt tgtttatcct gatggacact    8700
tgggttgatt ccacctttgg ccattttgaa gaagcttcta tgtacatggt atacacatat    8760
atctttgggt ctctgcttc aatgcttttg gggatatttc agatgtggaa tttctggatt    8820
ataaggcaat ttttttttt gagacagact ctcgctcttg tcgcccaggc tagaatgtgg    8880
tggtgtgatc tatttttttt tttttttttga gatggagtct cgctctgtcg cccaggctgg    8940
agtgcagtgt cacgatctca gctcactgca agctccgcct cccaggttcg tgccattctt    9000
atgcctcagc ctcccaagta gctgggacca cagccgccca ccacctcacc cggctaattt    9060
ttgtattttt agtagagaca gggtttcact atgttggcca ggatggtctc gatctcctga    9120
cctcgtgatc cgcctgcctc ggcctcccaa agtgctggga ttacaggcgt gagccactgc    9180
acccggctgg tgtgatcttg gctcgctgca acctctgcct cccaggttca agcgattctt    9240
gtgcctcagc ctctccgcag ctgggactac aggtgtgcgc cactgtgccc agctactttt    9300
taaaaatata tgtgtattta ttatacttt aagttctggg atacatgtac agaacgtgca    9360
ggtttgttac ataggtatac atgtgccatg gtggtttgct gcacccatca accggtcatc    9420
tacattaggt atttctccta atgctatccc ttccctagcc ctccactctc ccggttttt    9480 gttttgtttt gttttgttgt tttgttttta gtagagacag ggtctcacca tgttgcccag    9540
gctagtcttg aactcctgac ctcaagtgat ccgcccacct cagcctccca agtgctggg    9600 attacaggtg tgacccacta cactcggcct tattttcact tatttatgca atttcacta    9660 ttgctatatt ctaggaggca ctgtggaatt gcactgtgga atttagtat tgctgtattt    9720 cagcaagcca tgaggtctgt cagcacacgg ctttgggcat tttgtgaaga taactgatgc    9780
cagctgagcc aaggcaggtt cctgattcca cccactggca ggcaccgagg tctctgctgt    9840
tactgatggt ttctctgtgg attgatgggc ttaaggccag accacagctg caatggctca    9900
cctctgccaa aggccaggct cgttggggca gagaccatt ccggactgag cctcctggtg    9960
aattagagag gtagaaaatg ggaggacggg ggcaggtggg ctattacagc gaggaaaatg   10020 cccacccctga gttgtattag ataactttgg gagttcagga actttccaat aaagtgggtt   10080
```

```
ccacagcagg attacttact gactccctaa tagaaagaag gcaggcacag gccgggcgtg    10140
ttggctcatg tctgtaatcc cagcacgttg ggaggctgag gcgggtggat cacaaggtca    10200
ggagatccag accatcctgg ctaacaaagt gaaaccccgt ctctactaaa aatacaaaaa    10260
attaggctgg gcgtggtggc tcgtgcctgt aatcccagca cttttgggagg ctgaggcggg    10320 cggatcacga ggtcaggaga tcgagaccgt cctggctaac acggtaaaac cccatctcta    10380
ctaaacatac aaaaaaaaat tagccaggtg tggtggcggg cgcctgtagt cccagctact    10440
caggaggctg aggcaggaga gtggtgtgaa ctcgggaggc gcagcttgca gtgagccgag    10500
actgcgccac tgcactccag cctgggcaac agacagagac tccgtctcaa aaaaaaaaa    10560 aaaaaataca aaaaattagc caggcgtggt ggcacgtgca cgtgactgta gtcccagcta    10620
cttgggaggc tgaggcagga gaattgtttg aacccgggag acggaggttg cagtgagccg    10680
agatcgcgcc actgcactcc agcctgggtg acagagctag actccgtcaa aaacaaaaa    10740 acaaaaaaca aaaaacaaa aaaaaaaaaa cagcaggaac tggcaggtct tccctgaaga    10800
gataaaaaaa aaaaatgca gttgcaacac aaaagcagcc acagagaaaa gcaaacccat    10860
atatggtatt tattatgcac cgagtgtggc tctaatcact ttttttttt taattgagag    10920 acagcctggc tctgttgatt gggctggagt gcagtggcgc gaccgtagct cattgcagcc    10980
tcaacctcct tggctcaagc aatcctccta cctcagcctc ctgagtagct gggaccacag    11040
gtgtgagcca ccacgcctgg ctaattgttt tttttttttt tgtagagaca gggtctcact    11100
atgtggccca ggctggttttc caactcctgg gctcaagtga tcctcccacc tctgcctccc    11160
aaagtgctgg ggattacagg catgagccac ctcgcctggc ctctagtcgc tttatatatt    11220
ttaacttaat ccttacaaga gccctgtgag ctagttacag gagcacaaat ggaaaccaag    11280
aaacagaaaa atttatcagc atgactcagt cctcagagcc atgtatggcc gtgtccgtgc    11340
atggcaggca ggtcagggc ctggggaacg ctgttctgga aaccttggcc aggccttggc    11400
acccgaggaa tgtgcttttc agagtttttg tggctctttt ccagacctgc cctgacctct    11460
agctctggga actatgtaag ccaagtgcct tccgggaagg gagtccctct cctggtaact    11520 cttttctgggt aaccagatgt ggactcatga cacacactga gcctacgtct tataattttt    11580 tgttttttgtt tttgagacag tttcggtctt cttgcccagg ctggagtgca atggtgcgat    11640
ctcggctcac tgcaacctct gcctcccagg ttcaagcgat tctcctgcct cagcctccca    11700
agtagctgga attgcaggca tgcgccacca cgcctggcta atttttttgta ttttttttt    11760 tttagtagaa acgggttttc accttgttag ccaggctggt caccaactcc tgacctcagg    11820
tgatccgccc acctctgcct cccaaagtgc tgggattaca ggtgtgagac agctgtgagc    11880
caccacgccc ggcgcatttt tttttctttt tttttcagag ggagtgtccc tctgtcaccc    11940
aggctgaagt gtagtggcgt gatctcggcc cactgtaacc tctatctccc aggttcaagt    12000
gattctcctg actcagcctc ccaagtagct gggactacag gcgcctgcta ccatgcctgg    12060
ctaatttttg tagttttagt agaaaccggg ttttgccatg ttggccaggc tggtctcaaa    12120
ctcttgactt caggtgatcc acctgccttg gccttctgaa gtgctgggat tatagggcat    12180
gagccactgt gactggccat cttaaatttt ttttttttttt tttttttttt ttgagacagg    12240
gtttcactct gtcgcccagg ctggagtgca aggcgcgat cttggttcac tgcaagctcc    12300
gcctcctggg ttcatgccat tctcctgcct ctgcctcatg agtaactgag actacaggcg    12360
cccaccacca cgcccggcta atttttttgt atttttttag tagagatggg gtttcacctt    12420
gttagccagg atggtctcga tctcctgacc tcgtgatcca cccgtctcgg cctcccaaaa    12480
```

```
tgctggcatt acaggcgtga gccaccgcac ccagccttaa attttttttt aagggaaatc    12540
aaacccagtg atattgggcc agtacagtgg ctcacacctg taattccacc actttgggag    12600
gctgaggcag gtgaatcacc tgaggtcagg agttcgagac cagcccggca acatggcga    12660 aaccccgtct ctactaaaaa taagaaaatt agccgggcgt agtggcatgc acctgtaatc    12720
tcagctactc gggaagctga ggcatgagaa tcgcttgaac ctgggagcag gacgttgcag    12780
tgaaccgata tcacaccact gcactccagc ctgggtgaca gagcaagact ctgtctcaaa    12840
aaaaaaaaga aaaaaaaatc cagtgatact tacttttaa attttatt acttatttt    12900 tgctttaagt tgaatcttta aacttatctt tattttgag acacagtctc actctgtcgc    12960
ccaggctgga gtgcagtggt acaaccacag ctcagtgcag cgttgacctc ctgggctcaa    13020
gccatcctcc cgcctcagcc tcccgagtag ctgggactac aggcgcacac aaccatgtcc    13080
agcttatttt tgtattttt gtagagacag gtcccactg tgttgccctg cttgttctg     13140 aactcctagg ctcaagtgat cccccgcct caccctccca aagtgctggg attacaggca    13200
tgagccacca catccagact tcactttttt gtttaatgtc gcaaatggca taaggaatgg    13260
gattcaatgg ggacacattt ataaacgttg cagcagctcc tagaacttgc ctatccttgt    13320
aaacttctct aggtgattgc taattacttc tttttttttt tttttttttg agacggagtc    13380
tcactctgtc gcccaggctg gagtacagtg gcgcaatctc gtctcactgc aaactccacc    13440
tcccgggttc acgccattct cctgcctcag cctcccgagt agctgggact acaggcaccc    13500
gccaccacgc ccggctaatt ttttgtattt ttttttagta gaggtggggt ttcactgtgt    13560
tatccaggat ggtcttgatc tcctgacctc gtgatccacc tgcctcagcc tcccaaagtg    13620
ctgggattac aggcgtgagc caccatgccc agcccgctaa ttatttcaat ttgaccttga    13680
cactgagcct gccaagtagg ttcaagcatt ttgatggccc ctttacaggt tgggaaagct    13740
aatttatctg tccaaggccg aattctgaaa ctgagtctta actgccaaaa attcttatca    13800
tcaatttctt cttctgggtt gggcacagtg gctcatgcct gtaaagccag caatttgaga    13860
ggcatcatga tgcaagagga agaggattga gtgaagctag gagtttggga ccagcctggg    13920
caacatagtg agaccccatc tataaaaaaa aattaaaaat tagttgggca tggtggtgca    13980
ctcctgtggt cctagctatt caggaggctg aggtgggagg attccttgag cccagggttg    14040
acgctgcaga gagctgtgat cacgccactg cagtccagcc tgagtgacag ctggaaataa    14100
tgataaataa ataataaata attatttaaa aattataat aaaaataatt aaaaaattat    14160
tttccctgat taatctttt ttttgtcctt ctgagagttc aatttgtccc ttttctgcct    14220
ggtctcctag gtttccctaa aatcctgctg agaggttagc actgcctgcc aaagtcagtt    14280
tgcaaaatcc cagagaaatc cagcttattc ctggggaac cgccaagact gcccagccct    14340
gtgtggggtt caggcaagtt tctcacatgt gccttttgg caagaggcct ctggcaaccc    14400
catgagtccc caaagagact caattctaaa agttggtctc caccagctct ctgtggctta    14460
ggggttcaag ttcaactgtg aaagccctgt tttgtttga ttttgctttg agggagagga    14520
aaccgcccct ctgtttgttc aactccttct cctaagggga gaaatcaata tttacgtcca    14580
gactccaggt atccgtacaa ttgattttc agatgttat actcagccaa aggcgggatc    14640
ccacaaaaca aaaatatttt ttttggctgt acttttgtga agattttatt taaattcctg    14700
attgatcagt gtctattagg tgatttggaa taacaatgta aaacaatat acaacgaaag    14760 gaagctaaaa atctatacac aattcctaga aaggaaaagg caaatataga aagtggcgga    14820
agttcccaac attttagtg ttttccttt gaggcagaga ggacaatggc attaggctat    14880
```

```
tggaggatct tgaaaggctg ttgttatcct tctgtggaca acaacagcaa aatgttaaca   14940
gttaaacatc gagaaatttc aggaggatct ttcagaagat gcgttccaa ttttgagggg   15000 gcgtcagctc ttcaccggag acccaaatac aacaaatcaa gtcgcctgcc ctggcgacac   15060
tttcgaagga ctggagtggg aatcagagct tcacggtta aaaagccgat gtcacatcgg   15120
ccgttcgaaa ctcctcctct tgcagtgagg tgaagacatt tgaaaatcac cccactgcaa   15180
actcctcccc ctgctagaaa cctcacattg aaatgctgta aatgacgtgg gccccgagtg   15240
caatcgcggg aagccagggt ttccagctag acacagcag gtcgtgatcc gggtcgggac    15300
actgcctggc agaggctgcg agc atg ggg ccc tgg ggc tgg aaa ttg cgc tgg   15353
                      Met Gly Pro Trp Gly Trp Lys Leu Arg Trp
                      -20                 -15 acc gtc gcc ttg ctc ctc gcc gcg gcg ggg act gca g gtaaggcttg        15400
Thr Val Ala Leu Leu Leu Ala Ala Ala Gly Thr Ala
 -10            -5                -1  1 ctccaggcgc cagaataggt tgagagggag ccccgggg gcccttggga atttattttt     15460
ttgggtacaa ataatcactc catccctggg agacttgtgg ggtaatggca cggggtcctt    15520
cccaaacggc tggagggggc gctggagggg gcgctgagg ggagcgcgag ggtcgggagg     15580
agtctgaggg atttaaggga aacggggcac cgctgtcccc caagtctcca cagggtgagg    15640
gaccgcatct tctttgagac ggagtctagc tctgtcgccc aggatggagt gcagtggcac    15700
gatctcagct cactgcaacc tccgcctccc gggtttaagc gagtctcctc tctcagcctc    15760
ccgaatagct gggattacag gcgcccaacc accgcccg cctaatttt gtatttttag      15820 tagagacggg ttttcaccat tttggccagg ctggtctcga accccgacct caggtgatct    15880
gcccaaaagt gctgggatta caggcgtcag ccaccgcgcc cggccgggac cctctcttct    15940
aactcggagc tgggtgtggg gacctccagt cctaaaacaa gggatcactc caccccgc     16000 cttaagtcct tctggggcg agggcgactg gagacccgga tgtccagcct ggaggtcacc     16060
gcgggctcag gggtcccgat ccgctttgcg cgaccccagg gcgccactgc catcctgagt    16120
tgggtgcagt cccgggattc cgccgcgtgc tccgggacgg gggccacccc ctcccgcccc    16180
tgcccccgcc cctttggccc gccccccgaa ttccattggg tgtagtccaa caggccaccc    16240
tcgagccact cccccttgtcc aatgtgaggc ggtggaggcg gaggcgggcg tcgggaggac    16300
ggggcttgtg tacgagcggg gcggggctgg cgcggaagtc tgagcctcac cttgtccggg    16360
gcgaggcgga tgcaggggag gcctggcgtt cctccgcggt tcctgtcaca aaggcgacga    16420
caagtcccgg gtccccggag ccgcctccgc gacatacacg agtcgccctc cgttatcctg    16480
ggccctcctg gcgaagtccc cggtttccgc tgtgctctgt ggcgacacct ccgtccccac    16540
cttgtcctgg ggggcgccct cgccccacca gccccgatca agttcacaga ggggccccg    16600 gccacccctca aggcctcggt tccttacgag gttgaaacgt tgcctcagaa tctccccgcc   16660
cctccttggt ctgcagccga gatcttcagc cacggtgggg cagctatccc ccgggaccga   16720 cccctgggg tggcctcgct tcttcagagg ctgtgaatgg cttcggttca gctgtccaag    16780
cggcgatttt tcctctgggt gaaatggatt agattttaga tttccacaag aggctggtta    16840
gtgcatgatc ctgagttaga gcttttagg tggctttaaa ttagttgcag agagacagcc    16900
tcgccctaga caacagctac atggcccttt ccctcctgag aaccagccta gcctagaaaa    16960
ggattgggat tgcctgatga acacaaggat tgcaggaaac ttttttttta attggcaagg    17020
gggttggctt tgactggatg gagagctttg aactgccttg aaattcacgc tgtaactaac    17080
acaccagttt cctctgggag gccagagagg gagggagggt gtaatgaaat acggatgatt    17140
```

-continued

```
gttcttttat ttttatttac ttatttattt tttaactttt tgtagagatg aggtctcgct      17200
tggttgctca ggctggtctt gaactcctgg cctcaagcga tcctcctacc tcagcctccc      17260
aaagtgttgg gattacagga gtgagccacc gcgcccacc ggggatgatg atgattgcaa       17320
acattctgcc actcagtttt acaaaagaaa gagaggcact ggattaatgt gtatctcact      17380
caccaatcaa cctcttcctt aagagaaaat gttaaggaag tcttaggcaa ggccttgttt      17440
gttcatcact ttagtttctc tctcccggga tggctgagaa tgtgatgttt cctctgttgt      17500
caaggagact acacccctga tgttttcctc cagacttctg agagctggtg tgtgtttcta      17560
gcactttcta gctgcaccac ctcacgctgt agctggcttc aaggcatatc caggggggag      17620
tttcttgtcc atttccttta caaagggaag ttgttggaat ctgaaccgca agccttcact      17680
tagaccaaaa tcaggcaaca gcggtgagcg cagctccaaa cgtgtcaatg actcacccaa      17740
atttgagtaa gggagttggc tgctttaacg agccgcaggg tgattcccctt gtcatttccg     17800 gaaataccta tcttccaggg aacactggga aaaacaggg agacctttgt tgagacagaa       17860
aacctgtagg ggaattctgt tcctcattcc tgctcttatc tgtagacttc ctccctgata      17920
agatccaatt ctagatgggt cggttgctcc ttgctttgat gggtgctttg atgggcttta     17980
ttattattat tattattatt attattattt tgatgggctt tttgatgtcc cttttccttc      18040
cacactctgt cccaactgtc aagcaaatag ccttttgttg ctaagagact gcagatgtaa      18100
ccgaccagca gcaaacagtg agtcaggctc tctcttccgg aagcaaaatc aattgctgag      18160
atcactctgg ggaaaatacc caccttattt ggaaagaagc actgatcaat tgatgtctat      18220
tttttttttt tttgagttgg agtctcgccc tgtcacccag gctggagtgc aatggcataa      18280
tctcgcctca ctgcaatccc cgcctccgg gttccagcaa ttctcctgcc tcagcctcct      18340
gagtagctgg aattataggc gcctgccaca acacccggct aattttgta tttgtagtag       18400 agatggggtt tcaccacgtt ggccaggctg gtctcgaact cctgacctcg tgatccaccc      18460
gcctcagcct cccaaagtcc aaggattgca ggcgtgaccc actgtgccag ccaatcaatt      18520
gatttctcat tcattttcag ctggctctgt tcccttaagc cagggatttt cgtttgttt      18580 gtttcccctt caaggaaatg attctagcta cagttttgat ttccttgtac aactgttttc      18640
agtagcacag ggaaagaaaa catcgaaagc attcaccacc tcatttgtgt gctggggaa      18700 aaagcagaaa tgtgtattct cttttttgt ttcgatgacc ttgttcctga cttgttactc      18760
gtgacttgag agatcagagg gctagaggac tagaatttat agaggtgttt tttttgtttg      18820
tttatttttg ttcgagttgc ccaggctgga gtgcagtggc gcaatctcgg ctcactgcaa      18880
cctctgcctc ccaggttcaa gcgattcttc ggcctcagcc tcctgagtag ctggaactac      18940
aggcgcccgc caccacaccc agctaatttt tgtatttttc agtagagatg ggatttcacc      19000
atattggtca gctggcctc gaactcctga cctcgtgatc cacccgcctc agtttcccaa       19060
agtgctggga gtacaggcgt gagccgccgt gcccggcctt tttgtgtttt tgtgtttttg      19120
agaggagctc attgcttttt aggcttccct agcgtgagaa aatctgggga tccatgctct      19180
agtttacttc cttttttttt tttttttga gatggagtct cgcttagatt gcctaatctc      19240
agctcattgc aacttctgcc tccggggttc aagggattct cgtgtctcag cctcctgggt      19300
agctaggata cgggcacccg ctaccatgcc tggctaattt tgtacttta gtagagacag      19360 ggtttcgcca cgttggccag gctggtctcg aactcctgac ctcaggtgag ccgcctgcct      19420
tggcctccca aagtgctgag attacaggcg tgagccaccg cgcttggcct aatttgcttt      19480
tcctgaaatt caaatggtct aatatgaaaa acgccaacct tgcttgaaag aataagaaag      19540
```

```
aggtgcggtt tcgttgggcc gttgatgttt ggaacaggac tggttttgtc cccttgctcg    19600
gaaagggcag caactgtgag gacagctccc tgacgtgctc tcactcagca ctgttccgtt    19660
cctgagcact gtccccacta gctaggccaa gggagctcat ttggcaggca actgctgtct    19720
ggctgcgcct gtggcagtaa aatctgcctt tattttttgg aggcagggtc ttgccctgtc    19780
gctcaggctg aagtgtgcag ttatagctca ctgcagcctc cagcttctgt actcaactga    19840
tcctcctctc tcagcctcct gagtagctgg gactatacgc acgtgttacc actcccacct    19900
cagtttgttt gtttatttat ttatttattt atttattgag atggagtttt gctcttgctg    19960
cccaggctgg agtgcaatgg cgcgatctcg gctcaccgca acctccacct cctggttcaa    20020
gcgattctcc tgcctcagcc tcctgagtag ctgggattac aggcatgcac caccacgccc    20080
ggctaatttt gtattttttcg tagagatggg gtttctccac attggttcag gctgttctcg    20140
aactcccaac ctcaggtgat ccacccgcct cagcctccca aagtgctggg attataggcg    20200
tgagcccccg aacccggcca ctcccagcta agtttaaatt ttttgtttgt ttgttcgttt    20260 gttttttattt tttgagacag agtctcccgc ccaggctgga gcgcagatca ctgcatcctt    20320
gacctcccag gcttaagcca tcctcccac tcagcctccc aagtagctgg gattacaggt    20380
gtgtgccact atgcttggct aagttgtgta tttttttgtag atgggggtt caagggattc    20440 tcgctttgtt gcctcggttg gtctcaaact cctgggctca agcagtcctc cctcctcagc    20500
ctcccaaggt gctggggaaa tccacttttg aaacattgtc tggagagttg cccaggtggt    20560
agatcacaga aataggtcat cgtggggtcc ttcccatggg tgcagtcttg agccacctgt    20620
ggccagcaaa tatttggaga ataatagtca ggggagagct tgaggtccag ggaaaggttt    20680 tgttttctt cagggaaagg tttttattgt tctttatccc tccttaaagg accttcaggt    20740
gttactgaca ttcccggtct acccagtggc acatttagtt tgtaagctgg gccctcgtac    20800
agaggtaggg aggtgagagc attggattag tggtcaccaa agctgcggtc acctagtggg    20860
gtgatcagag gctcctccct taagatcttg attgccaacg cctctggccc aactttcctt    20920
tttatttatc gcaagcctcc tggaatctca attgcttttt gcccacccgg tgtgtcagca    20980
caagaaatga gtcatttcct cctttaagca cagttgaaat tgagctgtga gtcagtgagg    21040
tgtgtacgat attgtcaaag cggggtgtgt acagtattga cagatctgta gttgggcaag    21100
agaattatca gagtttgtga ccacagcaga ttccaaagct cgactcattt tcttctctct    21160 tccttcccctt ttttctttc ttttttttttt ttttttgac agagtctcgc tctgttgccc    21220
aggctggagt gcagtggcac aatctgggct cactgcagcc cctgcctcct gggttcaaat    21280
gattctcatg tttcagcctc ccgagtagct gcaattacag gcattcgggt tcaagtgatt    21340
ctcctgcctc agccacctga gcagctggga ttacaggcgc cgccaccac gcccggctaa    21400 ttttttgtatt tttagtagag acggggtttc accatgttgg ccaggctggt ctcgaactcc    21460
tgaactcagg tgatccgccc acttcggcct cccaaagtgc tgagattaca gacgtgagtc    21520
accgcgccca gcctgttctg ttctttaatt ctcaaaacac cctctaggaa gtagagactg    21580
ccattctccc ccattttaca gatcaggaaa ctgagtccca gaaggattta gtcagttacc    21640
caagttgttc tagttaaatg gcctggaaag ccagtgaagc ccaggattgt ctatctaacc    21700
cccttactac tctaactttc agggaatcca catgaatgtg ctgggtcaac catcaaagtt    21760
gaaatggata agggggctg gatgcggtgg ctgatgcctg taatcctagc actttgggag    21820
gccgagatgg gtgggtggat tgcttgagcc caagagtttg agaccagcct gggcaacata    21880
gtgagacacc tgtctctgca aaaataaat aaaaagttag ctgagtgtga tggtgcaccc    21940
```

```
ctctagtcac agctgttgag ttaggcttag gcaggaggat cgcatgaacc tgggaggtgg    22000
aggcggccgt gagcctcagt catgccactg cactccaacc tgggcaacag agtgaaagcc    22060
ggtgtccgaa agagaaagaa aaaaagacat agatacatct tttaaagtta ggttgtatgt    22120
taattaccta caactcagtt tcaactgtgc ttaaaggagg aaatgactca tttcttgcta    22180
catatcaaat tagcccaaaa tgtagtggct taaaacaaca catttatgat ttctcagttt    22240
ttgcgtgtca ggaatttgga agcagcacag ctagacggtt ccagctcagg gtctctcatg    22300
aagttgcaat caaaatattg gcaggagaga aaaacatatt ttcagaagct gcaggcatag    22360
gaagacttgg ctggggttga aggatccact tccaagatgg cgcactcagt ggctcttggc    22420
tggaggcctc agttccctgc tgcgtggagc tctccctcca gctgcttgag tggactcatg    22480
acatgcagct ggcctcccct ggagcagtcg atccaacaat gagcatggcc atgaactagg    22540
ctcagaagcc actccctgtc gtctctacat tttcctatca gaagcaagtc attaaaagtc    22600
cagtgccact ccaggggaga cgaattaggc tctgccttct gaaaggatta tcacagaaga    22660
tgcggtccta tattcttttt ttaaaattat tcttttttttt attttgtaga gatggggtct    22720
tggtatgttg cctaggccag tctggaattc ctgggctcaa acaatcctgt ctctgcctcc    22780
caaagtgttg ggattacagg catgagccac tgcacctggt catgtggtca tatttctttt    22840 ttctttttttt ttttttttg agacagagtc tctgtcgccc aggctggagt atggtggcgt    22900
gatctcagtt cactgcagcc tccgcctccc gggttcaagc gattctcctg cctcagcctc    22960
ctgagtagct gggattacag gcgcccgcca acatgcccag ctaattttt tagtagagat    23020 ggggtttcac catgttagcc aggatggtct cgatctcctg atttggtgat ccgcccacct    23080
tggcctccca aagtttcaac catcgatcag aacttattga tgtacttatg tagctaggca    23140
cggtggcgcg tgcctgtaat cccagctact tggaagggtt aaggcaggag aatcgcttga    23200
acctgggagg cagaggttac agtgagtcaa gatcatacca ttgcactcca gtctgggcaa    23260
cagaatgaga ctctgtctca aaacaaaaa acaaaccctt gtatgtgatt ttcctggata    23320
gcatctgtta catcttcaca aagataaaaa gtcagacttg gctgggcatg gtggctcaca    23380
cctgtaatcc cagcactgag aggctgaggc aggcagatca cttgaggtca ggaatttgag    23440
accaggctgg gcagcatggt gaaacccccgt ctctacaaaa aatacaaaaa ttagccgggt    23500
gtggtgtcac gcacctgtat tcccaagcta ctcaggaagc taaggcagga gaatcacttg    23560
aacccagagg tggaggtttg cagtgagttg agattgtgcc attgcactcc agcctgggcg    23620
acagagtgag actctgtgtc aaaaataaaa taaaataaaa ttttaaaaaa ggcagatttt    23680
tttttcttct tggtattgtt accttattat agtaataata agtgcatagt gcatgctgag    23740
ataagcaatc ataatttgtt attgcggccg ggcatggtgg ctccagccta taatcccagc    23800
actttggtca ggagttcaag gccagcctgg ccaatatagt gaaactccat ctctactaaa    23860
atacaagaaa ttacctgggc atggtggcag ttgctggtga tccccagcta cttgggaggc    23920
tgaggcagga gaatcgcttg aacctgggaa gcagaggttg cagtgagcca agattgcacc    23980
actgcactcc agcctgggtg acagagtgag actctgtctg aaaataataa taataataat    24040
ttgttattgc ttttattgcc ttagtttaca tagggaatca aagtttatac tttgatttat    24100
aaaagttgct ttgattctag ttcacagaac cagaatcttt catataaagg tattagaggg    24160
cccagtgtgg tggctcatgc ctgtaatccc agcatattgg gaggctgagg agggaggatc    24220
actttaggag tttgaggcca gcctaggcaa catagtgaga ccttgtctct acaaaaaatt    24280
ccaacattag ctgggcatgg tggcatgtgc ctgtagtccc atttatttgg ggggctgagg    24340
```

```
caggaggatc acttgagccc acgaggttca atccaggttg cagtaagcca tgatcctgcc    24400
actgcactcc agtttgggta acagagcgaa gctatgtctc aaaaaaagaa aaaaaaagta    24460
ttctaaatcc aaatttaata tataaaacta aatgcaggcc aagtgtggtg gcatatacct    24520
ataatcacaa cactttggga ggctgaggtg ggaggattgc ttgagcccaa gagttcaaga    24580
ccagcctagg taacacagta agaccccatc tctacaaaaa gtagaaaaat tagcctggca    24640
tggtggtgag tgcttttaat cccaactact taggggctg agatgggaag attgcttgag     24700
cctcagagtt tgaggctgca gtgggccgtg atcgctccac tgatcgctct aaagtgagac    24760
cctgtctcaa aaaaaagaa aatagaagaa aactaaatac attcaataag actttgatct     24820
cttttccaag gtgtaaatat attttgggaa attttccagt tactttgttc tcattttaat    24880
gtaataatct aagtcttggt tttctaagga aaagttttct cttattatat cttttgttaa    24940
tgtttctctc ccatttcttt tgatctgatc ttcagataca tgattatctt cactgctaaa    25000
tttgtgttct ctggcctcta catttataat ttctcataat tctttatcta agtatttctt    25060
ccctacctac tgaagaaaac tcaagttttc ttccaccta atgattatgc tgtgtctgtg     25120
agttttcttc atgactcttt acagtacaag ttttttgttt ttgtttttt aatggtcaga    25180
tggatagaac aacacaggtt ttgtttgttt tgttttaact tttaaaaaaa ttataataga    25240
taaagggtct cactacgttg tccaggctga tctcatactc ctgggctcaa gcaatccacc    25300
cacctctgcc tcccaaagtg ctgggattac agtcatgagc caacatgcct gggcagtaca    25360
ggttttttt gagacggagt tttgttcttg ttgccgaggc tggagtgcaa tggcacaatc     25420
ttggctcacc acaaagtctg cctcccaggt tcaagtgatt ctcctgcctc agcctcctga    25480
gtagctggga ttacaggcat gtgccaccac gcccagctaa ttttgtattt ttagtagaga    25540
cggggtttca ccatgttggc caggctggtt tcgaactgct gacctcaggt gatctgccca    25600
cctcggcctc ccaaagtgct gggattacag gcatgagcca ccatgccag ctgtagtaca     25660
ggttttaata tgctaaatac tcttccttc tttattaatg tgcatggaag ttctaatatt     25720
tttttcccat accccagaga gtccatattt tggaatcaac aacactagcc tttgttgaca    25780
agtgtctctc ttgggttcct tctttgtgtc ctccactgaa ttttgggtt cataaaattt     25840
catttgttgt gcttgcttaa ttccctggga atcagactgt tcctgatcgg atgacatttc    25900
tggttaattc tttagttggc aggaaataga cacaggaaac gtggtcagtt tctgattctg    25960
gcgttgagag accctttctc cttttcctct ctctcag tg  ggc gac aga tgc gaa      26014
                                            Val Gly Asp Arg Cys Glu
                                                                 5
aga aac gag ttc cag tgc caa gac ggg aaa tgc atc tcc tac aag tgg      26062
Arg Asn Glu Phe Gln Cys Gln Asp Gly Lys Cys Ile Ser Tyr Lys Trp
     10              15                  20
gtc tgc gat ggc agc gct gag tgc cag gat ggc tct gat gag tcc cag      26110
Val Cys Asp Gly Ser Ala Glu Cys Gln Asp Gly Ser Asp Glu Ser Gln
 25                  30                  35
gag acg tgc t gtgagtcccc tttgggcatg atatgcattt attttgtaa             26160
Glu Thr Cys
 40
tagagacagg gtctcgccat gttggccagg ctggtcttga atttctggtc tcaagtgatc    26220
cgctggcctc ggcctcccaa agtgctggga ttacaggcac cacgcctggc ctgtgacacg    26280
attcttaacc ccttttttgat gatggcggct ggaaaagtgg ccagtggatt ttgatgtatt   26340
caatcatgaa ttaggaggtg gggagagaat gaattattgg agctttcctt aaagccatta   26400
aatggctcta ttgtttttttc aattgatgtg aatttcacat aacatgaaat taaccagctc   26460
```

```
agtggcatta atacatctgc aatgctgtgt ggccaccacc tctatcttgt tccaaaactt   26520
tgcataacct aatgtctttt ttttttttt tttttgagac ggagtctcgt tccatcaccc    26580
aggctggagt gcagtggtgt gatctcagct cactgcaacc tccgcctccc aggttcacgc   26640
catcctcctg cctcagcctc ccgagtagct gggactacag gcaccctcca ccacatccgg   26700
ctaatttttt gtatctttag tagagatggg gtttcaccat gttagccggg atggtctcga   26760
tctcctgacc tcgtgatcca cctgcctccg cctcccaaag tgctggcatt acaggcgtga   26820
gccaccatgc ccggcctatt ttttttttta agagatggag tctaattctg ttgcccaggc   26880
tggagtccag tggtaccatc atacttcact gcagccttga cctcttgggc tcaagtgatt   26940
ctcttgcctc gaactcccaa agtattggga ttacaggtgt gagccaccgc actcagccta   27000
atgtccagtt tttaacaagc tccatttaaa tgccctccgt tttgacccat aaaggggtag   27060
gcttggccgg gcacaatggc ttgtgtctgt agtcccagct acttgggagg ctgaggcaga   27120
aaggcagaaa gattgcttta taaagcccag gagtttgagg gccacctggg tggcatagct   27180
agacctcatc tctaaaaaat aagtaataaa taaatatttg ttttgtttt ttctttttc    27240 ttttcttttt ttttttttt tgagacggag tcttgctctg ttgcccaggc tggagtgcag   27300
tggcgcgatc tcagctcact gcaagctgtg cctcctgggt tcatgccatt ctcctgcctc   27360
agcctcccga gtagctggga ctacaggcgc ccactaccac gcccagctaa ttttttgtat   27420
ttttagtaga gatggggttt caccacgtta gccaggatgg tctcaatctc ctgacctcgt   27480
gatccgccag ctttggcctc ccaaagtgtt gggattacag gcgtgagcca ctgagcccgc   27540
cccatatgta tgtatatata tattttttta aaatgggaga ccaggcatgg tggctcatgc   27600
ctagaatccc agcactttgg gaagctgagg taggcggatc acttgaggcc atgagtttga   27660
gaccagcctg ctcaacatga tgaaacttct atctctacta aaaaaaaaag tgggattagg   27720
tcaggcacgg tggctcacac ctgtaatccc agcactttca gaggccgagg caggaggatc   27780
atgaggtcag gagatcgaga ccatcctggc taacacggtg aaaccccgtc tctactaaaa   27840
aaatacaaaa aattagccag gcgtggtggc gggtgcctgt agtcccagct actcaggagg   27900
ctgaggcagg agaatggcgt gaacccggga ggcggagctt gcagtgagcc aagatcgtgc   27960
cactgtactc cagcctgggc gacagagcaa gactctgtct caaaaaaaaa aaaaaagtg   28020 ggattgacat tctcttcaaa gttctggggt tttccttgc aaagacagga ttggcaaggc   28080
cagtgggtct tttttgtgtg tgtgtgtgtg acggagtctc actctgccac ccaggctgga   28140
gtgcaatggc aggatctcgg ctcaccgcaa cctcctcctc ccaggttaaa gtgattctcc   28200
tgcctcagcc tcccgagtag ctgggactac aggtgcccgc caccacaccc aactaatttt   28260 tgtatttta gtagagacag ggtttcacta tattggccag gctggtcttg aacccctgac   28320
ctcacgtgat ccaccgcct tggcctccca aagtgctggg attacaggcg tgagccactg   28380
tgctcggcct cagtgggtct ttcctttgag tgacagttca atcctgtctc ttctgtag    28438 tg   tct gtc acc tgc aaa tcc ggg gac ttc agc tgt ggg ggc cgt gtc     28485
     Leu Ser Val Thr Cys Lys Ser Gly Asp Phe Ser Cys Gly Gly Arg Val
               45                 50                  55 aac cgc tgc att cct cag ttc tgg agg tgc gat ggc caa gtg gac tgc     28533
Asn Arg Cys Ile Pro Gln Phe Trp Arg Cys Asp Gly Gln Val Asp Cys
     60                  65                  70 gac aac ggc tca gac gag caa ggc tgt c gtaagtgtgg ccctgccttt         28581
Asp Asn Gly Ser Asp Glu Gln Gly Cys
 75                  80 gctattgagc ctatctgagt cctggggagt ggtctgactt tgtctctacg gggtcctgct   28641
```

```
cgagctgcaa ggcagctgcc ccgaactggg ctccatctct tgggggctca taccaagcct   28701
cttccgccct tcaaatcccc ccttgaccag gaggcattac aaagtgggga tggtgctacc   28761
tcttcgggtt tgtcacgcac agtcaggag gctgtccctg ccgagggcta gccacctggc    28821
acacacactg gcaagccgct gtgattcccg ctggtcgtga tccccgtgat cctgtgatcc   28881
ccgccccgtg aggctgaaca catagtgacg cttgctagcc aagcctcaat gacccacgta   28941
acatgaaggg ggaaaagcca gaaagttctg ccaaggagca aggccaagaa tcccgaaggg   29001
aaatggactt tgaagctggg cgtcttcttg gctgtcttaa tacaagtggc acatccaaat   29061
ccaaaacccc gaaattcaaa gtcttgagca cccgaaattc tgaaacgtct tgagcactga   29121
cctttagaag gaaatgctta ttggagcatt ttggatttcg gattttttacc actgagtgtg   29181
gagtcctaat taggaaaaaa accaggctga ccgaaccaaa ggaaagcaat aaaagaaggc   29241
agatagggtc aggcacggtg gctcacccct gtaatcccag ccttttgaga ggctgaggcg   29301
ggtggatcac ttgaggtcag gagttcgaga gcagcctggc caacacgtg aaacccccatc   29361
tctactgaaa atacaaaaac tagccaggta tggtggcgtc tgcctgtaat cccagctact   29421
cgggaggctg agacaggaga atcacttgaa cctgggaggc agaggttgca gtgagccaat   29481
atcacgccat tgcactccag cctgggggac aagagcgaaa ttctgtctca aaaaaaaga   29541
agaagaaggc cgacaaacta tgtaactctg cctttctcca tggtccagaa cacacagccc   29601
tcctgcgtaa ataactcctt atcttcctgc tcccagctat catcagacac ctcggctgat   29661
agaaaattgc aagttagctc actgcaacct cggcattata agtactgcac aaagccctct   29721
tcagcgcaca gcacaagcac cattctataa aatctccagc aagcggccag gtgcagtggc   29781
tcatacctgt aatcccagca ttttgggaga ctgaggcggg cggatcacct gaggtcagga   29841
gtttgagacc agcctggcca acatggtgaa accccgtctc tattaaaaat acaaaaaaat   29901
tagccaggcg tggtggcagg tgcctgtaat cccagctact tggaaggctg aggcaggaga   29961
atcgcttgaa cccgggaggt ggaagttgca gtgagccgag atcttgccat cgcactccag   30021
cctggggac aagagtgaga cttcgtctca aaaaaaaaa aaaaaattcc cagcaagcct    30081
ttgtcttctg gcagtcagct cctctcttgc tgacctgctc attgctttct tgcaaggtat   30141
tttcctacct actttctgga ataaatctgt cttctgtac ttacaactac cttttttaaa    30201
atttctttct tttttgagat ggagtctcac tctgtttgcc caggctggag ttcagtggtg   30261
caatctcagc tcactgcaac ctctacctac tgggttcaag cgattctcct gcctcagctt   30321
cccgagtagc tgggattaca ggcgtgcacc agcacgcagg ctaatttttg tatttttagt   30381
agagacgggg tttcaccatg ttggccaagg tggtcttgaa ctcctgacct caagtgatcc   30441
tcccacctca gcctcccaaa gcgctaggat tacggccatg agccactgag gccggctgca   30501
cctacaactg tcttgataaa ttcttacccc cacaccactg gtccagatag tcagtgctca   30561
cccacaacat taaggatatt ccaaatttga acattccaa atcagaaaa atattccaac    30621
tctgaaaata ttccaaaatc caaaaaaatt caaaatccaa aacacttctg gtcccaagca   30681
ttttagagaa gggatactca acccaaaata aggacagcaa ttctataaat tgtgctacca   30741
tcttgcaggt ctcagtttaa cagctttaca cctattagcg caccagtgct catagcagtg   30801
ctgggaaatg tgtacagatg aggaaactga ggcaccgaga gggcagtggt tcagagtcca   30861
tggcccctga ctgctcccca gcccgccttt ccaggggcct ggcctcactg cggcagcgtc   30921
ccggctata gaatgggctg gtgttgggag acttcacacg gtgatggtgg tctcggccca   30981
tccatccctg cag cc  ccc aag acg tgc tcc cag gac gag ttt cgc tgc      31029
                Pro Pro Lys Thr Cys Ser Gln Asp Glu Phe Arg Cys
```

```
                   85                  90                  95
cac gat ggg aag tgc atc tct cgg cag ttc gtc tgt gac tca gac cgg       31077
His Asp Gly Lys Cys Ile Ser Arg Gln Phe Val Cys Asp Ser Asp Arg
            100                 105                 110 gac tgc ttg gac ggc tca gac gag gcc tcc tgc ccg gtg ctc acc tgt       31125
Asp Cys Leu Asp Gly Ser Asp Glu Ala Ser Cys Pro Val Leu Thr Cys
        115                 120                 125 ggt ccc gcc agc ttc cag tgc aac agc tcc acc tgc atc ccc cag ctg       31173
Gly Pro Ala Ser Phe Gln Cys Asn Ser Ser Thr Cys Ile Pro Gln Leu
    130                 135                 140 tgg gcc tgc gac aac gac ccc gac tgc gaa gat ggc tcg gat gag tgg       31221
Trp Ala Cys Asp Asn Asp Pro Asp Cys Glu Asp Gly Ser Asp Glu Trp
145                 150                 155 ccg cag cgc tgt agg ggt ctt tac gtg ttc caa ggg gac agt agc ccc       31269
Pro Gln Arg Cys Arg Gly Leu Tyr Val Phe Gln Gly Asp Ser Ser Pro
160                 165                 170                 175 tgc tcg gcc ttc gag ttc cac tgc cta agt ggc gag tgc atc cac tcc       31317
Cys Ser Ala Phe Glu Phe His Cys Leu Ser Gly Glu Cys Ile His Ser
            180                 185                 190 agc tgg cgc tgt gat ggt ggc ccc gac tgc aag gac aaa tct gac gag       31365
Ser Trp Arg Cys Asp Gly Gly Pro Asp Cys Lys Asp Lys Ser Asp Glu
        195                 200                 205 gaa aac tgc g gtatgggcgg ggccagggtg ggggcgggc gtcctatcac              31415
Glu Asn Cys
    210 ctgtccctgg gctcccccag gtgtgggaca tgcagtgatt taggtgccga agtggatttc    31475 caacaacatg ccaagaaagt attcccattt catgtttgtt tctttttttt cttttctttc    31535 tttattttgt ttttgagatg gagtctcact ctgtgatttt tttcatctct aaatttccta    31595 catccatatg gccaccatga ggccccaggc tggccgatgg ttgctgttag cttattggga    31655 aatcactgtt tggaaggtgc tggttgtttt ttgttgtttg ttgttttgt ttttgttttt    31715 gttttgagac ggagtctcgc tctgtcgcca gggtggagtg cagtggcgcg atcagctcac    31775 tgcaacctcc gcttcctggg ttcaagccat tctcctgcct cagcctccca agtagcgcgg    31835 attacaggca tgtgccacca cctccggcta ttttttttc tatttagtag agatgggtt     31895 tcaccatgtt agtcaggctg tcatgaact cttgacctca ggtgatccac ccgcctcggc    31955 ctcccaaagt gctgggatta caggcgtgca ctgctgcacc cagccttttt ttgttttttt    32015 gagacagggt cttgctgtca cccaggttga agtaaggtgg cacgattatg gctcactgcg    32075 gccttgatct ccttggctca agcgatcctc tcacttcagc ctctcaagca gttggaacca    32135 caggctgtac caccaagcct ggccaatttt tttgtacaga cacaggctgg tcttgaactc    32195 ctgggctcaa gcaatcctcc tgccttggcc tccaaagtg ctgggattcc aggcatgagc    32255 cgctgcaccc ggcaaaaggc cctgcttctt tttctctggt tgtctcttct tgagaaaatc    32315 aacacactct gtcctgtttt ccag ct  gtg gcc acc tgt cgc cct gac gaa       32365
                         Ala Val Ala Thr Cys Arg Pro Asp Glu
                                         215 ttc cag tgc tct gat gga aac tgc atc cat ggc agc cgg cag tgt gac      32413
Phe Gln Cys Ser Asp Gly Asn Cys Ile His Gly Ser Arg Gln Cys Asp
220                 225                 230                 235 cgg gaa tat gac tgc aag gac atg agc gat gaa gtt ggc tgc gtt aat g    32462
Arg Glu Tyr Asp Cys Lys Asp Met Ser Asp Glu Val Gly Cys Val Asn
            240                 245                 250 gtgagcgctg gccatctggt tttccatccc ccattctctg tgccttgctg cttgcaaatg   32522
atttgtgaag ccagagggcg cttccctggt cagctctgca ccagctgtgc gtctgtgggc   32582
```

```
aagtgacttg acttctcaga gcctcacttc cttttgtttt gagacggagt ctcgctctga  32642
cacccaggct ggagtgctgt ggcacaatca cagctcacgg cagcctctgc ctctgatgtc  32702
cagtgattct cctgcctcag cctcccgagt agctgagatt aaaggcgtat accaccacgc  32762
ccggctaatt ttttgtattt ttattagaga cagggtttct ccatgttggc caggctggtc  32822
ttgaactcct ggtctcaggt gatccacccg cctcggcctc ccaaagtgct aggattacag  32882
gtgtgagcca ctgcgccagg cctaattttt ttgtatttt agtagagatg cggttttgcc  32942
atattgccca ggctggtctc gaactcctgg gctcaagcga tctgcctgcc ttggcctccc  33002
aaagtgctgg gattacaggc acaaccacc gtgcccgacg cgttttctta atgaatccat  33062
ttgcatgcgt tcttatgtga ataaactatt atatgaatga gtgccaagca aactgaggct  33122
cagacacacc tgaccttcct ccttcctctc tctggctctc acag tg   aca ctc tgc     33177
                                                  Val Thr Leu Cys
                                                              255
```

```
gag gga ccc aac aag ttc aag tgt cac agc ggc gaa tgc atc acc ctg     33225
Glu Gly Pro Asn Lys Phe Lys Cys His Ser Gly Glu Cys Ile Thr Leu
            260                 265                 270 gac aaa gtc tgc aac atg gct aga gac tgc cgg gac tgg tca gat gaa     33273
Asp Lys Val Cys Asn Met Ala Arg Asp Cys Arg Asp Trp Ser Asp Glu
        275                 280                 285 ccc atc aaa gag tgc g gtgagtctcg gtgcaggcgg cttgcagagt ttgtggggag    33329
Pro Ile Lys Glu Cys
            290
```

```
ccaggaaagg gactgagaca tgagtgctgt agggttttgg gaactccact ctgcccaccc  33389
tgtgcaaagg gctccttttt tcattttgag acagtctcgc acggtcgccc aggctggagc  33449
gcaatggcgc gatcttggct caccacaacc tccggctccc aggttcaagc gattcttctg  33509
cctcagcctc ctgagtagct gggattacag ctgaatgcca ccttgctggg ctaattttg  33569 tattttagt agagatgggg tttcaccatg ttggccaggc tggcctcgaa ctcctgacct  33629
cgagtgatct gcccgcctcc tgaagtgctg ggattacagg cgtgagccac ctcgtcctgg  33689
tgagggtttt ttttttttccc caaccctctg tggtggatac tgaaagacca tattaggata  33749
actgtacagt atagagaagg cagtggcaag ttttctctgt catataccag agtgggcttg  33809
ggcatggtgg catactcctg tagtctcagc taatcaggag gctgaggaag gaggatcgct  33869
tgggcccagg agttggagac tgtagtgagc tgtgatcaca ccaccacact tcaatctggg  33929
caacagagca agagaccta tctctaaaaa aaagtaagta tttcggacac tgtgggccat  33989
acggtctctg gtgcagtttc tcaacatggc tgttgggtga acacaaccac gcacagaacg  34049
caaaccaata cacgtggctg tgggcccaga aaatgttatt tatggacaca aaaattggaa  34109
tttcatataa ctgttttgtg tcatgaaaat gatttcccctt tttattttta tttttcttct  34169
caagtattta aatatgtaaa agccatttt aggcctggca ggatggttca cagctgtaat  34229
cccagcactt tgggaggtcg aggcgggagg atcacgaggt caggagatcg agaccatcct  34289
ggccaacaca gtgaaacccc gtctctacta aaaatacaaa aaattaacca ggcttggtgg  34349
cgcgcgtctg tagtcccagc tgctcaggag gctgaggcag gagaatcgct tgaatgcagg  34409
aggcggaggt tgtagtgagc cgaggttgca ccactgcact ccagcctgag cgacagagtg  34469
agagtccgcc tcaaacaaaa aaatgtttgc ccatgctggt cttgaactcc tgggctcaag  34529
ctatctgcct gccttggtct cccaaagttc tgggattaca ggcatgagct acagcgcccg  34589
gacttttgtt gttttatatc tatatatcta tatataactt gttttatgta tatatataac  34649 ttgtttata tatacata aactgcagta aaaaacatgt aacataaaat ttaccttctc  34709
```

-continued

```
aaaccttatt aagtgcacag ttctgtgcca ttagcaaatt cacactgttg tacaacatca   34769
caaccaccat ctccagaact ttttttttt tttttattct ttttgagaca gagtctcact    34829
cgtcgcacgg gctggagtgc agtggtgcga tctcggttca ctgcaacctc cacctaccag   34889
gttcaagcaa ttctcctgcc tcagcccct cagtagctgg gattacaggt gcccgtccta    34949
ccacgcccag ctaatttttg tatttcagt agagactgac tgggtttcac catgttggcc   35009
aggctggtct cgaactcctg acctcaagtg atcctcccac ctcagcctcc caaagtgctg   35069
ggaatacagg catgagccac tgcgcccggc ccagaactc ttttatcttc ccaaactgaa    35129
gctctgtccc catgaaacac tcactctcca tcccctcccc aactcctggc acccaccatt   35189
ctactttctg tccctatgaa tgtgatggct ctagggacct cctctgagtg aatcagaca    35249
gcattttcct tttttgactg gcttatttca ctgagccaag tgcggtggca cacgcctgta   35309
atcccaaaac tttgggagac cgaggcgggc gcatcaccag aggacaggag nncgagacca   35369
gcccggccaa caggggaaa ccccatcact agggagcctg cagaaagaaa gccaccacat    35429
ggcctgctgg agccacacaa tcccagcaaa acagggacgc taaacgtagg agaaacacac   35489
aaccccagga ggcggaggtc gcagtgagcc gagatcgtgc cattcactc cagcctgggc     35549
aacaagagtg aaactccgtc tctcctaaaa atacaaaaaa attagctggg catggtggca   35609
catgcctgta gtcccagcta cttgggaggc tgaggcagga aatcacttg aacccgggag    35669
gtggaggttg taatgagcca aggttggcgg cgaagggatg ggtaggggcc cgagagtgac   35729
cagtctgcat cccctggccc tgcgcag gg  acc aac gaa tgc ttg gac aac aac   35782
                                  Gly Thr Asn Glu Cys Leu Asp Asn Asn
                                      295                 300 ggc ggc tgt tcc cac gtc tgc aat gac ctt aag atc ggc tac gag tgc    35830
Gly Gly Cys Ser His Val Cys Asn Asp Leu Lys Ile Gly Tyr Glu Cys
    305                 310                 315 ctg tgc ccc gac ggc ttc cag ctg gtg gcc cag cga aga tgc gaa        35875
Leu Cys Pro Asp Gly Phe Gln Leu Val Ala Gln Arg Arg Cys Glu
    320                 325                 330 ggtgatttcc gggtgggact gagccctggg ccccctctgc gcttcctgac atggcaacca   35935
aaccctcat gcctcagttt ccccatctgt taagtgtgct tgaaagcagt taggagggtt    35995
tcatgagatt ccacctgcat ggaaaactat cattggctgg ccagagtttc ttgcctctgg   36055
ggattagtaa ttaagaaatt tcaggccggg tgcgtaatcc ctgtaatccc aacaccttgg   36115
gacgccgagg cgggcagatc acctgaggtc gggagttcca gaccagcctg accaacatgg   36175
agaaaccccg tctctactaa aaatacaaaa ttagccgggc ttggtggtgc atgcctaaa    36235
tcccagctac tcaggaggct gaggcaggag aatcacttga acctgggagg tggaggttgt   36295
ggtgagccaa gatcgtgcca ttgcactcca gcctgggcaa caagagtgaa actccatcca   36355
aaaaaaaag aaaagaaaag aaaaaaaga aagaaattt cagctgacac agcttcacac     36415
tcttggttgg gttcccgtgg tgaatgatga ggtcaggtga tgactgggga tgacacctgg   36475
ctgtttcctt gattacatct cccgagaggc tgggctgtct cctggctgcc ttcgaaggtg   36535
tgggttttgg cctgggcccc atcgctccgt ctctagccat tggggaagag cctccccacc   36595
aagcctcttt ctctctcttc ca gat atc gat gag tgt cag gat ccc gac acc    36647
                        Asp Ile Asp Glu Cys Gln Asp Pro Asp Thr
                            335                 340 tgc agc cag ctc tgc gtg aac ctg gag ggt ggc tac aag tgc cag tgt    36695
Cys Ser Gln Leu Cys Val Asn Leu Glu Gly Gly Tyr Lys Cys Gln Cys
    345                 350                 355 gag gaa ggc ttc cag ctg gac ccc cac acg aag gcc tgc aag gct gtg g  36744
Glu Glu Gly Phe Gln Leu Asp Pro His Thr Lys Ala Cys Lys Ala Val
```

```
                360                  365                  370
gtgagcacgg gaaggcggcg ggtggggggcg gcctcacccc ttgcaggcag cagtggtggg   36804
ggagtttcat cctctgaact ttgcacagac tcatatcccc tgaccgggag gctgtttgct   36864
cctgagggct ctggcagggg agtctgccgc cctgttagga cttgggcttg ccaggggggat  36924 gcctgcatat gtcctagttt ttgggaatat ccagttaacg gaaccctcag ccctactggt   36984
ggaacaggaa ccggctttcc tttcaggggac aacctgggga gtgacttcaa ggggttaaag  37044
aaaaaaaatt agctgggcat ggtgccacac acctgtggtc ccagctactc agaaggctga   37104
ggcgggagga ttgcttgagg gcaggaggat tggttgatcc tcccacctca gcctccggag   37164
tagctgggac ctcaggtgca tgccactatg cctggctaat tttctttttt cttttttttt   37224 tttttttcgag acggagtctc gctctgttgc ccaggctgga gtgcagtggc aggatctcgg   37284
ctcactgcaa gctccgcctc ccgggttcac gccattctcc tgcctcagcc tccccagtag   37344
ctgggactac aggagcccgc cactgcacca ggccaatttt tttgtatttt tagtagagac   37404 ggggttttcac tgtgttagcc aggatggtct cgatctcctg acttcgtgat ccgcccacct  37464
cggccttcca aagtgctcgg attacaggcg tgagccactg cgcccagccg ctaattttca   37524
tatttttagt aaaaacaggg tttcaccatg ttggccaggc tagtcttgaa ctcctgaacc   37584
caagtgatcc tcctgccttg gcctcccaaa gtgctgggat tacagacacc acacctggct   37644
attattattt tttagagaca gggtgctgct ctatcttcca gcctgtagtg cagtgcagcc   37704
tccatcatag ctcgctgcag ccttgacctc ctgggttcac gtgatcgtcc cgcctaagcc   37764
tctggaggag ctgggagtac tggcatgtgc caccatgcct ggttaatttt tttttttttt   37824
tttttgagac agagtctcat tctgtcaccc aggctgagt gcggtggtgc gatcttggct    37884
tactgaaacc tccacctccc aggttccagc aattctcctg cctcaccctg ctgagtagct   37944
gggattacag gttccggcta ccaaacctgg ctagttttg tatgtttagt agagacaggg    38004
tttcaccatg ttggtgaggc tggtctcgat tctcccgcct cagcctccca aagtgctggg   38064
attacaggct tgagccaccg tgcctggctt tttttttttt tttttttttt gtggcaataa   38124
ggtctcattg tcttgcccag gctagcctta tgctcctagc ctcaagtgat cctcctcccc   38184
cagcctccca aagtgctggg attacaggtg gcgccactg tgcctgttcc cgttgggagg   38244
tcttttccac cctcttttc tgggtgcctc ctctggctca gccgcaccct gcaggatgac    38304
acaaggggat ggggaggcac tcttggttcc atcgacgggt cccctctgac ccctgacct    38364 cgctccccgg accccccag gc  tcc atc gcc tac ctc ttc ttc acc aac cgg    38414
                         Gly Ser Ile Ala Tyr Leu Phe Phe Thr Asn Arg
                                375             380             385 cac gag gtc agg aag atg acg ctg gac cgg agc gag tac acc agc ctc     38462
His Glu Val Arg Lys Met Thr Leu Asp Arg Ser Glu Tyr Thr Ser Leu
            390             395             400 atc ccc aac ctg agg aac gtg gtc gct ctg gac acg gag gtg gcc agc     38510
Ile Pro Asn Leu Arg Asn Val Val Ala Leu Asp Thr Glu Val Ala Ser
        405             410             415 aat aga atc tac tgg tct gac ctg tcc cag aga atg atc tgc ag          38554
Asn Arg Ile Tyr Trp Ser Asp Leu Ser Gln Arg Met Ile Cys Ser
    420             425             430 gtgagcgtcg ccctgcctg cagccttggc ccgcaggtga gatgagggct cctggcgctg    38614
atgcccttct ctcctcctgc ctcag c acc cag ctt gac aga gcc cac ggc gtc   38667
                                Thr Gln Leu Asp Arg Ala His Gly Val
                                            435             440 tct tcc tat gac acc gtc atc agc aga gac atc cag gcc ccc gac ggg    38715
Ser Ser Tyr Asp Thr Val Ile Ser Arg Asp Ile Gln Ala Pro Asp Gly
```

```
                    445             450             455
ctg gct gtg gac tgg atc cac agc aac atc tac tgg acc gac tct gtc    38763
Leu Ala Val Asp Trp Ile His Ser Asn Ile Tyr Trp Thr Asp Ser Val
        460             465             470 ctg ggc act gtc tct gtt gcg gat acc aag ggc gtg aag agg aaa acg    38811
Leu Gly Thr Val Ser Val Ala Asp Thr Lys Gly Val Lys Arg Lys Thr
    475             480             485 tta ttc agg gag aac ggc tcc aag cca agg gcc atc gtg gtg gat cct    38859
Leu Phe Arg Glu Asn Gly Ser Lys Pro Arg Ala Ile Val Val Asp Pro
490             495             500             505 gtt cat ggg tgcgtatcca cgacgctgag ggctgcagag ggaatggagg            38908
Val His Gly gagcaggaag gagcttcagg aactggttag tgggctgggc atggtggctc aaagcacctg  38968
taatcccagc actttgggag gccaaggtgg gtggatcatc aagaccagcc tgaccaacat  39028
ggtgaaacct cgtctctact aaaaatacaa aaattagccg ggtgtggtgg tgggcacctg  39088
taatcccagc tgctcgggag gctgaggcag gagaatcact tgaacctggg agatggaggt  39148
tgcagtgagc caagacagcc ccactgcact ccagcctggg tgacagagtg agactccgtc  39208
tcaaaaaaaa aaaaaaaaac taaacaaaaa actggttagt ggctagacaa caggatggta  39268
tcttccaagc ccatggctga ctcagcagct cctgggtcaa gacactgtga cctgtgtccc  39328
ctggcaggaa gcatcgcccc tgccacctgc cggtgtact ctgtacctgt caggtgacat   39388
ctgctaccta agcacgtgag aggtggcatt tcacagtttc agtgtggtgc tgacaacccg  39448
ggacgcacac tgtccttgca gctacaatca ggaggtgaat gttgggtttc agcagagaa   39508 cactggagaa ggcacacttg gtgtctggaa gggaaaagca gggaagagag catcatcaga  39568
tgcctgcggg tgaaggtggg cccgctatgg ccagcgtccc ttttatttt tatttattta   39628 tttatttgag atggaatctc gctctgtcgc ccagactgta gtgcagtggt gcgatcacgg  39688
ctcactgcaa gctccgcctc acaggttcac gccattctcc tgcctcagcc tcccgagtag  39748
ctgggactac aggcacccgc caccacgccc ggttaatttt ttgcattttt attagagacg  39808
gggtttcacc gcgttagcca ggatggtcta atctcctga ccctgtgatc cacccgcctc   39868
ggcctcccta agtgcttgga ttacaagcgt gagccaccac gcccggcccc cttttatttt  39928
tttatttttt gagacggagt ctcgctctgt cgcccaggct agattgcagt ggcgtgatct  39988
cggctcactg cagcctccgc ctcccaggtt caagtgattc tcctgcctca acctcccaac  40048
taattaggat tacaagcatg taccaccatg cctgactaat tttttgtatt tttagtagag  40108
actgggtttc accatgttgg ctaggctggt ctcgaaccct tagcctcaag taatctgcct  40168
gcctcagcct cccaaacagc ggggattaca ggcatgagcc actgtgccca acccaaccct  40228
ggatctcttt taaacaagac aatgctcgct gttgccacag aacaatgggt ggggtacatg  40288
tggcccagtg tgtttggcca cataactgcc aggccagagg gaaagagact ctcagactgt  40348
ctccactcag atacaaatgt gtgtgttgtg tgcgtgtgtt ctggtctcat atttgtttgt  40408
tttgagacag ggtgtcgctc tgtcactgag tctggagtgc agtggcgcaa tcagagttca  40468
ctgcagcctc aaactcttgg gctcagttga ttctcccact tcagcctccc aagtagctgg  40528
aactacaggt gaacaccact gtgcccagct aatttatttt attttagta gagatgaggt   40588 ctcactatgt tgcccaggct ggtcttgacc tcctagcctc aagcaatcct cctgccttgg  40648
tctcccaaag tgctgggatt acacgtgcga gccattgcgc atggcttgtg ttcttgtgtt  40708
tcttcctttt tctttcgaga tggcgtctca gtctgccacc caggctggag tgcagtggtg  40768
tgatcatagc tcactgtagc ctcaacttcc tgggctcaag caatcctctt gatttcagcc  40828
```

```
tcccgggcct ggccagcatg gtgaaacccc gtctctacta aaaatacaaa aatgtagcca   40888
ggcgtggtgg tgggcgcctg taatcccagc tacaccagag gctgaggcag gagaatcgct   40948
tgagcctgga aggtggaggt tgcagcaagc caagatcgtg ccactgcact ccagcctggg   41008
caacagagac agactctgtc tcaaaaaaaa aaaaaaaaa cccaaacaag ccacatttgg    41068 agtttgggt tccagcagg actatttccc aagcctgagc ctggctgttt cttccagaat    41128
tcgttgcacg cattggctgg gatcctcccc cgccctccag cctcacagct attctctgtc   41188
ctcccaccag c ttc atg tac tgg act gac tgg gga act ccc gcc aag atc    41238
            Phe Met Tyr Trp Thr Asp Trp Gly Thr Pro Ala Lys Ile
                510             515                 520 aag aaa ggg ggc ctg aat ggt gtg gac atc tac tcg ctg gtg act gaa    41286
Lys Lys Gly Gly Leu Asn Gly Val Asp Ile Tyr Ser Leu Val Thr Glu
        525                 530                 535 aac att cag tgg ccc aat ggc atc acc cta g gtatgttcgc aggacagccg    41337
Asn Ile Gln Trp Pro Asn Gly Ile Thr Leu
        540                 545 tcccagccag ggccgggcac aggctggagg acagacgggg gttgccaggt ggctctggga   41397
caagcccaag ctgctccctg aaggtttccc tctttctttt ctttgttttt tcttttttg    41457 agatgaggtc ttggtctgtc acccaggctg gagtgcactg gcgcaatcgt agctcactgc   41517
agcctccacc tccaggctc aagtgatcct cctgcctcac cctcctgagt agctgagatt    41577
acagacacgt gccaccacgg cagactaatt ttattttatt tttgggaaga gacaaagtct   41637
tgttatgttg gcctggctgg tctcaaactc agggtgcaag cgatcctccc gcctcagcct   41697
tccaaactgc tgggattaca ggcgtgggcc accgtaccca gcctccttga agttttttctg   41757 acctgcaact cccctacctg cccattggag agggcgtcac aggggagggg ttcaggctca    41817
catgtggttg gagctgcctc tccaggtgct tttctgctag gtccctggca ggggtcttc    41877 ctgcccggag cagcgtggcc aggccctcag gaccctctgg gactggcatc agcacgtgac    41937
ctctccttat ccacttgtgt gtctag at  ctc ctc agt ggc cgc ctc tac tgg    41989
                              Asp Leu Leu Ser Gly Arg Leu Tyr Trp
                                   550                 555 gtt gac tcc aaa ctt cac tcc atc tca agc atc gat gtc aac ggg ggc    42037
Val Asp Ser Lys Leu His Ser Ile Ser Ser Ile Asp Val Asn Gly Gly
        560                 565                 570 aac cgg aag acc atc ttg gag gat gaa aag agg ctg gcc cac ccc ttc    42085
Asn Arg Lys Thr Ile Leu Glu Asp Glu Lys Arg Leu Ala His Pro Phe
        575                 580                 585 tcc ttg gcc gtc ttt gag gtgtggctta cgtacgagat gcaagcactt            42133
Ser Leu Ala Val Phe Glu
        590 aggtggcgga tagacacaga ctatagatca ctcaagccaa gatgaacgca gaaaactggt   42193 tgtgactagg aggaggtctt agacctgagt tatttctatt ttcttctttc tttttttttt   42253 ttttttgag acagagtttt gctctcgttt cccaggctgg agggcaatgg catgatctcg    42313 gctcaccgca acctccacct cccaggttca agtgattctc ctgtctcagg ctccccagta   42373 gctgggatta caggcatgca ccaccaccat gcccggctaa ttttgtattt ttagtagaga   42433 cggagtttct ccatgttggt caggctggtc tcgaactccc gacctcaggt gatctgcctg   42493 cctcggcctc ccaaagtgct gggattacag acttgagcca ccgcgcccag ctattttctgt   42553 tttcttttctt tcttcttctt cttttttttt ttctaagaga caggatctca ctctgtcccc   42613 aggcaggagt gcagtgctgt gatcatagct cactgcagcc ttaacctcct gggctcaagt   42673 gatcttccca cctcagcctc ccaagtagct ggaactacag gtgcacacca ccatgcccag   42733
```

```
ctcattttg  tatttttttt  tttttttgaga  cagtctcgtt  ctgtcacccc  ggctggagtg   42793
cagtggtaca  atcttggctc  actgcaacct  ctgcctccca  ggttcaagcg  attctcctgc   42853
ctcagcctcc  tgagtagttg  agattacagg  catgtgtgcc  atcatacctg  gctgattttt   42913 gtatttttt   ttagagatgg  ggtctcagta  tgttgaccag  gcttgtctta  aactcccggc   42973
ctcaagtgat  cctcccactt  cagtctccca  aagtgctggg  attacaggca  tgagccactg   43033
cggccggttt  gttttctttt  tttttcgtt   ttttggagac  ggaatttcac  ctttgttgcc   43093
caggatggag  tgcaatggca  cgatatcgcc  tcaccacaac  ctctgcctcc  tgggttcaaa   43153 ccatttcct   gcctcagcct  tcttagtagc  tgggattaca  agcatgtgcc  accacgcccg   43213
gctgattttg  tattttagt   agagatgggg  tttctccatg  ttggccaggc  tggtctcgaa   43273
ctcctgacct  caggtcattc  gcccacctct  gcctcccaaa  gtgctgggat  acaggcgtg    43333 agccaccgtg  cccggtggtt  tgtattcttt  ttactgagag  tcgtgaaagg  cagtgatcct   43393
ctgtcacatg  tgatcttggc  tctcagggga  catttggcaa  tttctagaga  ttttttggtt   43453
gtcacaagtc  aatggggaag  actgttggca  tttagtgggt  agaggctggt  gacgctgctg   43513
aacacccaga  acagggaagt  agcaggccct  agatagagcc  atcgtgggga  accctgctc    43573 taaggaaatg  gcgctatttt  ataaccccac  gttcctggca  tgattaccaa  cagccaaaag   43633
tggagtcccc  ccaagtgtgt  tcgtccattt  gcattgcagt  aaaggaatag  ctgaggccgg   43693
gtaatttata  aagaaagag   atttaaactg  ggtatggcag  tttatgccta  taatcccaga   43753
actttgggag  gctgaggcag  gaggatcgct  tgagtccagg  agtgtgagac  cgagaccagc   43813
ctggccaaca  tgacgaaact  ctgtctctac  aaaaaataca  aaaagtaggc  caggcacggt   43873
ggttcacgcc  tgtaatccca  gcactttggg  aggccgaggc  gggcggatca  cgaggtcagg   43933
agatcgagac  catcctggct  aacacggtga  aaccccgtct  ctactaaaaa  tacaaaaaca   43993
aaattagccg  ggtgtggtgg  caggcgcctg  tagtcccagc  tactcgggag  gctgaggcgg   44053
gagaatggcg  tgaacccggg  aggcggagct  tgcagtgagc  caagatcgcg  ccactgcact   44113
ccagcctggg  tgaccgagtt  gagactccgt  ctcaaaaaaa  aaaaaaaaa   aaaaaataca   44173 aaaagtagcc  aggtgtggtg  gcaggcacct  gtaatcctgg  gttctcgaga  ccgaggcatg   44233
agaattgcct  gaccccagga  ggtggaggct  gcagtgagcc  aagatcatgc  cactgcactc   44293
cagcctgggc  gacagagtgg  gactctgtct  caaaaacaa   caaaaaaaa   gttctggaaa   44353 tggatggtgg  tgatggtgat  acttccacaa  cagcgtgaat  ctgcttaagg  ccaccgaact   44413
gtgcactcac  aaatagtcga  gatggtacat  tttatgttat  gtgtatttca  ccacaattaa   44473
aaactagttg  tgggccaggt  gtggtggttc  atgcctgtaa  tcccagcact  ttgggaggtc   44533
agagggaggt  ggatcatgag  gtcagcagtt  cgagaccagc  caggccaaca  tggtgaaacc   44593
ccatctctac  taaaaataca  aaaattagcc  aggcgtggtg  gcacatgcct  gtagtcccag   44653
ctacttgaga  ggctgaagca  ggagaatcgc  ttgaacctgg  gaggctaaga  ttgcagtgag   44713
ccgagatcgt  gccactgcac  tccagcctgg  acgacagagt  gagacttcgt  ctcaaaaaaa   44773
aaaccaaaaa  aaaaattagc  tgtgggtcag  gcactgtggc  tcacgcctgt  aatcccagca   44833
ctttgggaga  ccgaggtagg  tggatggcct  gaggtcagga  gttcgaatcc  agcctggcca   44893
acatggtgaa  agcccgtctc  tactaaaaat  acaaaaaatt  agtcaggtat  gttggcacac   44953
ctgtaatccc  agctactcgg  gaggctgaag  caagagaatc  gtttgaaccc  aggaggtgga   45013
cgttgcagtg  agccgagatt  gggccactgt  actccagcct  gggcaacaaa  agtgaaactc   45073
tgtctgaaac  aaacaaacaa  acaaacaaac  agacaaacaa  aaaaactagt  tgtggagaga   45133
```

```
gggtggcctg tgtctcatcc cagtgtttaa cgggatttgt catcttcctt gctgcctgtt   45193 tag gac aaa gta ttt tgg aca gat atc atc aac gaa gcc att ttc agt    45241
    Asp Lys Val Phe Trp Thr Asp Ile Ile Asn Glu Ala Ile Phe Ser
    595                 600                 605 gcc aac cgc ctc aca ggt tcc gat gtc aac ttg ttg gct gaa aac cta    45289
Ala Asn Arg Leu Thr Gly Ser Asp Val Asn Leu Leu Ala Glu Asn Leu
610                 615                 620                 625 ctg tcc cca gag gat atg gtt ctc ttc cac aac ctc acc cag cca aga g  45338
Leu Ser Pro Glu Asp Met Val Leu Phe His Asn Leu Thr Gln Pro Arg
                630                 635                 640 gtaagggtgg gtcagcccca cccccccaac cttgaaacct ccttgtggaa actctggaat  45398
gttctggaaa tttctggaat cttctggtat agctgatgat ctcgttcctg ccctgactcc  45458
gcttcttctg ccccag ga  gtg aac tgg tgt gag agg acc acc ctg agc aat  45509
                     Gly Val Asn Trp Cys Glu Arg Thr Thr Leu Ser Asn
                                 645                 650 ggc ggc tgc cag tat ctg tgc ctc cct gcc ccg cag atc aac ccc cac    45557
Gly Gly Cys Gln Tyr Leu Cys Leu Pro Ala Pro Gln Ile Asn Pro His
655                 660                 665 tcg ccc aag ttt acc tgc gcc tgc ccg gac ggc atg ctg ctg gcc agg    45605
Ser Pro Lys Phe Thr Cys Ala Cys Pro Asp Gly Met Leu Leu Ala Arg
670                 675                 680                 685 gac atg agg agc tgc ctc aca ggtgtggcac acgccttgtt tctgcgtcct       45656
Asp Met Arg Ser Cys Leu Thr
                690 gtgtcctcca actgcccct  cctgagcctc tctctgctca tctgtcaaat gggtacctca  45716 aggtcgttgt aaggactcat gagtcgggat aaccatactt ttcttggatg acacatcag   45776 caccgggctt gacatttacc cagttcccct ttgatgcctg gtttcctctt tcccggcccc  45836 ctgaagaggt gatctgattt ctgacaggag ccctgaggga ggaaatggtc cctttgttg   45896 acttttcttt ttcttttattt ttttcttttg agatttgctg tcacccagcc tggaatgcag 45956 tggtgccatc ttggctcact gctacctctc ccactgggtt caagcaattc tcctgcctca  46016 gcctcccaag tagctgggat tacaagcatg cgccaccatg cctggctaag ttttgtattt  46076 ttagtacaga cagggtttct ccatggtggc caggctggtc ttgaactcct gacctcaggt  46136 gatcctccca cctctgcctc ccgaagtgct acgattacag gcatgagcca ccgcgcccat  46196 cccccttttgt tgactttct catcctctga gaaagtctca gttgaggcca gcacctccct  46256 caagtgaatt gaatctccct tttgaacaac aacaaataac aatatgaccc agacgtggtg  46316 gctcacacct gtggtcccag ctactcggga ggctgaggtg tgaggattgc ttgagcccag  46376 gaggtcaagg ctacagagag ctataatcac accacttcac tccagcctgg gggacaaagt  46436 gaaaccctgt ctgaaaaaaa caaaaaaaga aaaggaaaa agaaacaata cgatcacaaa   46496 gtagatattc atagtgttta ttttcagtac tcttttttttt ttttttttttt ttttttgaga 46556 cggagtcttg ctctgttgcc caggctggag tgcagtggca cgatcttggc tcactgcagc  46616 ctctgcctcc caggttcaag cgcttggctc actgcaacct ccgcctcctg ggttcaagcg  46676 cttcttctgc ctcagcctcc ccagtagctg ggactatagg cacgtccac  tacgcccagc  46736 taattttttg tattttttag tagagatggg gtttcactat gttagccagg atggtctcga  46796 tctcctgacc tcgtgatctg cctgccttgg ctcccaaag  tgttgggatt atgggcatga  46856 gccactgcac ctggccttttt tttttttttt tttgagatg  gagtttcgct cttgttgccc  46916 aggctggagt gcaatggtgt gatctcggct cactgcaacc tctgcctcct gggttcaagc  46976 aattctcctg cctcagcctc ccgagtagct gggattacag gcacctgcca ccacgcctgg  47036
```

```
ctaattttg  tacttttagt  agagacgggg  tttctccatg  ttggtcaggc  tggtctcaaa   47096
ctcctgacct  caggtgatcc  acccacctcg  gcctcccaaa  gttctgggat  tacagacatg   47156
agccaccgcg  cctggccgtg  tctgccttt   tttagttatt  tcttttttt   tttttttttt   47216
ttttgagaca  gagtcttact  ccgtcgccca  ggctggagtg  cagcggtgcg  atgtctgcgc   47276
actgcaagct  ccgcccctg   ggttcatgcc  attctcctgc  ctcagccttc  tgagtagctg   47336
ggactgcagg  cgcctgccac  tacgcccggc  tactttttg   tatatttagt  agagatggag   47396
tttcactgtg  ttagccagga  tggtctcgat  ctcctgactt  tgtgatccgc  cgcctcggc    47456
ctcccaaagt  gctgggatta  caggcgtgag  ccaccatgcc  aggcttttt   tttttttttt   47516
tttttgaga   cggagtcttg  ctctgtcgcc  caggctggag  tgcagtgcca  tgatctcagc   47576
tcactgcaag  ctccacttcc  caggctcacg  ccattctcca  gcctcagcct  cccaagtagc   47636
tgagactaca  ggggcccgcc  accacactcg  gctaatttt   ttgtattttt  agtagagacg   47696
gggtttcacc  atgttagcca  ggctggtctt  gaactcctaa  cctcaggcga  ttcacctgcc   47756
tcggcctccc  aaagtgctgg  gattaaaggt  atgagccacc  tcgcctggtg  tgagccacct   47816
cgcccagcct  gagccacctc  acccagccta  agccactgtg  cctggcctga  ttttggactt   47876
tttaaaaatt  ttattaataa  ttattttgg   gtttctttt   tttgagacag  gtcttactc    47936
tgtcatccag  gccatcctgt  ctgtctgtca  tcccagtgat  gggatcatac  cttgctgcag   47996
cctctacctc  ctgggctcaa  gcgatcctcc  ccctcagcc   tcctgagtag  ctgggagtac   48056
aggtgtgcac  caccacacct  ggctaatttt  ttttttttt   tttgtatata  gagatggtat   48116
tttgccatgt  tgaccaggct  agtcttaaac  tcctggactc  actcaagaga  tcctcctgcc   48176
ttggcctccc  aagtcatttt  gagactttcg  tcattaggcg  cacacctatg  agaagggcct   48236
gcaggcacgt  ggcactcaga  agacgtttat  ttattctttc  a gag gct gag gct gca   48292
                                                  Glu Ala Glu Ala Ala
                                                              695
gtg gcc acc cag gag aca tcc acc gtc agg cta aag gtc agc tcc aca         48340
Val Ala Thr Gln Glu Thr Ser Thr Val Arg Leu Lys Val Ser Ser Thr
        700                 705                 710
gcc gta agg aca cag cac aca acc acc cga cct gtt ccc gac acc tcc         48388
Ala Val Arg Thr Gln His Thr Thr Thr Arg Pro Val Pro Asp Thr Ser
    715                 720                 725
cgg ctg cct ggg gcc acc cct ggg ctc acc acg gtg gag ata gtg aca         48436
Arg Leu Pro Gly Ala Thr Pro Gly Leu Thr Thr Val Glu Ile Val Thr
730                 735                 740                 745
atg tct cac caa g gtaaagactg gccctccct aggccctct tcacccagag             48489
Met Ser His Gln
acgggtccct  tcagtggcca  cgaacatttt  ggtcacgaga  tggagtccag  gtgtcgtcct   48549
cactcccttg  ctgaccttct  ctcacttggg  ccgtgtgtct  ctgggccctc  agtttccct    48609
tctgtaaagt  gggtctaata  acagttcttg  ccctctttgc  aaggattaaa  tgggccaaat   48669
catatgaggg  gccaggtcct  tcaggctcct  ggttcccaaa  gtcagccacg  caccgtgtgg   48729
gtcccaaaat  tttatcaagg  cacattcgtt  gcctcagctt  caggcatctg  cccaaaaagg   48789
ccaggactaa  ggcaaggaga  gggagggatt  cctcagtact  cagcttttca  cagaggctcc   48849
aaaaggctaa  ggaatccagt  aacgttttaa  cacaattta   caattttttt  ttttgagacg   48909
gagttttgct  cttgttgccc  aggctggagt  gcagtggcac  gatctcggct  cactgcaacc   48969
tctggctccc  gggttcaagc  gattctcctg  cctcagtctc  ccgagtagct  gggattacag   49029
gcatgcgcca  ccacgctcgg  ctaatttgt   attttagta   cagaagggc   ttctctgttg   49089
```

```
gtcaggctgg tcgtgaactc tcaacctcag gtgagccacc cgcctgagcc tcccaaagtg   49149
ctgggattac aggtgtgagc caccacgcct ggccttttt ttgagacaga gtctcgctct   49209
cgcccatgct gtactgcagt gacgcagtct gggctcactg taacctccgc ttcccaggtt   49269
caagtgattc ttctgccgca gcctcccatg tagagtagct gggattacag gcacccgcca   49329
ccatgcctgg ctaattcttg cattttagt agagatgggg tttcacagtg ttggccaggc   49389
tggtctcaaa cttctgacct caagtcatct gcctgccttg gccctgccaa agtgctggga   49449
ttatagatgt gagccaccgc gcctggccta cagtttattc tttggtggct cacacctgta   49509
atctcagcac tttgggaggc caaggtggga aatggcttg agcccaggag ttcaagtcca   49569
gcctgggcaa catagcaaga ccctatctct actacaaaat aaataataaa taaactaatt   49629
ttttttcttt taaacccaa ctattcaaca tggcaatgca atatattaaa aaatttttt   49689 ttttctttga aacggagtct ctcactgtca cccgggctgg agtgcagtgt cgccatcttg   49749
gctcactgca acctccgcct cccaggtcca agtgattctc ctgcttcagc ctcccgagta   49809
gctgggatta caggcaccca ccaccatacc cagctaatat ttttgtattt ttagtagaga   49869
tggggtttca ctatgttggg caggctggtc tggaactcct gacctcgtga tctgcccgag   49929
gatcggcggc ctcccaaagt gctggggatt gcaggcatga gccaccgtgc ccagccaaaa   49989 ctttttatt tttatttttt tgggacacgg tctcactgtg tacccagac tggagtgata   50049 gagtgctgtc atggctcact gcagcctcaa cctccctggg ctcaggtgat cttcctgctt   50109
cagtctccca ggtagctggg actacaggca tgagccacca cacccagcta atttttgaat   50169 tttttttgtag agacagggtt tcaccttgtg gcccagactt gtctctaact ccagggctca   50229
agcgatctgc ccaccttggc ctcccaaagt gctgagatta atgcaattta aaaaatttt   50289 tggccaggcc tggtggctca tgcctgtatt cacaacacct gggaggcaa aggtgggcag   50349 atcacttgag gtcaggagtt cgagactagc ctggccaaca tggtgaaacc ccctgtctac   50409 taaaaaata caaaaattac ctgggcacag tggtgggtgc ctgtaatccc agctacttgg   50469
gatgctgagg gtggagaatt gcttgaacct gggaggcaga agttgcagta agccaagatc   50529
atgccactgg actccagcct cagtgacaga gcaaaactct gtctccaaaa aaattgtttt   50589
tttttttttt ttttcaaatc atcacactac agccaaggcc tggccactta cttttgtaaa   50649 taaagttta ttggagccag tggaccagtg aggccgaatc ttgcaggtgt aagatcacag   50709
tctatccttg aaaattttga tattttgttc attgggtggt ttttcattaa tttaaatttt   50769
aaaaaataac atattaaagg ctggtgtgga ggtgcacgcc tgcagtccta gctactccca   50829
gaggctgagg cgggagactt gcttgagccc aagagttgaa gtccagcctg gcaacatag   50889 cgagacccc atctctaaaa ataaaaataa tgcattagaa tattattgga ttcctgggca   50949
gggcacagtg gctcacacct gtaatcccag cactttggga ggctgaggtg ggtggatcac   51009
ctgaggtcag gagtttgaga ccagcctggc caacatggtg aaaccccgtc tctactaaaa   51069
atacaaaaat tagccaggcg tggtggcagg tgcctgtaat cccagctact cgggaggctg   51129
aagcacgaga atcgcttgaa tccaggaggc ggaggttgca gtgagctgag attgcgccat   51189
tgcactccag cctggaggac aagagtgaaa ctccattccc ctctgcaaag aaaaggaata   51249
ttatcagatt cctaagcttt ttggctcccc ctttagtttg ggggctgggg tggtgagtgt   51309
ctgacctggc ctcactgtcc tccctggatg tgatgagacc caggtgtggg tcaggatgtc   51369
attcgtttgt ccaccagagg gcgcccaaac tgctttgagc tgctgggaaa tggtgctcct   51429
agacttttag caaacaaaca aaaaaaaatg gcacatcggc aaatttcaga ccattctttt   51489
```

```
tttttttttt tttggttcca gagtagctga aatctttgtt cagttacaag caggataaaa    51549
tggaaactgc ctgggagagg ctgagaaacc ttccttgcttg ggggaggtgg ggcactgcta   51609
gaattaatcg cttcacagac cagcccatcc aggactcctc aaatttggca aaaaagccat    51669
tcattcattc attcatttat gtagagacga ggggatctg gctatattgc ctagattggt    51729
ctcaaattcc tggcctcaag tgatcctcct gccttggtct actaatgtgc tgcgattaca    51789
ggcatgagcc accgtgccta gctctagtgg acttgaaatg ttgccttgcc cagggccctt    51849
atgttgaatg gcccaggtcc acttgtatgg ttctgtacca aggttaaccc catcccataa    51909
tgcctgggac agttgatgca ggacaatcag cttctgtgcc attcaacctc aggactgagc    51969
atgctgggca ttgtggggtc cgaaggtggc tcccctgtcc ccttcaaaat accctctttt    52029
tcttttcttc tttttttttt tttttttttt ttgagacgaa gtcttgctct gttgccccag    52089
ctagagtgca gtggtgcgat ctcagctccc cgcaacctct gcttcccggg ttcaggcgat    52149
tctcctgcct cagcctcctg agtagctggg attacaggtg cccaccgcca cagctggcta    52209 attttttgtat ttttagtaga cagggtttt caccgtgttg gccaggctgg tcttgaactc    52269
ctgacctcag gcaacctgcc cacctcagcc tcccaaagtg ctgggattac aggtttgagc    52329
cactgggcct ggcctttttt tttttttttt gagagggagt ctcactctgt tgcccaggct    52389
ggagtgcaat ggcgcgatct tgactcactg caactccatt tcccgggttc aagtgattct    52449
cctccctcag cctcccaagt agctgggatt acaggtgcat gccaccacgg ccagctaatt    52509
ttgtattttt agtagagaca gggtttcact atgttgatca tgctggtctc aaactcctga    52569
ccttaggtga tctgcccgcc ttagcctccc aaagtgttgg gattacaggt gtgagccacc    52629
gcgcccagac caaaatatgc tcattttaat aaaatgcaca agtaggttga caagaatttc    52689
acctgcaacc ttgtcaacca cctagaataa agcctctgc agccctcccc taaagactca    52749
tcaatgtgag gctcaagaac cttcttaggc tgggctcggt ggctcatttc tgtaatccct    52809
gcactttgga aggctgaggc aggaggatct cttgaggcca ggagttcaag acaagcctgg    52869
gcaacatagc cagacctctg tttctatccc ccacaaaaag aaccttctta aaccggaatt    52929
gagtcctaca acctcgataa ctcacaaata agcccgtgtg gcctctcaca gacttgggaa    52989
gttctccaag tgtccaggga gatgtgccag gcgctttcct gccgtgacca ccgtcctctg    53049
cctgctccat tccttggtgg ccttcccttta gacctgggcc tcactcttgc ttctctcctg    53109 cag ct  ctg ggc gac gtt gct ggc aga gga aat gag aag aag ccc agt      53156
    Ala Leu Gly Asp Val Ala Gly Arg Gly Asn Glu Lys Lys Pro Ser
        750             755                 760 agc gtg agg gct ctg tcc att gtc ctc ccc atc g gtaagcgcgg              53200
Ser Val Arg Ala Leu Ser Ile Val Leu Pro Ile
765             770             775 gccggtcccc cagcgtcccc caggtcacag cctcccgcta tgtgacctcg tgcctggctg    53260
gttgggcctg ttcactttt ctcctggaca gggaacagcc ccactggtgt cctttatcac     53320
ccccacggcc tctcctggct tggggctgac agtgacaaga tcagacagct aagggtcag    53380 atggaggatg tggagctggg tcccgtgctg tggaatagcc tcaccgagat ttgagtgcct    53440
tctggggaac tggttcccctt gcaggggct gtgtggagag gcgcgctctc cctgcctcac    53500
ccatgctcat cctaactcgg ttaccatcac atctcttttt tcttttttc ttaaattta      53560 agaaaaaaga aatttaattt ttttgagaga cagagtcttg ctctgtcacc caggctggag    53620
tgcagtggca ccatcatgcc tcgctgcagc ctcaatgtct gggctcaagc gatcctccca    53680
cctcagcctc ctgagtagct ggtgcaagcc actatacccc acttcctatt tcttaaaaag    53740
```

```
tcacagccct gtgtgtggct aatcctggac agaaatctag aagaagtcag ctacttctgg    53800
ggcgtggctc acccagtggg cttcaggtta gatatttctt atacttatga ggctgggtgt    53860
ggtggcttat gcctgtaatc ccagcacttt gggaggctga agtgggtgga ttgcttgggc    53920
tcaggagttc gagaccaacc tgggcaacat ggcgaaaccc tgtttctaga aaaggtacaa    53980
aaattagctg ggcaggtggc acgtgcctgt ggtaccagct acttgagggc ctgaggcagg    54040
aggatcgctt gaacctggga ggtcgaggtt gcagtgaact gagatcatgt cactgcactc    54100
cagcctggtg acagagcaag accccgtctc aaaaaaaaaa aagaaagaa aaaattctt     54160 atgcatagat ttgcctcttt tctgtttgtt tgttttgaga tggagtctcg ctctgtcgcc    54220
caggctggag tacagtggct caacctcggc tcactgcaac ctctgcctcc cgggttcaag    54280
caattctcct gcctcagcct cctgagtagc tgggactaca cgcccgcca ccatgcccag    54340 ctaattttg tatttttagt agagactgac tgggtttcat catgttggcc aggctggtct    54400
cgaactcttg acctcatgat ccgcccgcct cagcctccca aaatgctggg attacaggcg    54460
tgagccacca ggcccaggcc gcaaggcgat ctctaaacaa acataaaga ccaggagtca     54520 aggttatggt acgatgcccg tgttttcact ccagccacgg agctgggtct ctggtctcgg    54580
gggcagctgt gtgacagagc gtgcctctcc ctacag tg ctc ctc gtc ttc ctt      54633
                                        Val Leu Leu Val Phe Leu
                                                              780 tgc ctg ggg gtc ttc ctt cta tgg aag aac tgg cgg ctt aag aac atc      54681
Cys Leu Gly Val Phe Leu Leu Trp Lys Asn Trp Arg Leu Lys Asn Ile
            785                 790                 795 aac agc atc aac ttt gac aac ccc gtc tat cag aag acc aca gag gat      54729
Asn Ser Ile Asn Phe Asp Asn Pro Val Tyr Gln Lys Thr Thr Glu Asp
        800                 805                 810 gag gtc cac att tgc cac aac cag gac ggc tac agc tac ccc tcg          54774
Glu Val His Ile Cys His Asn Gln Asp Gly Tyr Ser Tyr Pro Ser
    815                 820                 825 gtgagtgacc ctctctagaa agccagagcc catggcggcc ccctcccagc tggaggcata    54834
tgatcctcaa gggaccaggc cgaggcttcc ccagccctcc agatcgagga cagcattagg    54894
tgaatgcttc tgtgcgctca ttcagaatgt cagcggacaa tggccttggt ggtgtagagg    54954
aatgttggat aagcaaatag agagctccat cagatggtga cagggcaaag aaagtcaaaa    55014
ggagttcaga ggccgggcgc ggtggctcat gcctgtaatc ccaggacttt gggaggccga    55074
ggctggcgga tcacctgaag tcaggagttt gagaccagct tggccatcat gacaaaaccc    55134
cgtctctatt aaaaatacaa aaaattagcc aggcgtggga gtgggcgcct gtaatcccag    55194
ctactcggga ggccgaggta gaaaaatcgc ttgaacctag gaggcagagg ttgcagtgag    55254
ccgagatcgc gccactgcat tccagcccgg gaggcaagag caaaactcca tctcaaaaaa    55314 aaaaaaaaa ggagttcaga ggcccggcat ggtggttcac acatgtgatc ccagaacttg     55374
gggaggttga ggcaggagaa tcacctgagc tcagagttca agaccagcct gggcagcaca    55434
gcaagacccc atctctgcaa aaaataaaaa tttagcccag tgtggtgatg agcgcctagt    55494
tccagctact agggaggcta aggcaggagg attgcttgag gctaaggtag gagattgaga    55554
ctgcagtgac ttgtgattgc gtcactgcgc tccagcctgg gtgacagagc aagcccttgt    55614
ctcttaaaaa aaaaaaaaa ttcaaagaag ggtttccaga gggccaggag ggaggaaggg     55674
agaggaggtg ttttatttt ttgctttat ttttatttt gagacagagt ctctctctgt      55734
cacccaggtt ggagtgcagt gctgtgatct tggctcactg caacttctgc ctcctgggtt    55794
caagcaattc ttatgcctca gcctcagcct cctgagtagc tgggattaca acactatgcc    55854
```

```
cgggtaattt ttgtattttt agtagagacg aggtttcgcc atgttgccca gactggtctc    55914
gaactcctga cctcaagtga tccacccgcc ttggcctccc cacgtgctgg gattgcaggc    55974
gtgagccact gcgcccgcct tgatctttac acaaggggtt tagggtaggt agccttctct    56034
gaaccaggag aacagcctgt gcgaaggccc tgaggctgga ccgtgcctgt tgggtttgag    56094
gccgttgtag ctggagcaaa cagagagagg ggtaaaaagg caggaggcta ccaggcaggt    56154
tgtgcagagc cttgtgggcc actggggagg actttggctt ttgccctgag agcggtggga    56214
agtgactgaa tccggtactc accgtctccc tctggcggct cctggggaa  catgcttggg    56274 gatcaggctg ggggaggctg ccaggcccag gaggtgagaa gtaggtggcc tccagccgtg    56334
tttcctgaat gctggactga tagtttccgc tgtttaccat ttgttggcag aga cag       56390
                                                        Arg Gln
                                                            830 atg gtc agt ctg gag gat gac gtg gcg tgaacatctg cctggagtcc            56437
Met Val Ser Leu Glu Asp Asp Val Ala
              835 cgtccctgcc cagaacccct cctgagacct cgccggcctt gttttattca aagacagaga    56497 agaccaaagc attgcctgcc agagctttgt tttatatatt tattcatctg ggaggcagaa    56557 caggcttcgg acagtgccca tgcaatggct tgggttggga ttttggtttc ttcctttcct    56617 cgtgaaggat aagagaaaca ggcccggggg gaccaggatg acacctccat ttctctccag    56677 gaagttttga gtttctctcc accgtgacac aatcctcaaa catggaagat gaaaggggag    56737 gggatgtcag gcccagagaa gcaagtggct ttcaacacac aacagcagat ggcaccaacg    56797 ggacccccctg gccctgcctc atccaccaat ctctaagcca aacccctaaa ctcaggagtc    56857 aacgtgttta cctcttctat gcaagccttg ctagacagcc aggttagcct ttgccctgtc    56917 acccccgaat catgacccac ccagtgtctt tcgaggtggg tttgtacctt ccttaagcca    56977 ggaaagggat tcatggcgtc ggaaatgatc tggctgaatc cgtggtggca ccagaccaa    57037 actcattcac caaatgatgc cacttcccag aggcagagcc tgagtcactg gtcacccttα    57097 atatttatta agtgcctgag acacccggtt accttggccg tgaggacacg tggcctgcac    57157 ccaggtgtgg ctgtcaggac accagcctgg tgcccatcct cccgacccct acccacttcc    57217 attcccgtgg tctccttgca cttttctcagt tcagagttgt acactgtgta catttggcat    57277 ttgtgttatt attttgcact gttttctgtc gtgtgtgttg ggatgggatc ccaggccagg    57337 gaaagcccgt gtcaatgaat gccggggaca gagaggggca ggttgaccgg gacttcaaag    57397 ccgtgatcgt gaatatcgag aactgccatt gtcgtcttta tgtccgccca cctagtgctt    57457 ccacttctat gcaaatgcct ccaagccatt cacttcccca atcttgtcgt tgatgggtat    57517 gtgtttaaaa catgcacggt gaggccgggc gcagtggctc acgcctgtaa tcccagcact    57577 ttgggaggcc gaggcgggtg gatcatgagg tcaggagatc gagaccatcc tggctaacac    57637 gtgaaacccc gtctctacta aaaatacaaa aaattagccg ggcgtggtgg cgggcacctg    57697 tagtcccagc tactcgggag gctgaggcag gagaatggtg tgaacccggg aagcggagct    57757 tgcagtgagc cgagattgcg ccactgcagt ccgcagtctg gcctgggcga cagagcgaga    57817 ctccgtctca aaaaaaaaa acaaaaaaaa accatgcatg gtgcatcagc agcccatggc    57877 ctctggccag gcatggcgag gctgaggtgg gaggatggtt tgagctcagg catttgaggc    57937 tgtcgtgagc tatgattatg ccactgcttt ccagcctggg caacatagta agaccccatc    57997 tcttaaaaaa tgaatttggc cagacacagg tgcctcacgc ctgtaatccc agcactttgg    58057 gaggctgagc tggatcactt gagttcagga gttggagacc aggcctgagc aacaaagcga    58117
```

```
gatcccatct ctacaaaaac caaaaagtta aaatcagct gggtacggtg cacgtgcct      58177
gtgatcccag ctactggga ggctgaggca ggaggatcgc ctgagcccag gaggtggagg    58237
ttgcagtgag ccatgatcga gccactgcac tccagcctgg caacagatg aagaccctat   58297
ttcagaaata caactataaa aaaataaata atcctccag tctggatcgt ttgacgggac   58357
ttcaggttct ttctgaaatc gccgtgttac tgttgcactg atgtccggag agacagtgac  58417
agcctccgtc agactcccgc gtgaagatgt cacaagggat tggcaattgt ccccaggac   58477
aaaacactgt gtccccccca gtgcagggaa ccgtgataag cctttctggt tcggagcac   58537
gtaaatgcgt ccctgtacag atagtgggga ttttttgtta tgtttgcact ttgtatattg   58597
gttgaaactg ttatcactta tatatatata tatacacaca tatatataaa atctatttat   58657
ttttgcaaac cctggttgct gtatttgttc agtgactatt ctcggggccc tgtgtagggg   58717
gttattgcct ctgaaatgcc tcttctttat gtacaaagat tatttgcacg aactggactg   58777
tgtgcaacgc ttttttggag aatgatgtcc ccgttgtatg tatgagtggc ttctgggaga   58837
tgggtgtcac ttttaaacc actgtataga aggttttgt agcctgaatg tcttactgtg     58897
atcaattaaa tttcttaaat gaaccaattt gtctaaactc gatgcacgtt cttctgttcg   58957
cgcgcttctt tttgtttttt ttttttttcct gagatggagc ctggctctgt caccccctggc 59017
tggagtgcag tggcatgatc tcggcttact gcaagctccg cctcccaggt tcaagcaatt    59077
ctcctgcctc agcctcccta gtagctagga ttacaggtga gtgccaccac gcctggccaa   59137
tttttttttt tttttttttt ttgagacaga gtctcgctct gtcacccagg ctggagtgca   59197
gtggtgtgat ctcggctcac tgcaagctct gcctcccagg ttaatgccat tctcctgtct   59257
cagcctcctg agtagctggg gccacaggcg cctgccacca cgcccggcta attttttttt   59317
gtacttcttt tagtacagac gggtttcac catgttagcc aggatggtct cgatctcctg   59377
accttgtgat ccacctgctt cggcctccca aagtgctgag attacaggcg tgagccaccg   59437
cgggtggcca acgctaattt ttttgttttt ttagatggag tcttgctctg tcgcccaggc   59497
tggagtgcag tggcgtgatc tctgcctact gcaagctccg cctcccgggt tcatgccatt   59557
ctcctgcctc agcctcctga gtaactggga ctacaggcac ccgccaccac gcccggctaa   59617
tttttgtat tttagtaga cagggttt caccgtgtta gccaggatgg tcttgatctc      59677
ctgaccttgt gatccacccg tctcggcctc ccaaagtgct gggattagag gtgtgagcca   59737
ccacacctgg cctagcctgg ctaatttttg tattttttggt agagacgggg tttcaccatg   59797
ttggtcaggc tggtcttgaa cttctgacct caggtaatct gcctgcctca gtctcccaaa   59857
gtgctgggat tacaggtgtg agccaccgcg cctggcctca cttccttctg tcatctgttt   59917
gtggattgga ctccccagga gaaggaccca gaagggaag actcccagaa ctccgggcaa   59977
gatgcaatct ccgtgggctg cca                                          60000
```

```
<210> SEQ ID NO 2
<211> LENGTH: 860
<212> TYPE: PRT
<213> ORGANISM: Homo sapiens

<400> SEQUENCE: 2

Met Gly Pro Trp Gly Trp Lys Leu Arg Trp Thr Val Ala Leu Leu Leu
    -20                 -15                 -10

Ala Ala Ala Gly Thr Ala Val Gly Asp Arg Cys Glu Arg Asn Glu Phe
 -5              -1  1               5                   10

Gln Cys Gln Asp Gly Lys Cys Ile Ser Tyr Lys Trp Val Cys Asp Gly
             15                  20                  25
```

```
Ser Ala Glu Cys Gln Asp Gly Ser Asp Glu Ser Gln Glu Thr Cys Leu
         30                  35                  40
Ser Val Thr Cys Lys Ser Gly Asp Phe Ser Cys Gly Gly Arg Val Asn
         45                  50                  55
Arg Cys Ile Pro Gln Phe Trp Arg Cys Asp Gly Gln Val Asp Cys Asp
 60                  65                  70                  75
Asn Gly Ser Asp Glu Gln Gly Cys Pro Pro Lys Thr Cys Ser Gln Asp
                 80                  85                  90
Glu Phe Arg Cys His Asp Gly Lys Cys Ile Ser Arg Gln Phe Val Cys
             95                 100                 105
Asp Ser Asp Arg Asp Cys Leu Asp Gly Ser Asp Glu Ala Ser Cys Pro
         110                 115                 120
Val Leu Thr Cys Gly Pro Ala Ser Phe Gln Cys Asn Ser Ser Thr Cys
         125                 130                 135
Ile Pro Gln Leu Trp Ala Cys Asp Asn Asp Pro Asp Cys Glu Asp Gly
140                 145                 150                 155
Ser Asp Glu Trp Pro Gln Arg Cys Arg Gly Leu Tyr Val Phe Gln Gly
                 160                 165                 170
Asp Ser Ser Pro Cys Ser Ala Phe Glu Phe His Cys Leu Ser Gly Glu
             175                 180                 185
Cys Ile His Ser Ser Trp Arg Cys Asp Gly Gly Pro Asp Cys Lys Asp
         190                 195                 200
Lys Ser Asp Glu Glu Asn Cys Ala Val Ala Thr Cys Arg Pro Asp Glu
         205                 210                 215
Phe Gln Cys Ser Asp Gly Asn Cys Ile His Gly Ser Arg Gln Cys Asp
220                 225                 230                 235
Arg Glu Tyr Asp Cys Lys Asp Met Ser Asp Glu Val Gly Cys Val Asn
                 240                 245                 250
Val Thr Leu Cys Glu Gly Pro Asn Lys Phe Lys Cys His Ser Gly Glu
             255                 260                 265
Cys Ile Thr Leu Asp Lys Val Cys Asn Met Ala Arg Asp Cys Arg Asp
         270                 275                 280
Trp Ser Asp Glu Pro Ile Lys Glu Cys Gly Thr Asn Glu Cys Leu Asp
         285                 290                 295
Asn Asn Gly Gly Cys Ser His Val Cys Asn Asp Leu Lys Ile Gly Tyr
300                 305                 310                 315
Glu Cys Leu Cys Pro Asp Gly Phe Gln Leu Val Ala Gln Arg Arg Cys
             320                 325                 330
Glu Asp Ile Asp Glu Cys Gln Asp Pro Asp Thr Cys Ser Gln Leu Cys
         335                 340                 345
Val Asn Leu Glu Gly Gly Tyr Lys Cys Gln Cys Glu Glu Gly Phe Gln
         350                 355                 360
Leu Asp Pro His Thr Lys Ala Cys Lys Ala Val Gly Ser Ile Ala Tyr
         365                 370                 375
Leu Phe Phe Thr Asn Arg His Glu Val Arg Lys Met Thr Leu Asp Arg
380                 385                 390                 395
Ser Glu Tyr Thr Ser Leu Ile Pro Asn Leu Arg Asn Val Val Ala Leu
                 400                 405                 410
Asp Thr Glu Val Ala Ser Asn Arg Ile Tyr Trp Ser Asp Leu Ser Gln
             415                 420                 425
Arg Met Ile Cys Ser Thr Gln Leu Asp Arg Ala His Gly Val Ser Ser
         430                 435                 440
Tyr Asp Thr Val Ile Ser Arg Asp Ile Gln Ala Pro Asp Gly Leu Ala
```

```
                445             450             455
Val Asp Trp Ile His Ser Asn Ile Tyr Trp Thr Asp Ser Val Leu Gly
460                 465                 470                 475

Thr Val Ser Val Ala Asp Thr Lys Gly Val Lys Arg Lys Thr Leu Phe
                480                 485                 490

Arg Glu Asn Gly Ser Lys Pro Arg Ala Ile Val Val Asp Pro Val His
                495                 500                 505

Gly Phe Met Tyr Trp Thr Asp Trp Gly Thr Pro Ala Lys Ile Lys Lys
                510                 515                 520

Gly Gly Leu Asn Gly Val Asp Ile Tyr Ser Leu Val Thr Glu Asn Ile
                525                 530                 535

Gln Trp Pro Asn Gly Ile Thr Leu Asp Leu Leu Ser Gly Arg Leu Tyr
540                 545                 550                 555

Trp Val Asp Ser Lys Leu His Ser Ile Ser Ser Ile Asp Val Asn Gly
                560                 565                 570

Gly Asn Arg Lys Thr Ile Leu Glu Asp Glu Lys Arg Leu Ala His Pro
                575                 580                 585

Phe Ser Leu Ala Val Phe Glu Asp Lys Val Phe Trp Thr Asp Ile Ile
                590                 595                 600

Asn Glu Ala Ile Phe Ser Ala Asn Arg Leu Thr Gly Ser Asp Val Asn
                605                 610                 615

Leu Leu Ala Glu Asn Leu Leu Ser Pro Glu Asp Met Val Leu Phe His
620                 625                 630                 635

Asn Leu Thr Gln Pro Arg Gly Val Asn Trp Cys Glu Arg Thr Thr Leu
                640                 645                 650

Ser Asn Gly Gly Cys Gln Tyr Leu Cys Leu Pro Ala Pro Gln Ile Asn
                655                 660                 665

Pro His Ser Pro Lys Phe Thr Cys Ala Cys Pro Asp Gly Met Leu Leu
                670                 675                 680

Ala Arg Asp Met Arg Ser Cys Leu Thr Glu Ala Glu Ala Ala Val Ala
                685                 690                 695

Thr Gln Glu Thr Ser Thr Val Arg Leu Lys Val Ser Ser Thr Ala Val
700                 705                 710                 715

Arg Thr Gln His Thr Thr Thr Arg Pro Val Pro Asp Thr Ser Arg Leu
                720                 725                 730

Pro Gly Ala Thr Pro Gly Leu Thr Thr Val Glu Ile Val Thr Met Ser
                735                 740                 745

His Gln Ala Leu Gly Asp Val Ala Gly Arg Gly Asn Glu Lys Lys Pro
                750                 755                 760

Ser Ser Val Arg Ala Leu Ser Ile Val Leu Pro Ile Val Leu Leu Val
                765                 770                 775

Phe Leu Cys Leu Gly Val Phe Leu Leu Trp Lys Asn Trp Arg Leu Lys
780                 785                 790                 795

Asn Ile Asn Ser Ile Asn Phe Asp Asn Pro Val Tyr Gln Lys Thr Thr
                800                 805                 810

Glu Asp Glu Val His Ile Cys His Asn Gln Asp Gly Tyr Ser Tyr Pro
                815                 820                 825

Ser Arg Gln Met Val Ser Leu Glu Asp Asp Val Ala
                830                 835

<210> SEQ ID NO 3
<211> LENGTH: 24
<212> TYPE: DNA
<213> ORGANISM: Artificial Sequence
<220> FEATURE:
```

```
<223> OTHER INFORMATION: Ex1F Primer

<400> SEQUENCE: 3
cacattgaaa tgctgtaaat gacg                                          24

<210> SEQ ID NO 4
<211> LENGTH: 24
<212> TYPE: DNA
<213> ORGANISM: Artificial Sequence
<220> FEATURE:
<223> OTHER INFORMATION: Ex1R Primer

<400> SEQUENCE: 4
ctattctggc gcctggagca agcc                                          24

<210> SEQ ID NO 5
<211> LENGTH: 24
<212> TYPE: DNA
<213> ORGANISM: Artificial Sequence
<220> FEATURE:
<223> OTHER INFORMATION: Ex2F Primer

<400> SEQUENCE: 5
ttgagagacc ctttctcctt ttcc                                          24

<210> SEQ ID NO 6
<211> LENGTH: 20
<212> TYPE: DNA
<213> ORGANISM: Artificial Sequence
<220> FEATURE:
<223> OTHER INFORMATION: Ex2R Primer

<400> SEQUENCE: 6
gcatatcatg cccaaagggg                                               20

<210> SEQ ID NO 7
<211> LENGTH: 24
<212> TYPE: DNA
<213> ORGANISM: Artificial Sequence
<220> FEATURE:
<223> OTHER INFORMATION: Ex3F Primer

<400> SEQUENCE: 7
ttcctttgag tgacagttca atcc                                          24

<210> SEQ ID NO 8
<211> LENGTH: 24
<212> TYPE: DNA
<213> ORGANISM: Artificial Sequence
<220> FEATURE:
<223> OTHER INFORMATION: Ex3R Primer

<400> SEQUENCE: 8
gataggctca atagcaaagg cagg                                          24

<210> SEQ ID NO 9
<211> LENGTH: 24
<212> TYPE: DNA
<213> ORGANISM: Artificial Sequence
<220> FEATURE:
<223> OTHER INFORMATION: Mut191-2F Primer

<400> SEQUENCE: 9
acagttcaat cctgtctctt ctct                                          24

<210> SEQ ID NO 10
```

-continued

```
<211> LENGTH: 20
<212> TYPE: DNA
<213> ORGANISM: Artificial Sequence
<220> FEATURE:
<223> OTHER INFORMATION: Ex4AF Primer

<400> SEQUENCE: 10
gtggtctcgg ccatccatcc                                                      20

<210> SEQ ID NO 11
<211> LENGTH: 20
<212> TYPE: DNA
<213> ORGANISM: Artificial Sequence
<220> FEATURE:
<223> OTHER INFORMATION: Ex4ARF Primer

<400> SEQUENCE: 11
agccatcttc gcagtcgggg                                                      20

<210> SEQ ID NO 12
<211> LENGTH: 22
<212> TYPE: DNA
<213> ORGANISM: Artificial Sequence
<220> FEATURE:
<223> OTHER INFORMATION: Mut 509insCR Primer

<400> SEQUENCE: 12
cgagccatct tcgcagtcgg ag                                                   22

<210> SEQ ID NO 13
<211> LENGTH: 20
<212> TYPE: DNA
<213> ORGANISM: Artificial Sequence
<220> FEATURE:
<223> OTHER INFORMATION: Ex4BF Primer

<400> SEQUENCE: 13
cccccagctg tgggcctgcg                                                      20

<210> SEQ ID NO 14
<211> LENGTH: 20
<212> TYPE: DNA
<213> ORGANISM: Artificial Sequence
<220> FEATURE:
<223> OTHER INFORMATION: Ex4BR Primer

<400> SEQUENCE: 14
cgcccccacc ctgccccgcc                                                      20

<210> SEQ ID NO 15
<211> LENGTH: 20
<212> TYPE: DNA
<213> ORGANISM: Artificial Sequence
<220> FEATURE:
<223> OTHER INFORMATION: Ex6F Primer

<400> SEQUENCE: 15
tcctccttcc tctctctggc                                                      20

<210> SEQ ID NO 16
<211> LENGTH: 20
<212> TYPE: DNA
<213> ORGANISM: Artificial Sequence
<220> FEATURE:
<223> OTHER INFORMATION: Ex6R Primer

<400> SEQUENCE: 16
```
tctgcaagcc gcctgcaccg                                               20

<210> SEQ ID NO 17
<211> LENGTH: 23
<212> TYPE: DNA
<213> ORGANISM: Artificial Sequence
<220> FEATURE:
<223> OTHER INFORMATION: MutC255GF Primer

<400> SEQUENCE: 17
ctctggctct cacagtgaca cgc                                           23

<210> SEQ ID NO 18
<211> LENGTH: 20
<212> TYPE: DNA
<213> ORGANISM: Artificial Sequence
<220> FEATURE:
<223> OTHER INFORMATION: Mut E291XR Primer

<400> SEQUENCE: 18
gcaccgagac tcaccgcaat                                               20

<210> SEQ ID NO 19
<211> LENGTH: 20
<212> TYPE: DNA
<213> ORGANISM: Artificial Sequence
<220> FEATURE:
<223> OTHER INFORMATION: Ex7F Primer

<400> SEQUENCE: 19
ggcgaaggga tgggtagggg                                               20

<210> SEQ ID NO 20
<211> LENGTH: 20
<212> TYPE: DNA
<213> ORGANISM: Artificial Sequence
<220> FEATURE:
<223> OTHER INFORMATION: Ex7R Primer

<400> SEQUENCE: 20
gttgccatgt caggaagcgc                                               20

<210> SEQ ID NO 21
<211> LENGTH: 20
<212> TYPE: DNA
<213> ORGANISM: Artificial Sequence
<220> FEATURE:
<223> OTHER INFORMATION: Ex9F Primer

<400> SEQUENCE: 21
cccctgacct cgctccccgg                                               20

<210> SEQ ID NO 22
<211> LENGTH: 20
<212> TYPE: DNA
<213> ORGANISM: Artificial Sequence
<220> FEATURE:
<223> OTHER INFORMATION: Ex9R Primer

<400> SEQUENCE: 22
gctgcaggca ggggcgacgc                                               20

<210> SEQ ID NO 23
<211> LENGTH: 20
<212> TYPE: DNA
<213> ORGANISM: Artificial Sequence
<220> FEATURE:

```
<223> OTHER INFORMATION: Ex10F Primer

<400> SEQUENCE: 23
atgcccttct ctcctcctgc                                          20

<210> SEQ ID NO 24
<211> LENGTH: 20
<212> TYPE: DNA
<213> ORGANISM: Artificial Sequence
<220> FEATURE:
<223> OTHER INFORMATION: Ex10R Primer

<400> SEQUENCE: 24
agccctcagc gtcgtggata                                          20

<210> SEQ ID NO 25
<211> LENGTH: 20
<212> TYPE: DNA
<213> ORGANISM: Artificial Sequence
<220> FEATURE:
<223> OTHER INFORMATION: Mut1432delGF Primer

<400> SEQUENCE: 25
gggacatcca ggccccgcc                                           20

<210> SEQ ID NO 26
<211> LENGTH: 20
<212> TYPE: DNA
<213> ORGANISM: Artificial Sequence
<220> FEATURE:
<223> OTHER INFORMATION: Ex11F Primer

<400> SEQUENCE: 26 tcctccccg ccctccagcc                                           20

<210> SEQ ID NO 27
<211> LENGTH: 20
<212> TYPE: DNA
<213> ORGANISM: Artificial Sequence
<220> FEATURE:
<223> OTHER INFORMATION: Ex11R Primer

<400> SEQUENCE: 27
gctgggacgg ctgtcctgcg                                          20

<210> SEQ ID NO 28
<211> LENGTH: 20
<212> TYPE: DNA
<213> ORGANISM: Artificial Sequence
<220> FEATURE:
<223> OTHER INFORMATION: Ex13F Primer

<400> SEQUENCE: 28
gtcatcttcc ttgctgcctg                                          20

<210> SEQ ID NO 29
<211> LENGTH: 30
<212> TYPE: DNA
<213> ORGANISM: Artificial Sequence
<220> FEATURE:
<223> OTHER INFORMATION: Ex13R Primer

<400> SEQUENCE: 29
ttccacaagg aggtttcaag gttgggggg                                30

<210> SEQ ID NO 30
```

```
<211> LENGTH: 23
<212> TYPE: DNA
<213> ORGANISM: Artificial Sequence
<220> FEATURE:
<223> OTHER INFORMATION: MutH635NR Primer

<400> SEQUENCE: 30
acctcttggc tgggtcaggt tct                                          23

<210> SEQ ID NO 31
<211> LENGTH: 20
<212> TYPE: DNA
<213> ORGANISM: Artificial Sequence
<220> FEATURE:
<223> OTHER INFORMATION: Ex14F Primer

<400> SEQUENCE: 31
aaatttctgg aatcttctgg                                              20

<210> SEQ ID NO 32
<211> LENGTH: 20
<212> TYPE: DNA
<213> ORGANISM: Artificial Sequence
<220> FEATURE:
<223> OTHER INFORMATION: Ex14R Primer

<400> SEQUENCE: 32
gcagagagag gctcaggagg                                              20

<210> SEQ ID NO 33
<211> LENGTH: 22
<212> TYPE: DNA
<213> ORGANISM: Artificial Sequence
<220> FEATURE:
<223> OTHER INFORMATION: Ex15F Primer

<400> SEQUENCE: 33
gaagggcctg cagcacgtgg ca                                           22

<210> SEQ ID NO 34
<211> LENGTH: 19
<212> TYPE: DNA
<213> ORGANISM: Artificial Sequence
<220> FEATURE:
<223> OTHER INFORMATION: Ex15R Primer

<400> SEQUENCE: 34
tagggagggc ccagtctttt                                              19

<210> SEQ ID NO 35
<211> LENGTH: 20
<212> TYPE: DNA
<213> ORGANISM: Artificial Sequence
<220> FEATURE:
<223> OTHER INFORMATION: Ex17F Primer

<400> SEQUENCE: 35
gggtctctgg tctcgggggc                                              20

<210> SEQ ID NO 36
<211> LENGTH: 22
<212> TYPE: DNA
<213> ORGANISM: Artificial Sequence
<220> FEATURE:
<223> OTHER INFORMATION: Ex17R Primer

<400> SEQUENCE: 36
```

-continued ggctctggct ttctagagag gg                                        22

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
cgggtcggga cactgcctgg cag                                       23

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
cgggtcggga ccctgcctgg cag                                       23

<210> SEQ ID NO 39
<211> LENGTH: 23
<212> TYPE: DNA
<213> ORGANISM: Artificial Sequence
<220> FEATURE:
<223> OTHER INFORMATION: Primer

<400> SEQUENCE: 39
ctgccaggca gtgtcccgac ccg                                       23

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
ctgccaggca gggtcccgac ccg                                       23

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
atgcatttcc cgtcttggca ctg                                       23

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
gatgcatttc cctcttggca ctg                                       23

<210> SEQ ID NO 43
<211> LENGTH: 25
<212> TYPE: DNA
<213> ORGANISM: Artificial Sequence
<220> FEATURE:

-continued

<223> OTHER INFORMATION: Primer

<400> SEQUENCE: 43
gatgcatttc ccgtcttggc actgg                                    25

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
agatgcattt ccctcttggc actgg                                    25

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
tgtctcttct gtagtgtctg tcacc                                    25

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
gtctcttctg tctgtgtctg tcacc                                    25

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47
ctgtctcttc tgtagtgtct gtcacct                                  27

<210> SEQ ID NO 48
<211> LENGTH: 27
<212> TYPE: DNA
<213> ORGANISM: Artificial Sequence
<220> FEATURE:
<223> OTHER INFORMATION: Primer

<400> SEQUENCE: 48
tgtctcttct gtctgtgtct gtcacct                                  27

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
ggccgtgtca accgctgcat tcc                                      23

<210> SEQ ID NO 50

```
<211> LENGTH: 21
<212> TYPE: DNA
<213> ORGANISM: Artificial Sequence
<220> FEATURE:
<223> OTHER INFORMATION: Primer

<400> SEQUENCE: 50
gccgtgtcaa ccgctgcatt c                                              21

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
aggaatgcag cgtttgacac ggccc                                          25

<210> SEQ ID NO 52
<211> LENGTH: 27
<212> TYPE: DNA
<213> ORGANISM: Artificial Sequence
<220> FEATURE:
<223> OTHER INFORMATION: Primer

<400> SEQUENCE: 52
gaggaatgca gcgtttgaca cggcccc                                        27

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
agctgtgggg gccgtgtcaa ccg                                            23

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
agctgtgggg gcgtgtcaac cgc                                            23

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
cggttgacac ggcccccaca gct                                            23

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
```
gcggttgaca cgcccccaca gct    23

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
caaggctgtc gtaagtgtgg c    21

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
gcaaggctgt cgtaagtgtg gcc    23

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
caaggctgtc gttaagtgtg gcc    23

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
aaggctgtcg ttaagtgtgg c    21

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
gacaacgacc ccgactgcga agatg    25

<210> SEQ ID NO 62
<211> LENGTH: 25
<212> TYPE: DNA
<213> ORGANISM: Artificial Sequence
<220> FEATURE:
<223> OTHER INFORMATION: Primer

<400> SEQUENCE: 62
gacaacgacc cccgactgcg aagat    25

<210> SEQ ID NO 63
<211> LENGTH: 23
<212> TYPE: DNA
<213> ORGANISM: Artificial Sequence
<220> FEATURE:

<223> OTHER INFORMATION: Primer

<400> SEQUENCE: 63
acaacgaccc cgactgcgaa gat                    23

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
acaacgaccc ccgactgcga aga                    23

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
gcggccactc atccgagcca tct                    23

<210> SEQ ID NO 66
<211> LENGTH: 23
<212> TYPE: DNA
<213> ORGANISM: Artificial Sequence
<220> FEATURE:
<223> OTHER INFORMATION: Primer

<400> SEQUENCE: 66
gcggccactc acccgagcca tct                    23

<210> SEQ ID NO 67
<211> LENGTH: 25
<212> TYPE: DNA
<213> ORGANISM: Artificial Sequence
<220> FEATURE:
<223> OTHER INFORMATION: Primer

<400> SEQUENCE: 67
tgcggccact catccgagcc atctt                  25

<210> SEQ ID NO 68
<211> LENGTH: 25
<212> TYPE: DNA
<213> ORGANISM: Artificial Sequence
<220> FEATURE:
<223> OTHER INFORMATION: Primer

<400> SEQUENCE: 68
tgcggccact cacccgagcc atctt                  25

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69
ccagctggcg ctgtgatggt ggc                    23

<210> SEQ ID NO 70

```
-continued

<211> LENGTH: 23
<212> TYPE: DNA
<213> ORGANISM: Artificial Sequence
<220> FEATURE:
<223> OTHER INFORMATION: Primer

<400> SEQUENCE: 70
ccagctggcg ccgtgatggt ggc                                              23

<210> SEQ ID NO 71
<211> LENGTH: 25
<212> TYPE: DNA
<213> ORGANISM: Artificial Sequence
<220> FEATURE:
<223> OTHER INFORMATION: Primer

<400> SEQUENCE: 71
tccagctggc gctgtgatgg tggcc                                            25

<210> SEQ ID NO 72
<211> LENGTH: 25
<212> TYPE: DNA
<213> ORGANISM: Artificial Sequence
<220> FEATURE:
<223> OTHER INFORMATION: Primer

<400> SEQUENCE: 72
tccagctggc gccgtgatgg tggcc                                            25

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
ctgcaaggac aaatctgacg aggaa                                            25

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74
ctgcaaggac aactgcggta tgggc                                            25

<210> SEQ ID NO 75
<211> LENGTH: 27
<212> TYPE: DNA
<213> ORGANISM: Artificial Sequence
<220> FEATURE:
<223> OTHER INFORMATION: Primer

<400> SEQUENCE: 75
actgcaagga caaatctgac gaggaaa                                          27

<210> SEQ ID NO 76
<211> LENGTH: 27
<212> TYPE: DNA
<213> ORGANISM: Artificial Sequence
<220> FEATURE:
<223> OTHER INFORMATION: Primer

<400> SEQUENCE: 76
```
actgcaagga caactgcggt atgggcg 27

<210> SEQ ID NO 77
<211> LENGTH: 25
<212> TYPE: DNA
<213> ORGANISM: Artificial Sequence
<220> FEATURE:
<223> OTHER INFORMATION: Primer

<400> SEQUENCE: 77
caaatctgac gaggaaaact gcggt 25

<210> SEQ ID NO 78
<211> LENGTH: 25
<212> TYPE: DNA
<213> ORGANISM: Artificial Sequence
<220> FEATURE:
<223> OTHER INFORMATION: Primer

<400> SEQUENCE: 78
caaatctgac gacaaatctg acgag 25

<210> SEQ ID NO 79
<211> LENGTH: 27
<212> TYPE: DNA
<213> ORGANISM: Artificial Sequence
<220> FEATURE:
<223> OTHER INFORMATION: Primer

<400> SEQUENCE: 79
acaaatctga cgaggaaaac tgcggta 27

<210> SEQ ID NO 80
<211> LENGTH: 27
<212> TYPE: DNA
<213> ORGANISM: Artificial Sequence
<220> FEATURE:
<223> OTHER INFORMATION: Primer

<400> SEQUENCE: 80
acaaatctga cgacaaatct gacgagg 27

<210> SEQ ID NO 81
<211> LENGTH: 23
<212> TYPE: DNA
<213> ORGANISM: Artificial Sequence
<220> FEATURE:
<223> OTHER INFORMATION: Primer

<400> SEQUENCE: 81
gggtccctcg cagagtgtca ctg 23

<210> SEQ ID NO 82
<211> LENGTH: 23
<212> TYPE: DNA
<213> ORGANISM: Artificial Sequence
<220> FEATURE:
<223> OTHER INFORMATION: Primer

<400> SEQUENCE: 82
gggtccctcg ccgagtgtca ctg 23

<210> SEQ ID NO 83
<211> LENGTH: 25
<212> TYPE: DNA
<213> ORGANISM: Artificial Sequence
<220> FEATURE:

-continued

<223> OTHER INFORMATION: Primer

<400> SEQUENCE: 83
tgggtccctc gcagagtgtc actgt                                          25

<210> SEQ ID NO 84
<211> LENGTH: 25
<212> TYPE: DNA
<213> ORGANISM: Artificial Sequence
<220> FEATURE:
<223> OTHER INFORMATION: Primer

<400> SEQUENCE: 84
tgggtccctc gccgagtgtc actgt                                          25

<210> SEQ ID NO 85
<211> LENGTH: 23
<212> TYPE: DNA
<213> ORGANISM: Artificial Sequence
<220> FEATURE:
<223> OTHER INFORMATION: Primer

<400> SEQUENCE: 85
aacccatcaa agagtgcggt gag                                            23

<210> SEQ ID NO 86
<211> LENGTH: 23
<212> TYPE: DNA
<213> ORGANISM: Artificial Sequence
<220> FEATURE:
<223> OTHER INFORMATION: Primer

<400> SEQUENCE: 86
aacccatcaa atagtgcggt gag                                            23

<210> SEQ ID NO 87
<211> LENGTH: 25
<212> TYPE: DNA
<213> ORGANISM: Artificial Sequence
<220> FEATURE:
<223> OTHER INFORMATION: Primer

<400> SEQUENCE: 87
gaacccatca agagtgcgg tgagt                                           25

<210> SEQ ID NO 88
<211> LENGTH: 25
<212> TYPE: DNA
<213> ORGANISM: Artificial Sequence
<220> FEATURE:
<223> OTHER INFORMATION: Primer

<400> SEQUENCE: 88
gaacccatca aatagtgcgg tgagt                                          25

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
tcactctcgg gcccctacca                                                20

<210> SEQ ID NO 90

```
<211> LENGTH: 21
<212> TYPE: DNA
<213> ORGANISM: Artificial Sequence
<220> FEATURE:
<223> OTHER INFORMATION: Primer

<400> SEQUENCE: 90
tcactctcgg accccctaccc a                                             21

<210> SEQ ID NO 91
<211> LENGTH: 19
<212> TYPE: DNA
<213> ORGANISM: Artificial Sequence
<220> FEATURE:
<223> OTHER INFORMATION: Primer

<400> SEQUENCE: 91
cactctcggg cccctaccc                                                 19

<210> SEQ ID NO 92
<211> LENGTH: 19
<212> TYPE: DNA
<213> ORGANISM: Artificial Sequence
<220> FEATURE:
<223> OTHER INFORMATION: Primer

<400> SEQUENCE: 92
cactctcgga cccctaccc                                                 19

<210> SEQ ID NO 93
<211> LENGTH: 25
<212> TYPE: DNA
<213> ORGANISM: Artificial Sequence
<220> FEATURE:
<223> OTHER INFORMATION: Primer

<400> SEQUENCE: 93
acgagtgcct gtgcgccgac ggctt                                          25

<210> SEQ ID NO 94
<211> LENGTH: 25
<212> TYPE: DNA
<213> ORGANISM: Artificial Sequence
<220> FEATURE:
<223> OTHER INFORMATION: Primer

<400> SEQUENCE: 94
acgagtgcct gtacgccgac ggctt                                          25

<210> SEQ ID NO 95
<211> LENGTH: 23
<212> TYPE: DNA
<213> ORGANISM: Artificial Sequence
<220> FEATURE:
<223> OTHER INFORMATION: Primer

<400> SEQUENCE: 95
cgagtgcctg tgcgccgacg gct                                            23

<210> SEQ ID NO 96
<211> LENGTH: 23
<212> TYPE: DNA
<213> ORGANISM: Artificial Sequence
<220> FEATURE:
<223> OTHER INFORMATION: Primer

<400> SEQUENCE: 96
```
cgagtgcctg tacgccgacg gct    23

<210> SEQ ID NO 97
<211> LENGTH: 24
<212> TYPE: DNA
<213> ORGANISM: Artificial Sequence
<220> FEATURE:
<223> OTHER INFORMATION: Primer

<400> SEQUENCE: 97
gcgaagatgc aaggtgatt ccgg    24

<210> SEQ ID NO 98
<211> LENGTH: 25
<212> TYPE: DNA
<213> ORGANISM: Artificial Sequence
<220> FEATURE:
<223> OTHER INFORMATION: Primer

<400> SEQUENCE: 98
ggcccagcga agatttccgg gtggg    25

<210> SEQ ID NO 99
<211> LENGTH: 27
<212> TYPE: DNA
<213> ORGANISM: Artificial Sequence
<220> FEATURE:
<223> OTHER INFORMATION: Primer

<400> SEQUENCE: 99
agcgaagatg cgaaggtgat ttccggg    27

<210> SEQ ID NO 100
<211> LENGTH: 27
<212> TYPE: DNA
<213> ORGANISM: Artificial Sequence
<220> FEATURE:
<223> OTHER INFORMATION: Primer

<400> SEQUENCE: 100
tggcccagcg aagatttccg ggtggga    27

<210> SEQ ID NO 101
<211> LENGTH: 21
<212> TYPE: DNA
<213> ORGANISM: Artificial Sequence
<220> FEATURE:
<223> OTHER INFORMATION: Primer

<400> SEQUENCE: 101
tgaagaagag gtaggcgatg g    21

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
cggttggtga agacgatgga g    21

<210> SEQ ID NO 103
<211> LENGTH: 23
<212> TYPE: DNA
<213> ORGANISM: Artificial Sequence
<220> FEATURE:

<223> OTHER INFORMATION: Primer

<400> SEQUENCE: 103
gtgaagaaga ggtaggcgat gga                                        23

<210> SEQ ID NO 104
<211> LENGTH: 23
<212> TYPE: DNA
<213> ORGANISM: Artificial Sequence
<220> FEATURE:
<223> OTHER INFORMATION: Primer

<400> SEQUENCE: 104
ccggttggtg aagacgatgg agc                                        23

<210> SEQ ID NO 105
<211> LENGTH: 25
<212> TYPE: DNA
<213> ORGANISM: Artificial Sequence
<220> FEATURE:
<223> OTHER INFORMATION: Primer

<400> SEQUENCE: 105
ctccatcgcc tacctcttct tcacc                                      25

<210> SEQ ID NO 106
<211> LENGTH: 25
<212> TYPE: DNA
<213> ORGANISM: Artificial Sequence
<220> FEATURE:
<223> OTHER INFORMATION: Primer

<400> SEQUENCE: 106
ctccatcgcc taactcttct tcacc                                      25

<210> SEQ ID NO 107
<211> LENGTH: 27
<212> TYPE: DNA
<213> ORGANISM: Artificial Sequence
<220> FEATURE:
<223> OTHER INFORMATION: Primer

<400> SEQUENCE: 107
gctccatcgc ctacctcttc ttcacca                                    27

<210> SEQ ID NO 108
<211> LENGTH: 27
<212> TYPE: DNA
<213> ORGANISM: Artificial Sequence
<220> FEATURE:
<223> OTHER INFORMATION: Primer

<400> SEQUENCE: 108
gctccatcgc ctaactcttc ttcacca                                    27

<210> SEQ ID NO 109
<211> LENGTH: 25
<212> TYPE: DNA
<213> ORGANISM: Artificial Sequence
<220> FEATURE:
<223> OTHER INFORMATION: Primer

<400> SEQUENCE: 109
tgccggttgg tgaagaagag gtagg                                      25

<210> SEQ ID NO 110

```
<211> LENGTH: 25
<212> TYPE: DNA
<213> ORGANISM: Artificial Sequence
<220> FEATURE:
<223> OTHER INFORMATION: Primer

<400> SEQUENCE: 110
gtgccggttg gtgagaagag gtagg                                          25

<210> SEQ ID NO 111
<211> LENGTH: 27
<212> TYPE: DNA
<213> ORGANISM: Artificial Sequence
<220> FEATURE:
<223> OTHER INFORMATION: Primer

<400> SEQUENCE: 111
gtgccggttg gtgaagaaga ggtaggc                                        27

<210> SEQ ID NO 112
<211> LENGTH: 27
<212> TYPE: DNA
<213> ORGANISM: Artificial Sequence
<220> FEATURE:
<223> OTHER INFORMATION: Primer

<400> SEQUENCE: 112
cgtgccggtt ggtgagaaga ggtaggc                                        27

<210> SEQ ID NO 113
<211> LENGTH: 25
<212> TYPE: DNA
<213> ORGANISM: Artificial Sequence
<220> FEATURE:
<223> OTHER INFORMATION: Primer

<400> SEQUENCE: 113
caatagaatc tactggtctg acctg                                          25

<210> SEQ ID NO 114
<211> LENGTH: 25
<212> TYPE: DNA
<213> ORGANISM: Artificial Sequence
<220> FEATURE:
<223> OTHER INFORMATION: Primer

<400> SEQUENCE: 114
caatagaatc tagtggtctg acctg                                          25

<210> SEQ ID NO 115
<211> LENGTH: 27
<212> TYPE: DNA
<213> ORGANISM: Artificial Sequence
<220> FEATURE:
<223> OTHER INFORMATION: Primer

<400> SEQUENCE: 115
gcaatagaat ctactggtct gacctgt                                        27

<210> SEQ ID NO 116
<211> LENGTH: 27
<212> TYPE: DNA
<213> ORGANISM: Artificial Sequence
<220> FEATURE:
<223> OTHER INFORMATION: Primer

<400> SEQUENCE: 116
```

-continued gcaatagaat ctagtggtct gacctgt                                27

<210> SEQ ID NO 117
<211> LENGTH: 25
<212> TYPE: DNA
<213> ORGANISM: Artificial Sequence
<220> FEATURE:
<223> OTHER INFORMATION: Primer

<400> SEQUENCE: 117
ggcccccgac gggctggctg tggac                                  25

<210> SEQ ID NO 118
<211> LENGTH: 25
<212> TYPE: DNA
<213> ORGANISM: Artificial Sequence
<220> FEATURE:
<223> OTHER INFORMATION: Primer

<400> SEQUENCE: 118
ggcccccgac ggctggctgt ggact                                  25

<210> SEQ ID NO 119
<211> LENGTH: 25
<212> TYPE: DNA
<213> ORGANISM: Artificial Sequence
<220> FEATURE:
<223> OTHER INFORMATION: Primer

<400> SEQUENCE: 119
gtccacagcc agcccgtcgg gggcc                                  25

<210> SEQ ID NO 120
<211> LENGTH: 25
<212> TYPE: DNA
<213> ORGANISM: Artificial Sequence
<220> FEATURE:
<223> OTHER INFORMATION: Primer

<400> SEQUENCE: 120
agtccacagc cagccgtcgg gggcc                                  25

<210> SEQ ID NO 121
<211> LENGTH: 25
<212> TYPE: DNA
<213> ORGANISM: Artificial Sequence
<220> FEATURE:
<223> OTHER INFORMATION: Primer

<400> SEQUENCE: 121
gcgggagttc cccagtcagt ccagt                                  25

<210> SEQ ID NO 122
<211> LENGTH: 25
<212> TYPE: DNA
<213> ORGANISM: Artificial Sequence
<220> FEATURE:
<223> OTHER INFORMATION: Primer

<400> SEQUENCE: 122
gcgggagttc cctagtcagt ccagt                                  25

<210> SEQ ID NO 123
<211> LENGTH: 23
<212> TYPE: DNA
<213> ORGANISM: Artificial Sequence
<220> FEATURE:

<223> OTHER INFORMATION: Primer

<400> SEQUENCE: 123
cgggagttcc ccagtcagtc cag                                    23

<210> SEQ ID NO 124
<211> LENGTH: 23
<212> TYPE: DNA
<213> ORGANISM: Artificial Sequence
<220> FEATURE:
<223> OTHER INFORMATION: Primer

<400> SEQUENCE: 124
cgggagttcc ctagtcagtc cag                                    23

<210> SEQ ID NO 125
<211> LENGTH: 25
<212> TYPE: DNA
<213> ORGANISM: Artificial Sequence
<220> FEATURE:
<223> OTHER INFORMATION: Primer

<400> SEQUENCE: 125
ctgtccccag aggatatggt tctct                                  25

<210> SEQ ID NO 126
<211> LENGTH: 25
<212> TYPE: DNA
<213> ORGANISM: Artificial Sequence
<220> FEATURE:
<223> OTHER INFORMATION: Primer

<400> SEQUENCE: 126
ctgtccccag agaatatggt tctct                                  25

<210> SEQ ID NO 127
<211> LENGTH: 23
<212> TYPE: DNA
<213> ORGANISM: Artificial Sequence
<220> FEATURE:
<223> OTHER INFORMATION: Primer

<400> SEQUENCE: 127
tgtccccaga ggatatggtt ctc                                    23

<210> SEQ ID NO 128
<211> LENGTH: 23
<212> TYPE: DNA
<213> ORGANISM: Artificial Sequence
<220> FEATURE:
<223> OTHER INFORMATION: Primer

<400> SEQUENCE: 128
tgtccccaga gaatatggtt ctc                                    23

<210> SEQ ID NO 129
<211> LENGTH: 23
<212> TYPE: DNA
<213> ORGANISM: Artificial Sequence
<220> FEATURE:
<223> OTHER INFORMATION: Primer

<400> SEQUENCE: 129
tggttctctt ccacaacctc acc                                    23

<210> SEQ ID NO 130

```
<211> LENGTH: 23
<212> TYPE: DNA
<213> ORGANISM: Artificial Sequence
<220> FEATURE:
<223> OTHER INFORMATION: Primer

<400> SEQUENCE: 130
tggttctctt caacaacctc acc                                          23

<210> SEQ ID NO 131
<211> LENGTH: 25
<212> TYPE: DNA
<213> ORGANISM: Artificial Sequence
<220> FEATURE:
<223> OTHER INFORMATION: Primer

<400> SEQUENCE: 131
atggttctct tccacaacct caccc                                        25

<210> SEQ ID NO 132
<211> LENGTH: 25
<212> TYPE: DNA
<213> ORGANISM: Artificial Sequence
<220> FEATURE:
<223> OTHER INFORMATION: Primer

<400> SEQUENCE: 132
atggttctct tcaacaacct caccc                                        25

<210> SEQ ID NO 133
<211> LENGTH: 25
<212> TYPE: DNA
<213> ORGANISM: Artificial Sequence
<220> FEATURE:
<223> OTHER INFORMATION: Primer

<400> SEQUENCE: 133
gctgaccttt agcctgacgg tggat                                        25

<210> SEQ ID NO 134
<211> LENGTH: 25
<212> TYPE: DNA
<213> ORGANISM: Artificial Sequence
<220> FEATURE:
<223> OTHER INFORMATION: Primer

<400> SEQUENCE: 134
agctgacctt tagctgacgg tggat                                        25

<210> SEQ ID NO 135
<211> LENGTH: 27
<212> TYPE: DNA
<213> ORGANISM: Artificial Sequence
<220> FEATURE:
<223> OTHER INFORMATION: Primer

<400> SEQUENCE: 135
agctgacctt tagcctgacg gtggatg                                      27

<210> SEQ ID NO 136
<211> LENGTH: 27
<212> TYPE: DNA
<213> ORGANISM: Artificial Sequence
<220> FEATURE:
<223> OTHER INFORMATION: Primer

<400> SEQUENCE: 136
```
gagctgacct ttagctgacg gtggatg                                    27

<210> SEQ ID NO 137
<211> LENGTH: 23
<212> TYPE: DNA
<213> ORGANISM: Artificial Sequence
<220> FEATURE:
<223> OTHER INFORMATION: Primer

<400> SEQUENCE: 137
tgctcctcgt cttcctttgc ctg                                        23

<210> SEQ ID NO 138
<211> LENGTH: 23
<212> TYPE: DNA
<213> ORGANISM: Artificial Sequence
<220> FEATURE:
<223> OTHER INFORMATION: Primer

<400> SEQUENCE: 138
tgctcctcgg ggtctttgcc tgg                                        23

<210> SEQ ID NO 139
<211> LENGTH: 25
<212> TYPE: DNA
<213> ORGANISM: Artificial Sequence
<220> FEATURE:
<223> OTHER INFORMATION: Primer

<400> SEQUENCE: 139
gtgctcctcg tcttcctttg cctgg                                      25

<210> SEQ ID NO 140
<211> LENGTH: 25
<212> TYPE: DNA
<213> ORGANISM: Artificial Sequence
<220> FEATURE:
<223> OTHER INFORMATION: Primer

<400> SEQUENCE: 140
gtgctcctcg gggtctttgc ctggg                                      25

<210> SEQ ID NO 141
<211> LENGTH: 25
<212> TYPE: DNA
<213> ORGANISM: Artificial Sequence
<220> FEATURE:
<223> OTHER INFORMATION: Primer

<400> SEQUENCE: 141
gactcacagc acgtctcctg ggact                                      25

<210> SEQ ID NO 142
<211> LENGTH: 25
<212> TYPE: DNA
<213> ORGANISM: Artificial Sequence
<220> FEATURE:
<223> OTHER INFORMATION: Primer

<400> SEQUENCE: 142
gactcacagc acatctcctg ggact                                      25

<210> SEQ ID NO 143
<211> LENGTH: 23
<212> TYPE: DNA
<213> ORGANISM: Artificial Sequence
<220> FEATURE:

<223> OTHER INFORMATION: Primer

<400> SEQUENCE: 143
actcacagca cgtctcctgg gac                                    23

<210> SEQ ID NO 144
<211> LENGTH: 23
<212> TYPE: DNA
<213> ORGANISM: Artificial Sequence
<220> FEATURE:
<223> OTHER INFORMATION: Primer

<400> SEQUENCE: 144
actcacagca catctcctgg gac                                    23

<210> SEQ ID NO 145
<211> LENGTH: 23
<212> TYPE: DNA
<213> ORGANISM: Artificial Sequence
<220> FEATURE:
<223> OTHER INFORMATION: Primer

<400> SEQUENCE: 145
ccatcgtggc agcgaaactc gtc                                    23

<210> SEQ ID NO 146
<211> LENGTH: 23
<212> TYPE: DNA
<213> ORGANISM: Artificial Sequence
<220> FEATURE:
<223> OTHER INFORMATION: Primer

<400> SEQUENCE: 146
atgcacttcc cacgtcctgg gag                                    23

<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147
catcgtggca gcgaaactcg t                                      21

<210> SEQ ID NO 148
<211> LENGTH: 21
<212> TYPE: DNA
<213> ORGANISM: Artificial Sequence
<220> FEATURE:
<223> OTHER INFORMATION: Primer

<400> SEQUENCE: 148
tgcacttccc acgtcctggg a                                      21

<210> SEQ ID NO 149
<211> LENGTH: 20
<212> TYPE: DNA
<213> ORGANISM: Artificial Sequence
<220> FEATURE:
<223> OTHER INFORMATION: Ex8F Primer

<400> SEQUENCE: 149
cattggggaa gagcctcccc                                        20

<210> SEQ ID NO 150

```
<211> LENGTH: 20
<212> TYPE: DNA
<213> ORGANISM: Artificial Sequence
<220> FEATURE:
<223> OTHER INFORMATION: Ex8R Primer

<400> SEQUENCE: 150
gcctgcaagg ggtgaggccg                                              20

<210> SEQ ID NO 151
<211> LENGTH: 20
<212> TYPE: DNA
<213> ORGANISM: Artificial Sequence
<220> FEATURE:
<223> OTHER INFORMATION: Ex12F Primer

<400> SEQUENCE: 151
actggcatca gcacgtgacc                                              20

<210> SEQ ID NO 152
<211> LENGTH: 20
<212> TYPE: DNA
<213> ORGANISM: Artificial Sequence
<220> FEATURE:
<223> OTHER INFORMATION: Ex12R Primer

<400> SEQUENCE: 152
cgtgtgtcta tccggccacc                                              20

<210> SEQ ID NO 153
<211> LENGTH: 20
<212> TYPE: DNA
<213> ORGANISM: Artificial Sequence
<220> FEATURE:
<223> OTHER INFORMATION: Ex16F Primer

<400> SEQUENCE: 153
gcgctttcct gccgtgacca                                              20

<210> SEQ ID NO 154
<211> LENGTH: 23
<212> TYPE: DNA
<213> ORGANISM: Artificial Sequence
<220> FEATURE:
<223> OTHER INFORMATION: Ex16R Primer

<400> SEQUENCE: 154
cctgtccagg agaaaaagtg aac                                          23

<210> SEQ ID NO 155
<211> LENGTH: 23
<212> TYPE: DNA
<213> ORGANISM: Artificial Sequence
<220> FEATURE:
<223> OTHER INFORMATION: MutI771TF Primer

<400> SEQUENCE: 155
cagtagcgtg agggctctgt caa                                          23

<210> SEQ ID NO 156
<211> LENGTH: 19
<212> TYPE: DNA
<213> ORGANISM: Artificial Sequence
<220> FEATURE:
<223> OTHER INFORMATION: Mut2389+4A>GR Primer

<400> SEQUENCE: 156
```

-continued

```
ctgggggacc ggccggcgc                                                19

<210> SEQ ID NO 157
<211> LENGTH: 23
<212> TYPE: DNA
<213> ORGANISM: Artificial Sequence
<220> FEATURE:
<223> OTHER INFORMATION: Primer

<400> SEQUENCE: 157
tgtcaagctg ggtgctgagg cag                                           23

<210> SEQ ID NO 158
<211> LENGTH: 23
<212> TYPE: DNA
<213> ORGANISM: Artificial Sequence
<220> FEATURE:
<223> OTHER INFORMATION: Primer

<400> SEQUENCE: 158
tgtcaagctg gttgctgagg cag                                           23

<210> SEQ ID NO 159
<211> LENGTH: 21
<212> TYPE: DNA
<213> ORGANISM: Artificial Sequence
<220> FEATURE:
<223> OTHER INFORMATION: Primer

<400> SEQUENCE: 159
gtcaagctgg gtgctgaggc a                                             21

<210> SEQ ID NO 160
<211> LENGTH: 21
<212> TYPE: DNA
<213> ORGANISM: Artificial Sequence
<220> FEATURE:
<223> OTHER INFORMATION: Primer

<400> SEQUENCE: 160
gtcaagctgg ttgctgaggc a                                             21

<210> SEQ ID NO 161
<211> LENGTH: 23
<212> TYPE: DNA
<213> ORGANISM: Artificial Sequence
<220> FEATURE:
<223> OTHER INFORMATION: Primer

<400> SEQUENCE: 161
ggtccctcgc agagtgtcac tgt                                           23

<210> SEQ ID NO 162
<211> LENGTH: 23
<212> TYPE: DNA
<213> ORGANISM: Artificial Sequence
<220> FEATURE:
<223> OTHER INFORMATION: Primer

<400> SEQUENCE: 162
ggtccctcgc actgtgagag cca                                           23

<210> SEQ ID NO 163
<211> LENGTH: 21
<212> TYPE: DNA
<213> ORGANISM: Artificial Sequence
<220> FEATURE:
```

<223> OTHER INFORMATION: Primer

<400> SEQUENCE: 163
gtccctcgca gagtgtcact g                                              21

<210> SEQ ID NO 164
<211> LENGTH: 21
<212> TYPE: DNA
<213> ORGANISM: Artificial Sequence
<220> FEATURE:
<223> OTHER INFORMATION: Primer

<400> SEQUENCE: 164
gtccctcgca ctgtgagagc c                                              21

<210> SEQ ID NO 165
<211> LENGTH: 21
<212> TYPE: DNA
<213> ORGANISM: Artificial Sequence
<220> FEATURE:
<223> OTHER INFORMATION: Primer

<400> SEQUENCE: 165
ccgtcggggg cctggatgtc t                                              21

<210> SEQ ID NO 166
<211> LENGTH: 21
<212> TYPE: DNA
<213> ORGANISM: Artificial Sequence
<220> FEATURE:
<223> OTHER INFORMATION: Primer

<400> SEQUENCE: 166
cccgtcgggg tctggatgtc t                                              21

<210> SEQ ID NO 167
<211> LENGTH: 23
<212> TYPE: DNA
<213> ORGANISM: Artificial Sequence
<220> FEATURE:
<223> OTHER INFORMATION: Primer

<400> SEQUENCE: 167
cccgtcgggg gcctggatgt ctc                                            23

<210> SEQ ID NO 168
<211> LENGTH: 23
<212> TYPE: DNA
<213> ORGANISM: Artificial Sequence
<220> FEATURE:
<223> OTHER INFORMATION: Primer

<400> SEQUENCE: 168
gcccgtcggg gtctggatgt ctc                                            23

<210> SEQ ID NO 169
<211> LENGTH: 25
<212> TYPE: DNA
<213> ORGANISM: Artificial Sequence
<220> FEATURE:
<223> OTHER INFORMATION: Primer

<400> SEQUENCE: 169
ccggttggtg aagaagaggt aggcg                                          25

<210> SEQ ID NO 170

```
<211> LENGTH: 25
<212> TYPE: DNA
<213> ORGANISM: Artificial Sequence
<220> FEATURE:
<223> OTHER INFORMATION: Primer

<400> SEQUENCE: 170
cggttggtga agaaagaggt aggcg                                           25

<210> SEQ ID NO 171
<211> LENGTH: 27
<212> TYPE: DNA
<213> ORGANISM: Artificial Sequence
<220> FEATURE:
<223> OTHER INFORMATION: Primer

<400> SEQUENCE: 171
gccggttggt gaagaagagg taggcga                                         27

<210> SEQ ID NO 172
<211> LENGTH: 27
<212> TYPE: DNA
<213> ORGANISM: Artificial Sequence
<220> FEATURE:
<223> OTHER INFORMATION: Primer

<400> SEQUENCE: 172
ccggttggtg aagaaagagg taggcga                                         27

<210> SEQ ID NO 173
<211> LENGTH: 23
<212> TYPE: DNA
<213> ORGANISM: Artificial Sequence
<220> FEATURE:
<223> OTHER INFORMATION: Primer

<400> SEQUENCE: 173
actggaagct ggcgggacca cag                                             23

<210> SEQ ID NO 174
<211> LENGTH: 23
<212> TYPE: DNA
<213> ORGANISM: Artificial Sequence
<220> FEATURE:
<223> OTHER INFORMATION: Primer

<400> SEQUENCE: 174
gcactggaag ctgggaccac agg                                             23

<210> SEQ ID NO 175
<211> LENGTH: 23
<212> TYPE: DNA
<213> ORGANISM: Artificial Sequence
<220> FEATURE:
<223> OTHER INFORMATION: Primer

<400> SEQUENCE: 175
ctgtggtccc gccagcttcc agt                                             23

<210> SEQ ID NO 176
<211> LENGTH: 23
<212> TYPE: DNA
<213> ORGANISM: Artificial Sequence
<220> FEATURE:
<223> OTHER INFORMATION: Primer

<400> SEQUENCE: 176
```
cctgtggtcc cagcttccag tgc                                                23

<210> SEQ ID NO 177
<211> LENGTH: 21
<212> TYPE: DNA
<213> ORGANISM: Artificial Sequence
<220> FEATURE:
<223> OTHER INFORMATION: Primer

<400> SEQUENCE: 177
gcgggagttc cccagtcagt c                                                  21

<210> SEQ ID NO 178
<211> LENGTH: 21
<212> TYPE: DNA
<213> ORGANISM: Artificial Sequence
<220> FEATURE:
<223> OTHER INFORMATION: Primer

<400> SEQUENCE: 178
gcgggagttc accagtcagt c                                                  21

<210> SEQ ID NO 179
<211> LENGTH: 23
<212> TYPE: DNA
<213> ORGANISM: Artificial Sequence
<220> FEATURE:
<223> OTHER INFORMATION: Primer

<400> SEQUENCE: 179
ggcgggagtt ccccagtcag tcc                                                23

<210> SEQ ID NO 180
<211> LENGTH: 23
<212> TYPE: DNA
<213> ORGANISM: Artificial Sequence
<220> FEATURE:
<223> OTHER INFORMATION: Primer

<400> SEQUENCE: 180
ggcgggagtt caccagtcag tcc                                                23

<210> SEQ ID NO 181
<211> LENGTH: 23
<212> TYPE: DNA
<213> ORGANISM: Artificial Sequence
<220> FEATURE:
<223> OTHER INFORMATION: Primer

<400> SEQUENCE: 181
ccccatcggt aagcgcgggc cgg                                                23

<210> SEQ ID NO 182
<211> LENGTH: 23
<212> TYPE: DNA
<213> ORGANISM: Artificial Sequence
<220> FEATURE:
<223> OTHER INFORMATION: Primer

<400> SEQUENCE: 182
ccccatcggt aggcgcgggc cgg                                                23

<210> SEQ ID NO 183
<211> LENGTH: 23
<212> TYPE: DNA
<213> ORGANISM: Artificial Sequence
<220> FEATURE:

<223> OTHER INFORMATION: Primer

<400> SEQUENCE: 183
ccggcccgcg cttaccgatg ggg                                    23

<210> SEQ ID NO 184
<211> LENGTH: 23
<212> TYPE: DNA
<213> ORGANISM: Artificial Sequence
<220> FEATURE:
<223> OTHER INFORMATION: Primer

<400> SEQUENCE: 184
ccggcccgcg cctaccgatg ggg                                    23

<210> SEQ ID NO 185
<211> LENGTH: 23
<212> TYPE: DNA
<213> ORGANISM: Artificial Sequence
<220> FEATURE:
<223> OTHER INFORMATION: Primer

<400> SEQUENCE: 185
gaaaagaggc tggcccaccc ctt                                    23

<210> SEQ ID NO 186
<211> LENGTH: 23
<212> TYPE: DNA
<213> ORGANISM: Artificial Sequence
<220> FEATURE:
<223> OTHER INFORMATION: Primer

<400> SEQUENCE: 186
gaaaagaggc ttctccttgg ccg                                    23

<210> SEQ ID NO 187
<211> LENGTH: 21
<212> TYPE: DNA
<213> ORGANISM: Artificial Sequence
<220> FEATURE:
<223> OTHER INFORMATION: Primer

<400> SEQUENCE: 187
aaaagaggct ggcccacccc t                                      21

<210> SEQ ID NO 188
<211> LENGTH: 21
<212> TYPE: DNA
<213> ORGANISM: Artificial Sequence
<220> FEATURE:
<223> OTHER INFORMATION: Primer

<400> SEQUENCE: 188
aaaagaggct tctccttggc c                                      21

<210> SEQ ID NO 189
<211> LENGTH: 25
<212> TYPE: DNA
<213> ORGANISM: Artificial Sequence
<220> FEATURE:
<223> OTHER INFORMATION: Primer

<400> SEQUENCE: 189
cgccttcccg tgctcaccca cagcc                                  25

<210> SEQ ID NO 190

```
<211> LENGTH: 25
<212> TYPE: DNA
<213> ORGANISM: Artificial Sequence
<220> FEATURE:
<223> OTHER INFORMATION: Primer

<400> SEQUENCE: 190
cgccttcccg tgttcaccca cagcc                                        25

<210> SEQ ID NO 191
<211> LENGTH: 25
<212> TYPE: DNA
<213> ORGANISM: Artificial Sequence
<220> FEATURE:
<223> OTHER INFORMATION: Primer

<400> SEQUENCE: 191
ggctgtgggt gagcacggga aggcg                                        25

<210> SEQ ID NO 192
<211> LENGTH: 25
<212> TYPE: DNA
<213> ORGANISM: Artificial Sequence
<220> FEATURE:
<223> OTHER INFORMATION: Primer

<400> SEQUENCE: 192
ggctgtgggt gaccacggga aggcg                                        25

<210> SEQ ID NO 193
<211> LENGTH: 25
<212> TYPE: DNA
<213> ORGANISM: Artificial Sequence
<220> FEATURE:
<223> OTHER INFORMATION: Primer

<400> SEQUENCE: 193
actatctcca ccgtggtgag cccag                                        25

<210> SEQ ID NO 194
<211> LENGTH: 25
<212> TYPE: DNA
<213> ORGANISM: Artificial Sequence
<220> FEATURE:
<223> OTHER INFORMATION: Primer

<400> SEQUENCE: 194
actatctcca ccatggtgag cccag                                        25

<210> SEQ ID NO 195
<211> LENGTH: 25
<212> TYPE: DNA
<213> ORGANISM: Artificial Sequence
<220> FEATURE:
<223> OTHER INFORMATION: Primer

<400> SEQUENCE: 195
ctgggctcac cacggtggag atagt                                        25

<210> SEQ ID NO 196
<211> LENGTH: 25
<212> TYPE: DNA
<213> ORGANISM: Artificial Sequence
<220> FEATURE:
<223> OTHER INFORMATION: Primer

<400> SEQUENCE: 196
```

```
ctgggctcac catggtggag atagt                                      25

<210> SEQ ID NO 197
<211> LENGTH: 25
<212> TYPE: DNA
<213> ORGANISM: Artificial Sequence
<220> FEATURE:
<223> OTHER INFORMATION: Primer

<400> SEQUENCE: 197
gggctctgtc cattgtcctc cccat                                      25

<210> SEQ ID NO 198
<211> LENGTH: 25
<212> TYPE: DNA
<213> ORGANISM: Artificial Sequence
<220> FEATURE:
<223> OTHER INFORMATION: Primer

<400> SEQUENCE: 198
gggctctgtc cactgtcctc cccat                                      25

<210> SEQ ID NO 199
<211> LENGTH: 25
<212> TYPE: DNA
<213> ORGANISM: Artificial Sequence
<220> FEATURE:
<223> OTHER INFORMATION: Primer

<400> SEQUENCE: 199
atggggagga caatggacag agccc                                      25

<210> SEQ ID NO 200
<211> LENGTH: 25
<212> TYPE: DNA
<213> ORGANISM: Artificial Sequence
<220> FEATURE:
<223> OTHER INFORMATION: Primer

<400> SEQUENCE: 200
atggggagga cagtggacag agccc                                      25

<210> SEQ ID NO 201
<211> LENGTH: 25
<212> TYPE: DNA
<213> ORGANISM: Artificial Sequence
<220> FEATURE:
<223> OTHER INFORMATION: Primer

<400> SEQUENCE: 201
tgcaacatgg ctagagactg ccggg                                      25

<210> SEQ ID NO 202
<211> LENGTH: 25
<212> TYPE: DNA
<213> ORGANISM: Artificial Sequence
<220> FEATURE:
<223> OTHER INFORMATION: Primer

<400> SEQUENCE: 202
tgcaacatgg ctggagactg ccggg                                      25

<210> SEQ ID NO 203
<211> LENGTH: 23
<212> TYPE: DNA
<213> ORGANISM: Artificial Sequence
<220> FEATURE:
```

<223> OTHER INFORMATION: Primer

<400> SEQUENCE: 203
gcaacatggc tagagactgc cgg                                    23

<210> SEQ ID NO 204
<211> LENGTH: 23
<212> TYPE: DNA
<213> ORGANISM: Artificial Sequence
<220> FEATURE:
<223> OTHER INFORMATION: Primer

<400> SEQUENCE: 204
gcaacatggc tggagactgc cgg                                    23

<210> SEQ ID NO 205
<211> LENGTH: 23
<212> TYPE: DNA
<213> ORGANISM: Artificial Sequence
<220> FEATURE:
<223> OTHER INFORMATION: Primer

<400> SEQUENCE: 205
tgctgatgac ggtgtcatag gaa                                    23

<210> SEQ ID NO 206
<211> LENGTH: 23
<212> TYPE: DNA
<213> ORGANISM: Artificial Sequence
<220> FEATURE:
<223> OTHER INFORMATION: Primer

<400> SEQUENCE: 206
tgctgatgac gatgtcatag gaa                                    23

<210> SEQ ID NO 207
<211> LENGTH: 21
<212> TYPE: DNA
<213> ORGANISM: Artificial Sequence
<220> FEATURE:
<223> OTHER INFORMATION: Primer

<400> SEQUENCE: 207
gctgatgacg gtgtcatagg a                                      21

<210> SEQ ID NO 208
<211> LENGTH: 21
<212> TYPE: DNA
<213> ORGANISM: Artificial Sequence
<220> FEATURE:
<223> OTHER INFORMATION: Primer

<400> SEQUENCE: 208
gctgatgacg atgtcatagg a                                      21

<210> SEQ ID NO 209
<211> LENGTH: 23
<212> TYPE: DNA
<213> ORGANISM: Artificial Sequence
<220> FEATURE:
<223> OTHER INFORMATION: Primer

<400> SEQUENCE: 209
tccaaacttc actccatctc aag                                    23

<210> SEQ ID NO 210

```
<211> LENGTH: 23
<212> TYPE: DNA
<213> ORGANISM: Artificial Sequence
<220> FEATURE:
<223> OTHER INFORMATION: Primer

<400> SEQUENCE: 210
tccaaacttc agtccatctc aag                                              23

<210> SEQ ID NO 211
<211> LENGTH: 23
<212> TYPE: DNA
<213> ORGANISM: Artificial Sequence
<220> FEATURE:
<223> OTHER INFORMATION: Primer

<400> SEQUENCE: 211
cttgagatgg agtgaagttt gga                                              23

<210> SEQ ID NO 212
<211> LENGTH: 23
<212> TYPE: DNA
<213> ORGANISM: Artificial Sequence
<220> FEATURE:
<223> OTHER INFORMATION: Primer

<400> SEQUENCE: 212
cttgagatgg actgaagttt gga                                              23

<210> SEQ ID NO 213
<211> LENGTH: 25
<212> TYPE: DNA
<213> ORGANISM: Artificial Sequence
<220> FEATURE:
<223> OTHER INFORMATION: Primer

<400> SEQUENCE: 213
gccaagtgga ctgcgacaac ggctc                                            25

<210> SEQ ID NO 214
<211> LENGTH: 25
<212> TYPE: DNA
<213> ORGANISM: Artificial Sequence
<220> FEATURE:
<223> OTHER INFORMATION: Primer

<400> SEQUENCE: 214
gccaagtgga ctacgacaac ggctc                                            25

<210> SEQ ID NO 215
<211> LENGTH: 25
<212> TYPE: DNA
<213> ORGANISM: Artificial Sequence
<220> FEATURE:
<223> OTHER INFORMATION: Primer

<400> SEQUENCE: 215
gagccgttgt cgcagtccac ttggc                                            25

<210> SEQ ID NO 216
<211> LENGTH: 25
<212> TYPE: DNA
<213> ORGANISM: Artificial Sequence
<220> FEATURE:
<223> OTHER INFORMATION: Primer

<400> SEQUENCE: 216
```
gagccgttgt cgtagtccac ttggc 25

<210> SEQ ID NO 217
<211> LENGTH: 25
<212> TYPE: DNA
<213> ORGANISM: Artificial Sequence
<220> FEATURE:
<223> OTHER INFORMATION: Primer

<400> SEQUENCE: 217
ctgctggcca gggacatgag gagct 25

<210> SEQ ID NO 218
<211> LENGTH: 25
<212> TYPE: DNA
<213> ORGANISM: Artificial Sequence
<220> FEATURE:
<223> OTHER INFORMATION: Primer

<400> SEQUENCE: 218
ctgctggcca ggtacatgag gagct 25

<210> SEQ ID NO 219
<211> LENGTH: 25
<212> TYPE: DNA
<213> ORGANISM: Artificial Sequence
<220> FEATURE:
<223> OTHER INFORMATION: Primer

<400> SEQUENCE: 219
agctcctcat gtccctggcc agcag 25

<210> SEQ ID NO 220
<211> LENGTH: 25
<212> TYPE: DNA
<213> ORGANISM: Artificial Sequence
<220> FEATURE:
<223> OTHER INFORMATION: Primer

<400> SEQUENCE: 220
agctcctcat gtacctggcc agcag 25

<210> SEQ ID NO 221
<211> LENGTH: 25
<212> TYPE: DNA
<213> ORGANISM: Artificial Sequence
<220> FEATURE:
<223> OTHER INFORMATION: Primer

<400> SEQUENCE: 221
ctcgccgcgg cggggactgc aggta 25

<210> SEQ ID NO 222
<211> LENGTH: 25
<212> TYPE: DNA
<213> ORGANISM: Artificial Sequence
<220> FEATURE:
<223> OTHER INFORMATION: Primer

<400> SEQUENCE: 222
ctcgccgcgg cgaggactgc aggta 25

<210> SEQ ID NO 223
<211> LENGTH: 25
<212> TYPE: DNA
<213> ORGANISM: Artificial Sequence
<220> FEATURE:

```
<223> OTHER INFORMATION: Primer

<400> SEQUENCE: 223
tacctgcagt ccccgccgcg gcgag                                 25

<210> SEQ ID NO 224
<211> LENGTH: 25
<212> TYPE: DNA
<213> ORGANISM: Artificial Sequence
<220> FEATURE:
<223> OTHER INFORMATION: Primer

<400> SEQUENCE: 224
tacctgcagt cctcgccgcg gcgag                                 25

<210> SEQ ID NO 225
<211> LENGTH: 25
<212> TYPE: DNA
<213> ORGANISM: Artificial Sequence
<220> FEATURE:
<223> OTHER INFORMATION: Primer

<400> SEQUENCE: 225
gaccatcttg gaggatgaaa agagg                                 25

<210> SEQ ID NO 226
<211> LENGTH: 25
<212> TYPE: DNA
<213> ORGANISM: Artificial Sequence
<220> FEATURE:
<223> OTHER INFORMATION: Primer

<400> SEQUENCE: 226
gaccatcttg gacgatgaaa agagg                                 25

<210> SEQ ID NO 227
<211> LENGTH: 25
<212> TYPE: DNA
<213> ORGANISM: Artificial Sequence
<220> FEATURE:
<223> OTHER INFORMATION: Primer

<400> SEQUENCE: 227
cctcttttca tcctccaaga tggtc                                 25

<210> SEQ ID NO 228
<211> LENGTH: 25
<212> TYPE: DNA
<213> ORGANISM: Artificial Sequence
<220> FEATURE:
<223> OTHER INFORMATION: Primer

<400> SEQUENCE: 228
cctcttttca tcgtccaaga tggtc                                 25

<210> SEQ ID NO 229
<211> LENGTH: 27
<212> TYPE: DNA
<213> ORGANISM: Artificial Sequence
<220> FEATURE:
<223> OTHER INFORMATION: Primer

<400> SEQUENCE: 229
gttttcctcg tcagatttgt ccttgca                               27

<210> SEQ ID NO 230
```

```
<211> LENGTH: 27
<212> TYPE: DNA
<213> ORGANISM: Artificial Sequence
<220> FEATURE:
<223> OTHER INFORMATION: Primer

<400> SEQUENCE: 230
gttttcctcg tcacatttgt ccttgca                                              27

<210> SEQ ID NO 231
<211> LENGTH: 25
<212> TYPE: DNA
<213> ORGANISM: Artificial Sequence
<220> FEATURE:
<223> OTHER INFORMATION: Primer

<400> SEQUENCE: 231
ttttcctcgt cagatttgtc cttgc                                                25

<210> SEQ ID NO 232
<211> LENGTH: 25
<212> TYPE: DNA
<213> ORGANISM: Artificial Sequence
<220> FEATURE:
<223> OTHER INFORMATION: Primer

<400> SEQUENCE: 232
ttttcctcgt cacatttgtc cttgc                                                25

<210> SEQ ID NO 233
<211> LENGTH: 24
<212> TYPE: DNA
<213> ORGANISM: Artificial Sequence
<220> FEATURE:
<223> OTHER INFORMATION: Primer

<400> SEQUENCE: 233
ttgtccttgc agtcggggcc acta                                                 24

<210> SEQ ID NO 234
<211> LENGTH: 25
<212> TYPE: DNA
<213> ORGANISM: Artificial Sequence
<220> FEATURE:
<223> OTHER INFORMATION: Primer

<400> SEQUENCE: 234
ttgtccttgc agacggggcc accat                                                25

<210> SEQ ID NO 235
<211> LENGTH: 23
<212> TYPE: DNA
<213> ORGANISM: Artificial Sequence
<220> FEATURE:
<223> OTHER INFORMATION: Primer

<400> SEQUENCE: 235
tgtccttgca gtcggggcca cca                                                  23

<210> SEQ ID NO 236
<211> LENGTH: 23
<212> TYPE: DNA
<213> ORGANISM: Artificial Sequence
<220> FEATURE:
<223> OTHER INFORMATION: Primer

<400> SEQUENCE: 236
```

```
tgtccttgca gacggggcca cca                                            23
```

<210> SEQ ID NO 237
<211> LENGTH: 25
<212> TYPE: DNA
<213> ORGANISM: Artificial Sequence
<220> FEATURE:
<223> OTHER INFORMATION: Primer

<400> SEQUENCE: 237

```
agcccagtag cgtgagggct ctgtc                                          25
```

<210> SEQ ID NO 238
<211> LENGTH: 25
<212> TYPE: DNA
<213> ORGANISM: Artificial Sequence
<220> FEATURE:
<223> OTHER INFORMATION: Primer

<400> SEQUENCE: 238

```
agcccagtag cgagagggct ctgtc                                          25
```

<210> SEQ ID NO 239
<211> LENGTH: 25
<212> TYPE: DNA
<213> ORGANISM: Artificial Sequence
<220> FEATURE:
<223> OTHER INFORMATION: Primer

<400> SEQUENCE: 239

```
gacagagccc tcacgctact gggct                                          25
```

<210> SEQ ID NO 240
<211> LENGTH: 25
<212> TYPE: DNA
<213> ORGANISM: Artificial Sequence
<220> FEATURE:
<223> OTHER INFORMATION: Primer

<400> SEQUENCE: 240

```
gacagagccc tctcgctact gggct                                          25
```

<210> SEQ ID NO 241
<211> LENGTH: 25
<212> TYPE: DNA
<213> ORGANISM: Artificial Sequence
<220> FEATURE:
<223> OTHER INFORMATION: Primer

<400> SEQUENCE: 241

```
tcgccttgct cctcgccgcg gcggg                                          25
```

<210> SEQ ID NO 242
<211> LENGTH: 25
<212> TYPE: DNA
<213> ORGANISM: Artificial Sequence
<220> FEATURE:
<223> OTHER INFORMATION: Primer

<400> SEQUENCE: 242

```
tcgccttgct ccccgccgcg gcggg                                          25
```

<210> SEQ ID NO 243
<211> LENGTH: 25
<212> TYPE: DNA
<213> ORGANISM: Artificial Sequence
<220> FEATURE:

-continued

<223> OTHER INFORMATION: Primer

<400> SEQUENCE: 243
cccgccgcgg cgaggagcaa ggcga                         25

<210> SEQ ID NO 244
<211> LENGTH: 25
<212> TYPE: DNA
<213> ORGANISM: Artificial Sequence
<220> FEATURE:
<223> OTHER INFORMATION: Primer

<400> SEQUENCE: 244
cccgccgcgg cggggagcaa ggcga                         25

<210> SEQ ID NO 245
<211> LENGTH: 25
<212> TYPE: DNA
<213> ORGANISM: Artificial Sequence
<220> FEATURE:
<223> OTHER INFORMATION: Primer

<400> SEQUENCE: 245
acggctacag ctacccctcg gtgag                         25

<210> SEQ ID NO 246
<211> LENGTH: 25
<212> TYPE: DNA
<213> ORGANISM: Artificial Sequence
<220> FEATURE:
<223> OTHER INFORMATION: Primer

<400> SEQUENCE: 246
cggctacagc taccccctcg gtgag                         25

<210> SEQ ID NO 247
<211> LENGTH: 25
<212> TYPE: DNA
<213> ORGANISM: Artificial Sequence
<220> FEATURE:
<223> OTHER INFORMATION: Primer

<400> SEQUENCE: 247
ctcaccgagg ggtagctgta gccgt                         25

<210> SEQ ID NO 248
<211> LENGTH: 25
<212> TYPE: DNA
<213> ORGANISM: Artificial Sequence
<220> FEATURE:
<223> OTHER INFORMATION: Primer

<400> SEQUENCE: 248
ctcaccgagg gggtagctgt agccg                         25

<210> SEQ ID NO 249
<211> LENGTH: 25
<212> TYPE: DNA
<213> ORGANISM: Artificial Sequence
<220> FEATURE:
<223> OTHER INFORMATION: Primer

<400> SEQUENCE: 249
cccaggagac gtgctgtgag tcccc                         25

<210> SEQ ID NO 250

```
<211> LENGTH: 25
<212> TYPE: DNA
<213> ORGANISM: Artificial Sequence
<220> FEATURE:
<223> OTHER INFORMATION: Primer

<400> SEQUENCE: 250
cccaggagac gtactgtgag tcccc                                          25

<210> SEQ ID NO 251
<211> LENGTH: 25
<212> TYPE: DNA
<213> ORGANISM: Artificial Sequence
<220> FEATURE:
<223> OTHER INFORMATION: Primer

<400> SEQUENCE: 251
ggggactcac agcacgtctc ctggg                                          25

<210> SEQ ID NO 252
<211> LENGTH: 25
<212> TYPE: DNA
<213> ORGANISM: Artificial Sequence
<220> FEATURE:
<223> OTHER INFORMATION: Primer

<400> SEQUENCE: 252
ggggactcac agtacgtctc ctggg                                          25

<210> SEQ ID NO 253
<211> LENGTH: 25
<212> TYPE: DNA
<213> ORGANISM: Artificial Sequence
<220> FEATURE:
<223> OTHER INFORMATION: Primer

<400> SEQUENCE: 253
ctccccatcg gtaagcgcgg gccgg                                          25

<210> SEQ ID NO 254
<211> LENGTH: 25
<212> TYPE: DNA
<213> ORGANISM: Artificial Sequence
<220> FEATURE:
<223> OTHER INFORMATION: Primer

<400> SEQUENCE: 254
ctccccatcg gtcagcgcgg gccgg                                          25

<210> SEQ ID NO 255
<211> LENGTH: 25
<212> TYPE: DNA
<213> ORGANISM: Artificial Sequence
<220> FEATURE:
<223> OTHER INFORMATION: Primer

<400> SEQUENCE: 255
ccggcccgcg cttaccgatg gggag                                          25

<210> SEQ ID NO 256
<211> LENGTH: 25
<212> TYPE: DNA
<213> ORGANISM: Artificial Sequence
<220> FEATURE:
<223> OTHER INFORMATION: Primer

<400> SEQUENCE: 256
```

```
ccggcccgcg ctgaccgatg gggag                                          25
```

<210> SEQ ID NO 257
<211> LENGTH: 24
<212> TYPE: DNA
<213> ORGANISM: Artificial Sequence
<220> FEATURE:
<223> OTHER INFORMATION: Primer

<400> SEQUENCE: 257

```
ccagtacatg aagctggtgg gaga                                           24
```

<210> SEQ ID NO 258
<211> LENGTH: 25
<212> TYPE: DNA
<213> ORGANISM: Artificial Sequence
<220> FEATURE:
<223> OTHER INFORMATION: Primer

<400> SEQUENCE: 258

```
tcttgatctt ggcctgggga cagag                                          25
```

<210> SEQ ID NO 259
<211> LENGTH: 23
<212> TYPE: DNA
<213> ORGANISM: Artificial Sequence
<220> FEATURE:
<223> OTHER INFORMATION: Primer

<400> SEQUENCE: 259

```
cagtacatga agctggtggg agg                                            23
```

<210> SEQ ID NO 260
<211> LENGTH: 23
<212> TYPE: DNA
<213> ORGANISM: Artificial Sequence
<220> FEATURE:
<223> OTHER INFORMATION: Primer

<400> SEQUENCE: 260

```
cttgatcttg gcctggggac aga                                            23
```

The invention claimed is:

1. A method for detecting a first mutation in the low density lipoprotein receptor (LDL-R) gene of a human subject, the method comprising the steps of:
   (a) providing a biological sample comprising LDL-r gene nucleic acids of the subject;
   (b) analyzing said LDL-r gene nucleic acids of the subject; and
   (c) detecting the presence of an inserted T nucleotide in SEQ ID NO: 1 between the positions corresponding to positions 28562 and 28563 of SEQ ID NO: 1.

2. The method according to claim 1, wherein the analyzing comprises treating the sample with a restriction endonuclease that cleaves the nucleic acids in the sample to generate an additional cleavage fragment when said inserted T nucleotide is present, as compared to a number of cleavage fragments generated when said inserted T nucleotide is absent.

3. The method according to claim 1, wherein the analyzing comprises contacting the sample with a probe or probes that hybridize with the LDL-r gene nucleic acids.

4. The method according to claim 3, wherein the probe or probes are one or more oligonucleotides selected from the group consisting of SEQ ID NO: 56, 57, 58, and 59.

5. The method according to claim 1, wherein the analyzing step further comprises determining whether a second mutation is also present in the LDL-r gene of the subject, wherein said second mutation is a C nucleotide at the position corresponding to position 28562 of SEQ ID NO: 1.

6. The method according to claim 1, wherein the analyzing step further comprises determining whether a second mutation is also present in the LDL-r gene of the subject, wherein said second mutation is a Q71E mutation in the LDL-r gene.

7. The method according to claim 1, wherein the method further comprises detecting a mutation selected from: (−23) A>C, 1054 del11, 108delC, 1197del9, 1207delT, 1432delG, 191-2delAinsCT, 2184delG, 231delC, 2399del5/ins4, 338del16, 509insC, 675del15, 684dup12, 941-39C>T, C195R, C255G, C319Y, D1570, D630N, E291X, H635N, N59K, T41M, W515X, Y379X, Y421X, T433N, 818del8, 1423delGC/insA, 1204insT, 451 del3, G516X, 2389+4A>0, 1815del11, 1186+5G>A, T740M, 1771T, R279G, T4461, H562Q, C74Y, D686Y, G(−2)R, E579D, S205C, D200V, V766E, L(−6)P, 2544insC, C42Y, 2389+3A>C, [1587-5del5; 1587del31].

* * * * *